US012668609B2

(12) United States Patent
Sowemimo-Coker

(10) Patent No.: US 12,668,609 B2
(45) Date of Patent: Jun. 30, 2026

(54) METHODS AND DEVICES FOR THE ENRICHMENT OF IMMUNOGLOBULIN FROM BLOOD

(71) Applicant: Haemonetics Corporation, Boston, MA (US)

(72) Inventor: Samuel O. Sowemimo-Coker, Dix Hills, NY (US)

(73) Assignee: Haemonetics Corporation, Boston, MA (US)

( * ) Notice: Subject to any disclaimer, the term of this patent is extended or adjusted under 35 U.S.C. 154(b) by 704 days.

(21) Appl. No.: 17/564,976

(22) Filed: Dec. 29, 2021

(65) Prior Publication Data

US 2022/0119442 A1    Apr. 21, 2022

Related U.S. Application Data

(63) Continuation of application No. 16/090,689, filed as application No. PCT/US2017/025918 on Apr. 4, 2017, now abandoned.

(60) Provisional application No. 62/318,686, filed on Apr. 5, 2016, provisional application No. 62/318,679, filed on Apr. 5, 2016, provisional application No. 62/318,677, filed on Apr. 5, 2016, provisional application No. 62/318,662, filed on Apr. 5, 2016.

(51) Int. Cl.
| | |
|---|---|
| *A61K 39/395* | (2006.01) |
| *A61M 1/34* | (2006.01) |
| *C07K 1/14* | (2006.01) |

(52) U.S. Cl.
CPC ........... *C07K 1/145* (2013.01); *A61M 1/3437* (2014.02); *A61M 1/3496* (2013.01); *A61M 2202/0419* (2013.01); *A61M 2202/0427* (2013.01)

(58) Field of Classification Search
CPC ........ C07K 1/145; C07K 16/065; C07K 1/22; A61M 1/3437; A61M 1/3496; A61M 2202/0419; A61M 2202/0427; A61M 1/3486; G01N 33/6854
See application file for complete search history.

(56) References Cited

U.S. PATENT DOCUMENTS

| | | | |
|---|---|---|---|
| 4,086,924 | A | 5/1978 | Latham, Jr. |
| 4,424,132 | A | 1/1984 | Iriguchi |
| 4,447,415 | A | 5/1984 | Rock et al. |
| 4,507,119 | A | 3/1985 | Spencer |
| 4,695,460 | A | 9/1987 | Holme |
| 4,737,214 | A | 4/1988 | Leurink et al. |
| 4,913,756 | A | 4/1990 | Shaposka et al. |
| 4,983,158 | A | 1/1991 | Headley |
| 5,344,561 | A | 9/1994 | Pall et al. |
| 5,387,187 | A | 2/1995 | Fell et al. |
| 5,672,481 | A | 9/1997 | Minshall |

| | | | |
|---|---|---|---|
| 6,498,236 | B1 | 12/2002 | Lihme et al. |
| 6,629,919 | B2 | 10/2003 | Egozy |
| 7,144,743 | B2 | 12/2006 | Boschetti et al. |
| 7,794,720 | B2 | 9/2010 | Wilson |
| 8,709,707 | B2 | 4/2014 | Hess et al. |
| 8,993,734 | B2 | 3/2015 | Bruckschwaiger et al. |
| 2002/0032112 | A1 | 3/2002 | Pages |
| 2003/0171548 | A1 | 9/2003 | Benes et al. |
| 2006/0016753 | A1 | 1/2006 | Sowemimo-Coker et al. |
| 2008/0050368 | A1 | 2/2008 | Celniker et al. |
| 2011/0065901 | A1 | 3/2011 | Soice et al. |
| 2012/0219633 | A1 | 8/2012 | Sowemimo-Coker |
| 2013/0331252 | A1 | 12/2013 | Brunner et al. |
| 2014/0046038 | A1 | 2/2014 | Ishihara |
| 2014/0255399 | A1 | 9/2014 | Freimoser-Grundschober et al. |
| 2014/0255409 | A1 | 9/2014 | Nilsson |
| 2015/0133644 | A1 | 5/2015 | Bruckschwaiger et al. |
| 2016/0017272 | A1 | 1/2016 | Gjerde |

(Continued)

FOREIGN PATENT DOCUMENTS

| | | |
|---|---|---|
| JP | 2001-17540 A | 1/2001 |
| JP | 2013-501721 A | 1/2013 |
| JP | 2014-514936 A | 6/2014 |

(Continued)

OTHER PUBLICATIONS

David M. Ward (Conventional Apheresis Therapies: A Review. J of Clinical Apheresis, vol. 26, pp. 230-238) (Year: 2011).*
European Patent Office, Office Action for European Application No. 17779649.7 dated Apr. 26, 2023 (4 pages).
Steel, et al., "Efficient and Specific Removal of Albumin from Human Serum Samples," Molecular & Cellular Proteomics, vol. 2, No. 4, pp. 262-270, Apr. 1, 2003.
United States Patent and Trademark Office as the International Searching Authority, Authorized Officer: Blaine R. Copenheaver, International Search Report and Written Opinion of the International Searching Authority, PCT/US2017/025918, Jun. 27, 2017, 21 pages.

(Continued)

*Primary Examiner* — Yunsoo Kim
(74) *Attorney, Agent, or Firm* — Nutter McClennen & Fish LLP

(57)    ABSTRACT

A method for extracting at least 55% of immunoglobulin such as IgG from a biological fluid. The biological fluid containing immunoglobulin is contacted with a solid support covalently bonded to a ligand that specifically binds to immunoglobulin under conditions sufficient for non-covalent binding of immunoglobulin to the ligand. The solid support is contacted with an elution solution under conditions whereby the non-covalently bound immunoglobulin is released from the ligand and into the elution solution, wherein at least 55% of the IgG present in the biological fluid is extracted into the elution solution. The method, in some embodiments, provides a method for enriching immunoglobulin from a biological fluid comprising obtaining an initial biological fluid suspected of containing immunoglobulin and removing non-immunoglobulin components naturally occurring in the initial biological fluid to obtain a non-immunoglobulin component-reduced biological fluid.

11 Claims, 27 Drawing Sheets

(56)                References Cited

U.S. PATENT DOCUMENTS

| | | |
|---|---|---|
| 2016/0122385 A1 | 5/2016 | Bian et al. |
| 2020/0325169 A1 | 10/2020 | Sowemimo-Coker |

FOREIGN PATENT DOCUMENTS

| | | |
|---|---|---|
| WO | WO 95/31209 | 11/1995 |
| WO | WO 2004/024318 | 3/2004 |
| WO | WO 2005/073711 | 8/2005 |
| WO | WO 2006/076480 | 7/2006 |
| WO | WO 2008/153472 | 12/2008 |
| WO | WO 2009/129132 | 10/2009 |
| WO | WO 2011/017514 | 2/2011 |
| WO | WO 2012/118735 | 9/2012 |
| WO | WO 2013/062479 | 5/2013 |
| WO | WO 2014/024514 | 2/2014 |
| WO | WO 2015/136217 | 9/2015 |

OTHER PUBLICATIONS

Tanaka, et al., "High quality human immunoglobulin G purified from Cohn fractions by liquid chromatography," Brazilian Journal of Medical and Biological Research, vol. 33, pp. 27-30, Jan. 2000.

Haroun, et al., "Measurement of IgG Levels Can Serve as a Biomarker in Newly Diagnosed Diabetic Children," Journal of Clinical Biochemistry and Nutrition, vol. 40, pp. 56-61, Jan. 2007.

Osselaer, et al., (Abstract only) "A prospective observational cohort safety study of 5106 platelet transfusions with components prepared with photochemical pathogen inactivation treatment," Transfusion vol. 48, No. 6, pp. 1061-1071, Mar. 13, 2008.

Osselaer, et al., (Abstract only) "An active haemovigilance programme characterizing the safety profile of 7437 platelet transfusions prepared with amotosalen photochemical treatment" Vox Sanguinis, vol. 94, No. 4, pp. 315-323, Feb. 5, 2008.

Ward, "Conventional Apheresis Therapies: A Review," Journal of Clinical Apheresis, vol. 26, No. 5, pp. 230-238, Jan. 1, 2011.

European Patent Office, Extended European Search Report, 17779649. 7, Sep. 18, 2019, 8 pages.

Palmer, et al., "Removal of Anti-HLA Antibodies by Extracorporeal Immunoadsorption to Enable Renal Transplantation," The Lancet, Elsevier, Amsterdam, NL, vol. 1, No. 8628, Jan. 7, 1989.

European Patent Office, Examination Report, 177796497, Mar. 31, 2021, 8 pages.

Japanese Patent Office, Office Action, 2018-552228, Apr. 27, 2021, 4 pages.

Japanese Patent Office, (machine translation), Office Action, 2018-552228, Apr. 27, 2021, 4 pages.

China National Intellectual Property Administration, Office Action, application No. 201780028170.2, Jan. 30, 2022, 9 pages.

China National Intellectual Property Administration (English translation), Office Action, application No. 201780028170.2, Jan. 30, 2022, 9 pages.

Japanese Patent Office, Office Action, application No. 2018-552,228, Dec. 24, 2021, 3 pages.

Japanese Patent Office, (English translation), Office Action, application No. 2018-552,228, Dec. 24, 2021, 3 pages.

Mccaw et al., "Evaluation of a novel methacrylate-based protein A resin for the purification of immunoglobulins and Fe-fusion proteins" Biotech. Prag. 2014, 30(5) (Year: 2014).

Zhou et al., "Membrane supports as the stationary phase in high-performance immunoaffinity chromatography" Anal. Chem 1999, 71, 115-118 (Year: 1999).

Pereira et al., "Selection of column lenght and particle size for high resolution, fast LC and LC/MS" Thermo Fish Scientific (Year: 2010).

Natarajan et al., "Protein A chromatography at high titers" Biotech. and Bioeng. 110(9), Sep. 2013, pp. 2445-2451 (Year: 2013).

\* cited by examiner

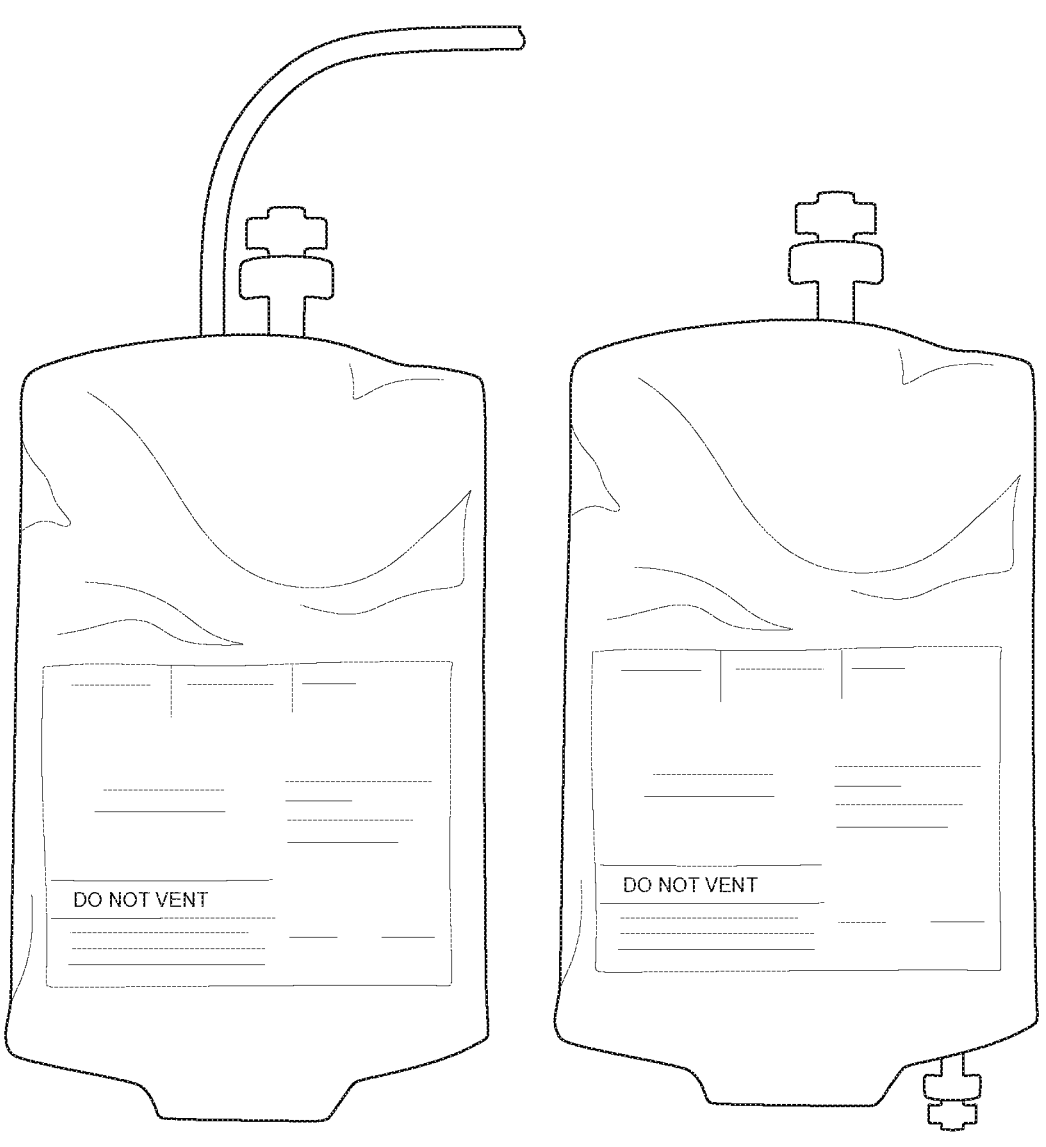
*Figure 8A*          *Figure 8B*

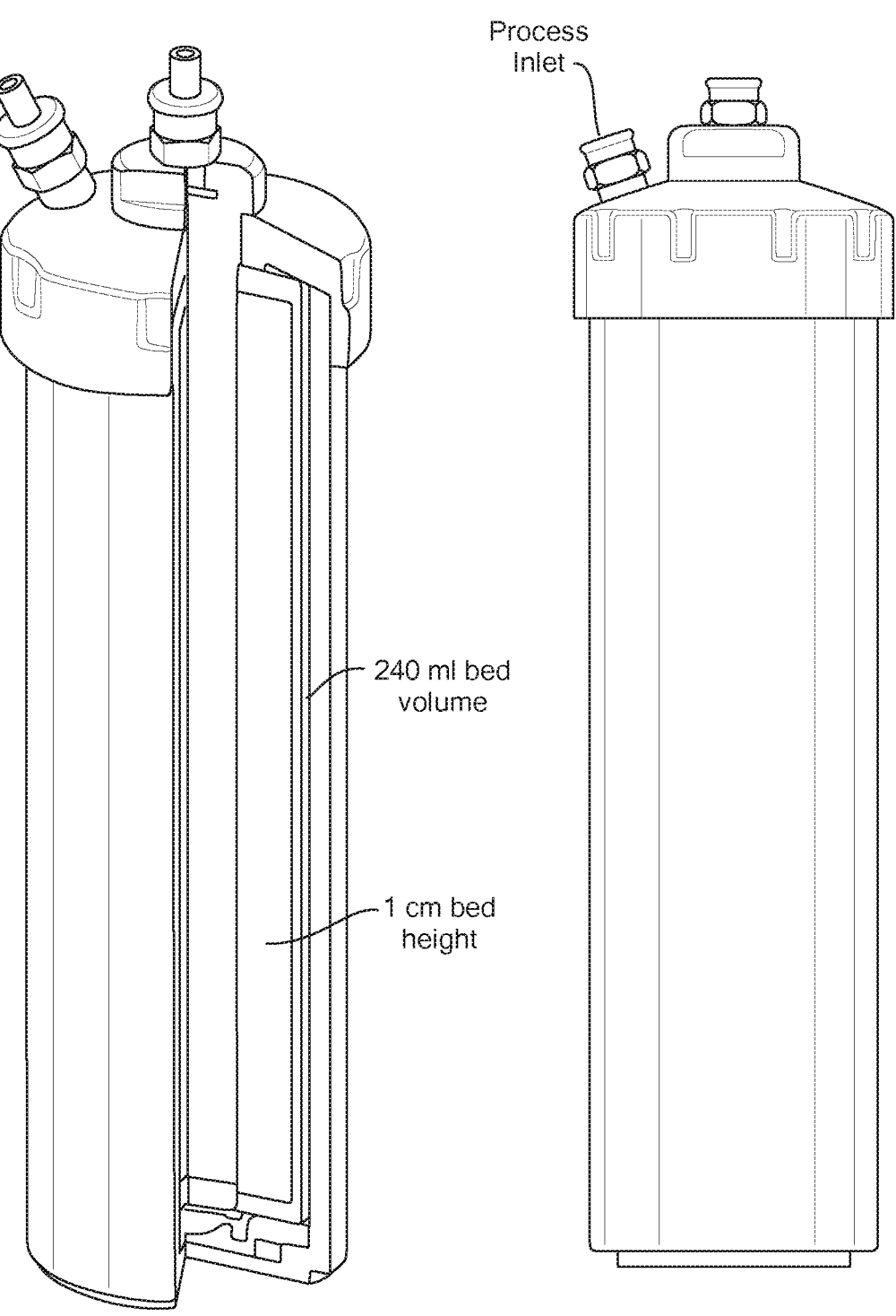
*Figure 9A*            *Figure 9B*

*Figure 14*

Pseudo-Disposable Set for Removing IgG from Plasma

Figure 15

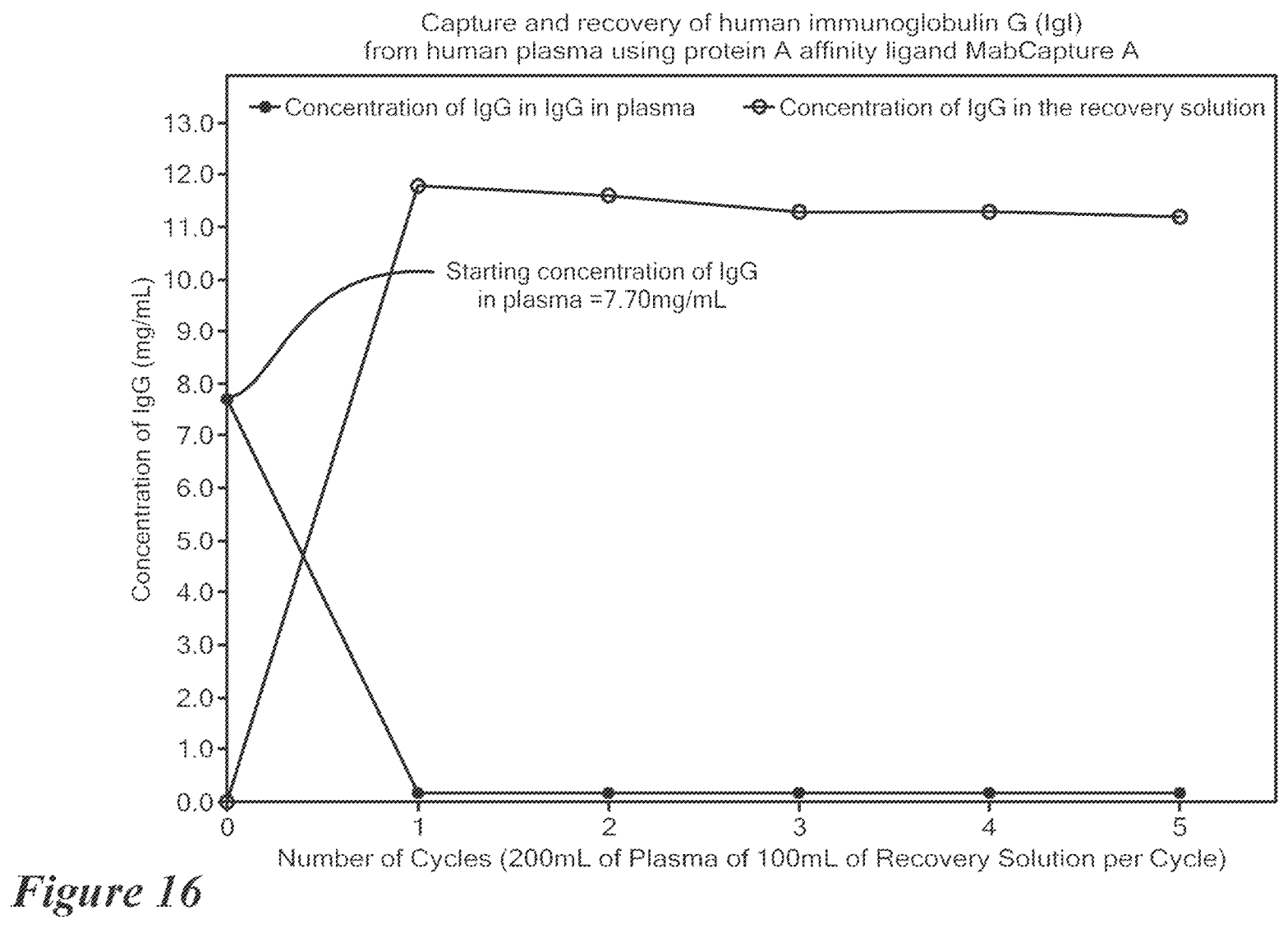

Capture and recovery of human immunoglobulin G (Igt)
from human plasma using protein A affinity ligand MabCapture A —◆— Concentration of IgG in IgG in plasma        —◇— Concentration of IgG in the recovery solution Starting concentration of IgG
in plasma =7.70mg/mL Concentration of IgG (mg/mL)

Number of Cycles (200mL of Plasma of 100mL of Recovery Solution per Cycle)

*Figure 16*

METHODS AND DEVICES FOR THE ENRICHMENT OF IMMUNOGLOBULIN FROM BLOOD

CROSS REFERENCE TO RELATED APPLICATIONS

This application is a continuation of U.S. application Ser. No. 16/090,689 filed Oct. 2, 2018, which is a U.S. national phase entry of International Application No. PCT/US17/25918 filed Apr. 4, 2017, which claims priority benefit from U.S. Provisional Application No. 62/318,677 filed Apr. 5, 2016, and also from U.S. Provisional Application No. 62/318,662 filed Apr. 5, 2016, and also from U.S. Provisional Application No. 62/318,679 filed Apr. 5, 2016, and also from U.S. Provisional Application No. 62/318,686 filed Apr. 5, 2016, the entire disclosures of each of which is incorporated herein by reference.

BACKGROUND OF THE INVENTION

The present invention relates the fields of biology and medicine. In particular, the invention relations to human blood products and the preparation thereof.

Blood is a bodily fluid in humans and other animals that is involved in the transport of molecules (including oxygen, carbon dioxide, nutrients, and metabolic waste products) to and from various cells in the body. In vertebrate animals, blood is composed of blood cells (including red blood cells and white blood cells), and plasma, the liquid component of blood that holds the blood cells and blood molecules in suspension. Plasma makes up about 55% of the body's total blood volume.

Blood can be transferred from one individual to another. Thus, humans have donated blood for use by other humans in need. Blood from non-human animals (e.g., veterinary animals such as cats and dogs) can be transferred from a healthy donor to a recipient in need. Donated blood may be stored in a blood bank.

Donated blood can be separated into components. In this case, blood which contains all of the fluid of blood taken directly from a donor is called whole blood. Note that while substances may be added to whole blood (e.g., heparin or EDTA to prevent coagulation), no components (e.g., liquid or cells) are removed from whole blood.

Whole blood can also be processed to separate the individual components. For example, red blood cells can be separated and enriched. Because human white blood cells (but not red blood cells) express major histocompatibility complex antigens, the red blood cells can be further processed by leuko-reducing the red blood cells to remove the number of white blood cells in the enriched red blood cell population.

Using the apheresis technology, blood of a donor (e.g., a healthy volunteer) can be collected and passed through an apparatus that separates a desired component of whole blood. In some apheresis systems, the remainder of the whole blood after the desired component is removed is back to the donor. For example, in plateletpheresis (also called thrombocytapheresis or thrombapheresis), platelets are the desired component. Thus, in plateletpheresis, donor whole blood is passed through an apparatus that collects platelets, and the platelet-reduced blood (which may be referred to as the remainder) is returned to the donor. Other desired components of blood, including red blood cells and plasma, can be selectively collected using apheresis.

Various commercially available apparatuses are used to perform apheresis. For example, the PCS®2 plasma collection system and the MCS®+9000 mobile platelet collection system are commercially available from Haemonetics Corp. (Braintree, Massachusetts, USA). Terumo BCT, Inc. also sells apheresis systems including the Trima Accel® apheresis system, the COBE® Spectra Apheresis System and the Spectra Optia® Apheresis system. Fenwal Inc. (Lake Zurich, Illinois, USA) also sells the Amicus® Thrombapheresis apheresis machine.

Another component that can be separated and enriched from whole blood are stem cells. FIG. 1 schematically depicts a patient (e.g., a healthy volunteer donor) donating stem cells using an apheresis machine.

Another component that can be separated and enriched from whole blood are platelets, which are a type of white blood cells (also called leukocyte). Unlike most leukocytes, a platelet cell lacks a nucleus. FIG. 2 shows a patient donating platelets using the MCS®+ 9000 mobile platelet collection system sold by Haemonetics Corp. (Braintree, Massachusetts, USA).

The plasma portion of whole blood can also be collected. FIG. 3 depicts a non-limiting machine, namely the PCS®2 machine sold by Haemonetics Corp. (Braintree, Massachusetts, USA), that collects plasma.

Generally, apheresis systems (also called apheresis units) incorporate flexible tubing (e.g., polyvinyl tubing) that draws blood from the patient and moves it through centrifuges and/or filters to separate blood products. The blood is then returned to the patient via tubing or is collected in bags, often suspended from a pole, for donation or disposal. An apheresis system often includes a display and control panel to allow the operator (e.g., a doctor or a nurse) to program the system and to view progress and/or alerts. Safety features of apheresis systems include pressure sensors, ultrasonic air-bubble detectors, optical fluid-level detectors, and dry-heat fluid warmers. The warmers help prevent hypothermia caused by infusing low-temperature fluids. Some apheresis systems may have wheels or may be placed on a cart.

When in use, the apheresis system typically automatically controls the centrifuge, pump, and other settings. For example, rotary peristaltic pumps draw blood from the patient or donor (e.g., a healthy volunteer) and pump the blood through filters or centrifuges. In general, filters separate blood components based on size and centrifuges separate blood components by density. Some apheresis machines include optical sensors to detect plasma-cell interfaces to minimize contamination from other components. Centrifuges have inlet and outlet ports and compartments to keep components separated. Pumps move the blood products into collection bags, add anticoagulant, and reinfuse fluids. Replacement fluids (e.g., saline, serum albumin, plasma protein fraction, fresh frozen plasma) can be infused into the patient or donor to maintain appropriate intravascular volume and pressure.

Although the existing apheresis systems are useful for processing blood and blood products, there remains a need for improved apheresis systems, or methods of modifying such systems, to obtain blood products from donors or patients.

SUMMARY OF THE EMBODIMENTS

The invention provides improved methods and devices for enriching and/or extracting immunoglobulins from blood and blood products.

Accordingly, in one aspect, the invention provides a method for extracting at least 55% of immunoglobulin, such as IgG, present in a biological fluid from the biological fluid comprising: (a) contacting a biological fluid suspected of containing the immunoglobulin with a solid support covalently bonded to a ligand that specifically binds to the immunoglobulin under conditions sufficient for non-covalent binding of immunoglobulin in the biological fluid to the ligand; and (b) contacting the solid support with an elution solution under condition whereby the non-covalently bound immunoglobulin is released from the ligand and into the elution solution, wherein at least 55% of the immunoglobulin present in the biological fluid is extracted into the elution solution.

In some embodiments, the immunoglobulin is IgG.

In some embodiments, the method comprises repeating step (a) at least once prior to step (b). In some embodiments, the immunoglobulin in the elution solution is purified. In some embodiments, the immunoglobulin in the elution solution is at least 90% free of other molecules naturally occurring in the biological fluid.

In some embodiments, at least 60% of the immunoglobulin in the biological fluid is extracted from the biological fluid. In some embodiments, at least 70% of the immunoglobulin in the biological fluid is extracted from the biological fluid. In some embodiments, at least 90% of the immunoglobulin in the biological fluid is extracted from the biological fluid.

In some embodiments, step (a) comprises passing the biological fluid through a container comprising the solid support. In some embodiments, the solid support is beads. In some embodiments, the solid support is the inner surface of the container. In some embodiments, the container is a column. In some embodiments, the column is a radial column. In some embodiments, the column is an axial column. In some embodiments, the container is a bag. In some embodiments, the bag comprises a mesh lining an inner surface of the bag, wherein the beads are contained between the inner surface of the bag and the mesh lining.

In some embodiments, the solid support are beads. In some embodiments, the beads have an individual diameter of between about 30 um to about 80 um.

In some embodiments, the ligand is a protein from a bacteria family selected from the group consisting of *Staphylococcus* or *Streptococcus*, or a derivative thereof. In some embodiments, the ligand is protein A from *Staphylococcus aureus* or a derivative thereof.

In some embodiments, the method further comprises adding a neutralizing buffer to the elution solution comprising the extracted immunoglobulin to result in a final solution comprising the extracted immunoglobulin having a pH of between about 7.0 and about 8.0. In some embodiments, the elution solution has a pH of between about 2.0 and about 3.0.

In some embodiments, the biological fluid passing through the container has a flow rate of between about 50 ml/minute to about 120 ml/minute.

In some embodiments, the biological fluid passing through the container has a backpressure of between about 10 mm Hg to about 100 mmHg.

In some embodiments, the container has a capacity to bind to at least 90% of the immunoglobulin present in the biological fluid prior to step (a). In some embodiments, the container has a capacity to bind to less than 50% of the immunoglobulin present in the biological fluid prior to step (a). In some embodiments, the biological fluid is selected from the group consisting of whole blood, platelet-rich plasma, plasma, and serum. In some embodiments, the biological fluid is from a human.

In another aspect, the invention provides a method for enriching immunoglobulin from an initial biological fluid, comprising obtaining an initial biological fluid suspected of containing immunoglobulin and removing non-immunoglobulin components naturally occurring in the initial biological fluid to obtain a non-immunoglobulin component-reduced biological fluid enriched for immunoglobulin (as compared to the initial biological fluid). In some embodiments, the method comprises obtaining an initial biological fluid suspected of containing immunoglobulin and contacting the initial biological fluid with a solid support covalently bonded to a ligand that specifically binds to a non-immunoglobulin component in the initial biological fluid under conditions sufficient for non-covalent binding of non-immunoglobulin component in the initial biological fluid to the ligand, and removing the bound non-immunoglobulin components to obtain a non-immunoglobulin component-reduced biological fluid enriched for immunoglobulin. In some embodiments, the non-immunoglobulin component-reduced biological fluid comprises at least 55% of the immunoglobulin present in the initial biological fluid. In some embodiments, at least 60% of the immunoglobulin in the biological fluid is enriched from the initial biological fluid. In some embodiments, at least 70% of the immunoglobulin in the biological fluid is enriched from the initial biological fluid. In some embodiments, at least 80% of the immunoglobulin in the biological fluid is enriched from the initial biological fluid. In some embodiments, at least 90% of the immunoglobulin in the biological fluid is enriched from the initial biological fluid.

In some embodiments, the immunoglobulin is IgG. In some embodiments, the biological fluid is selected from the group consisting of whole blood, platelet-rich plasma, plasma, and serum. In some embodiments, the biological fluid is from a human.

In some embodiments, the non-immunoglobulin components comprise coagulation cascade proteins, lipids, carbohydrates, albumin, and complement proteins.

In another aspect, the invention provides a container for use in a plasmapheresis machine, the container comprising a solid support covalently bonded a ligand that specifically binds to a target molecule selected from the group consisting of an IgG molecule, a non-IgG molecule, an immunoglobulin, and a non-immunoglobulin molecule, wherein the container is configured to support a biological fluid passing through the container at a flow rate of between about 20 ml/minute to about 120 ml/minute. some embodiments, the container is configured to support a biological fluid passing through the column with a backpressure of between about 10 mm Hg to about 100 mmHg.

In some embodiments, the ligand is a protein from a bacteria family selected from the group consisting of *Staphylococcus* or *Streptococcus*, or a derivative thereof that can specifically bind to an immunoglobulin. In some embodiments, the ligand is protein A from *Staphylococcus aureus* or a derivative thereof that can specifically bind to an immunoglobulin.

In some embodiments, the ligand is cibacron blue, or a derivative thereof that can specifically bind to an albumin molecule.

In some embodiments, the solid support are beads. In some embodiments, each of the beads has an individual diameter of between about 30 um to about 80 um. In some embodiments, the container is a column. In some embodiments, the container is a bag.

In another aspect, the invention provides a bag configured for used in an apheresis system such as a plasmapheresis machine or a plateletpheresis machine, the bag comprising an inner surface and a mesh lining on the inner surface thereby creating a pocket on the inner surface, wherein beads covalently bonded to ligand that specifically binds to a target molecule selected from the group consisting of an IgG molecule, a non-IgG molecule, an immunoglobulin, and a non-immunoglobulin molecule, are located within the pocket.

In yet another aspect, the invention provides an apheresis system configured to extract at least 55% of immunoglobulin such as IgG present in a biological fluid using a container comprising a solid support covalently bonded to a ligand that specifically binds to IgG in a method (e.g., a method that is partially or fully automated) comprising (a) contacting a biological fluid suspected of containing immunoglobulin, with the solid support covalently bonded to the ligand that specifically binds to immunoglobulin in the container under conditions sufficient for non-covalent binding of immuno-globulin to the ligand; and (b) contacting the solid support in the container with an elution solution under condition whereby the non-covalently bound immunoglobulin is released from the ligand and into the elution solution to obtain elution solution comprising immunoglobulin. In some embodiments, the apheresis system is a closed system. In some embodiments, the apheresis system is a plateletpheresis system or a plasmapheresis system. In some embodiments, the solid support are beads. In some embodiments, the ligand is a protein from a bacteria family selected from the group consisting of *Staphylococcus* or *Streptococcus*, or a derivative thereof. In some embodiments, the ligand is protein A from *Staphylococcus aureus* or a deriva-tive thereof. In some embodiments, the immunoglobulin in the elution solution is purified.

In some embodiments, at least 60% of the immunoglobu-lin in the biological fluid is extracted from the biological fluid. In some embodiments, at least 70% of the immuno-globulin in the biological fluid is extracted from the bio-logical fluid. In some embodiments, at least 90% of the immunoglobulin in the biological fluid is extracted from the biological fluid.

In some embodiments, the method of the system further comprises (c) adding a neutralizing buffer to the elution solution comprising the immunoglobulin to result in a final solution comprising the system having a pH of between about 7.0 and about 8.0.

In another aspect, the invention provides an apheresis system configured to enrich at least 55% of immunoglobulin (e.g., IgG) present in a biological fluid using a container comprising a solid support covalently bonded to a ligand that specifically binds to a non-immunoglobulin component in the biological fluid, in a method (e.g., a partially auto-mated or fully automated method) comprising (a) contacting a biological fluid suspected of containing immunoglobulin with the solid support in the container under conditions sufficient for non-covalent binding of the non-immuno-globulin component to the ligand; and (b) collecting the non-immunogloblulin depleted biological fluid from the container, the non-immunoglobulin depleted biological fluid being enriched for immunoglobulin. In some embodi-ments, the apheresis system is a closed system. In some embodiments, the apheresis system is a plateletpheresis system or a plasmapheresis system. In some embodiments, the solid support are beads. In some embodiments, the ligand is cibracron blue or a derivative thereof (e.g., a derivative that specifically binds to albumin).

In some embodiments, at least 60% of the immunoglobu-lin in the biological fluid is enriched. In some embodiments, at least 70% of the immunoglobulin in the biological fluid is enriched. In some embodiments, at least 80% of the immu-noglobulin in the biological fluid is enriched. In some embodiments, at least 90% of the immunoglobulin in the biological fluid is enriched.

In some embodiments, the biological fluid suspected of containing immunoglobulin (such as IgG) is a blood product produced by a component of the apheresis system. In some embodiments, the blood product is platelet-enriched plasma. In some embodiments, the blood product is plasma. In some embodiments, the blood product is the blood product is whole blood supplemented with an anticoagulant.

In some embodiments, the container is a column. In some embodiments, the container is a bag.

In some embodiments, the container is configured to support a biological fluid passing through the container at a flow rate of between about 20 ml/minute to about 120 ml/minute. In some embodiments, the container is config-ured to support a biological fluid passing through the con-tainer with a backpressure of between about 10 mm Hg to about 100 mmHg.

In some embodiments, systems described herein are closed systems. In some embodiments, the method (e.g., the automated method) occurs without removing the container from the system.

BRIEF DESCRIPTION OF THE DRAWINGS

The foregoing features of embodiments will be more readily understood by reference to the following detailed description, taken with reference to the accompanying draw-ings, in which:

In FIG. 1, stem cells are removed from the donor, and the non-stem cell components of whole blood are returned to the donor.

In FIG. 6A, first platelets are removed from whole blood (and subsequently processed to product a platelet product) and then plasma is removed from the remaining cells. IgG is removed from the plasma (and subsequently processed to product an IgG product) and the IgG-depleted plasma is combined with the remaining cells (i.e., red blood cells and non-platelet white blood cells) and administered back to the patient. In FIG. 6B, platelet-rich plasma is removed from whole blood, and then IgG is removed from the platelet-rich plasma which, after processing, results in purified IgG product and IgG-depleted platelet rich plasma product. The remaining red blood cells and non-platelet white blood cells are mixed with isotonic saline and returned to the patient in FIG. 6B. In FIG. 6C, plasma is removed from whole blood, and from this plasma, IgG is extracted. After further processing, a purified IgG product and an IgG-depleted plasma product are produced. The remaining red blood cells and white blood cells (including platelets) are mixed with isotonic saline and returned to the donor in FIG. 6C.

As shown in FIG. 7, the only component returned to the donor in the depicted method is the non-platelet white blood cells (e.g., lymphocytes and monocytes) which are suspended in Ringer's solution (an isotonic solution).

FIG. 8A is a photograph of a non-limiting representation of a bag that can be used in the invention. In the depicted bag, an input port and an output port are located at the top of the bag.

FIG. 8B is a photograph of a non-limiting representation of a bag that can be used in the invention. In the depicted bag, an input port is located at the top of the bag and the output port is located at the bottom of the bag.

FIGS. 9A-9C are photographs of a non-limiting radial flow column that can be used in the invention. FIG. 9B shows the exterior of the column. FIG. 9A shows the column of FIG. 9B with a length-wise section removed to show the packed beads in the column. FIG. 9C shows a slice of the column of FIG. 9B, with the individual layers of packed beads visible in the cut-away section to the right of the slice.

FIGS. 10A and 10B are schematic diagrams showing how a radial column, a non-limiting container comprising a solid support covalently bonded to a ligand that specifically binds to IgG, can be incorporated into a plasmapheresis system, such as the PCS®2 system (FIG. 10A) and a plateletpheresis system, such as the MCS®+9000 system (FIG. 10B). Blood compatible tubing (e.g., made from polypropylene) connects the various bags, bowls, and columns to each other. FIGS. 10A and 10B show a radial column as the container; however another type container such as an axial column or a bag can be employed.

FIGS. 10C and 10D are schematic diagrams showing how a bag, a nonlimiting container comprising a solid support covalently bonded to a ligand that specifically binds to IgG, can be incorporated into a plasmapheresis system, such as the PCS®2 system (FIG. 10C) and a plateletpheresis system, such as the MCS®+9000 system (FIG. 10D). Blood compatible tubing (e.g., made from polypropylene) connects the various bags and bowls to each other. FIGS. 10C and 10D show a bag such as the bag depicted in FIGS. 8A-8B employed as the container; however another type container such as an axial column or a bag can be employed.

FIGS. 10E and 10F are schematic diagrams showing how a radial column, a non-limiting container comprising a solid support covalently bonded to a ligand that specifically binds to a non-IgG blood component, can be incorporated into a plasmapheresis system, such as the PCS®2 system (FIG. 10E) and a plateletpheresis system, such as the MCS®+9000 system (FIG. 10F). Blood compatible tubing (e.g., made from polypropylene) connects the various bags and bowls to each other. Note that FIGS. 10E and 10F show a radial column employed as the container; however another type container such as an axial column or a bag can be employed.

FIG. 14 is a line graph showing the amount of IgG captured from plasma by being bound to MabCapture™ A media (a non-limiting solid support covalently bound to a ligand that specifically binds to IgG) in a radial column (a non-limiting type of container comprising the solid support) (dark red line), and the amount of IgG recovered from the column into recovery (i.e., elution) solution (light green line). Shown are the averaged amounts from five tests from five different donors at 1000 ml/cycle for five cycles in a radial column with a bed height of 3 cm that is reused for all five cycles. The starting amounts of IgG in the plasma are shown in Table 1.

FIG. 15 is a schematic showing a series of bags that can be used with a disposable column containing protein A-coated beads in a non-limiting embodiment of the invention.

FIG. 16 is a line graph showing the amount of IgG present in 200 ml of human plasma (light green line) that was recovered from the plasma into recovery solution (dark red line) using protein A-coated beads, a non-limiting solid support covalently linked to a ligand in accordance with the present invention.

DETAILED DESCRIPTION OF SPECIFIC EMBODIMENTS

Figure 1:
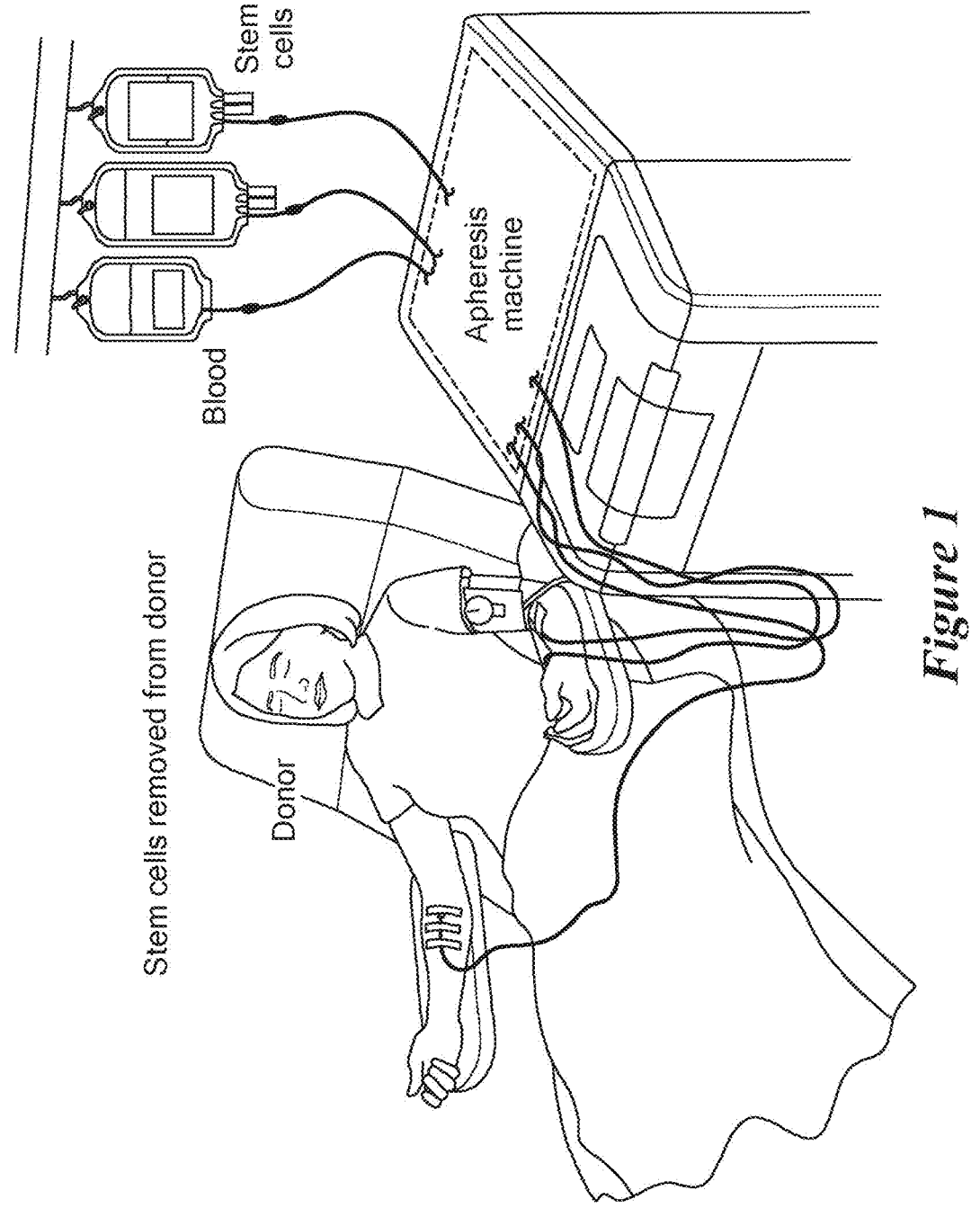
FIG. 1 is a schematic depicting a non-limiting embodi-ment of apheresis.

The invention stems, in part, from the development of methods and instruments that allow the extraction of at least 60% of immunoglobulins (e.g., IgG) from a biological fluid such as blood.

The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

Terms defined or used in the description and the claims shall have the meanings indicated, unless context otherwise requires. Technical and scientific terms used herein have the meaning commonly understood by one of skill in the art to which the present invention pertains, unless otherwise defined. Any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, by "blood" is meant whole blood and blood component products. Whole blood is simply the fluid that circulates throughout an organism, such as a human. Whole blood includes components including cells (e.g., red blood cells, white blood cells), proteins (e.g., insulin, immunoglobulins, albumin), fatty acids and carbohydrates (e.g., cholesterol and glucose) suspended in a liquid called plasma. Blood can be treated with an anticoagulant. Thus, the term "blood" includes, without limitation, whole blood treated with sodium citrate (an anticoagulant), platelet-rich plasma treated with citric acid, and packed red blood cells treated with heparin.

Whole blood can be processed to separate and collect individual components from the blood. For example, red and white blood cells can be removed, leaving the non-cellular components suspended in plasma. As described above, apheresis systems, such as plateletpheresis systems or plasmapheresis systems are commercially available and used to extract desired components (e.g., platelets or plasma) from whole blood from a donor. In some embodiments, the component-reduced blood is returned to the donor by the apheresis system.

Since all the blood-borne molecules (e.g., proteins, lipids, carbohydrates, etc.) not contained within cells and/or attached to the surface of cells are suspended in plasma, the plasma portion of blood will contain these molecules. The proteins in the plasma, which are referred to a blood plasma proteins or simply plasma proteins, are varied and have multiple roles. For example, all of the factors of the coagulation cascade (e.g., fibrinogen, plasminogen thrombin, Factor XIII, Factor IX, Factor VIII, and Factor V) are plasma proteins. Other plasma proteins include, without limitation, the complement proteins (e.g., complement component 3 and complement component 4), albumin, globulins (e.g., alpha 1 globulins and gamma globulins), C-reactive protein (CRP), lipoproteins (e.g., HDL, LDL), and various hormones and enzymes. Albumins account for 55% of blood plasma proteins, and fibrinogen comprises another 7%.

Thus, blood (e.g., whole blood or a blood product such as plasma) can be further processed to extract desired components from the blood. For example, an early method for processing blood plasma to enrich for albumin was developed by Edwin Cohn (see Cohn et al., J. Am. Chem. Soc. 68: 459-475, 1946). In this method, call the Cohn method, blood plasma was separated into five fractions by using different concentrations of ethanol (used as a protein precipitant) while changing the pH between 7.2 and 4.6 with various buffers to extract albumin.

Globulin proteins account for 38% of blood plasma proteins, and typically make up about 2.6 to about 4.6 grams per dL (deciliter). One type of globulin are gamma globulins, and these include immunoglobulins (also called antibodies). Although there are five isotypes of immunoglobulins in human (namely A, G, D, E, and M), the most prevalent form in blood is the G type (i.e., IgG), which accounts for approximately 75% of the immunoglobulins found in blood plasma. IgA and IgM also can be readily found in blood plasma. For healthy humans between the ages of about 19 years of age and about 55 years of age, the following amount of immunoglobulin can be found circulating in 1 deciliter of whole blood: 0.560 grams to 1.8 grams of IgG, 70 mg to 400 mg of IgA, and 40 mg to 250 mg of IgM.

Recently, it has been found that immunoglobulins can be given to a patient as a form of therapy. This type of therapy is called immunoglobulin therapy. The administration of immunoglobulins as a therapeutic agent can confer passive resistance to infection in the recipient patient. The immunoglobulin therapy can be administered by a variety of routes including intravenous, subcutaneous, and intramuscular. Immunoglobulin therapy is useful for administration to patients whose bodies cannot produce enough of its own immunoglobulin to maintain a healthy state. The immuno-globulin therapy may be temporary, to treat a particular disease or to temporarily boost the amount of immunoglobu-lin in the patient. In some embodiments, a patient may be need immunoglobulin therapy for their entire lives. Patients with diseases including primary immunodeficiency diseases (e.g., X-Linked Agammaglobulinemia (XLA) and Common Variable Immune Deficiency (CVID)), myasthenia gravis, infection with human immunodeficiency virus (HIV), auto-immune disorders (e.g., Guillain-Barre syndrome and Kawasaki disease), acute infections, and patients having received an organ transplant are included in a non-limiting list of patients who can benefit from immunoglobulin therapy.

In some embodiments, the immunoglobulins purified from the blood are further processed (e.g., frozen, stored, or pooled from multiple donors) prior to being administered to a recipient patient as a therapeutic. For example, the immu-noglobulin purified in accordance with a non-limiting embodiment of the present disclosure may be obtained from the whole blood of several donors. In a non-limiting example, the plasma can first be collected from several sources of whole blood, and the plasma pooled (i.e., com-bined). The immunoglobulin can then be purified from the pooled plasma. In another non-limiting example, the immu-noglobulin can be purified from an individual donor, and then the purified immunoglobulin from the first donor can be combined with (i.e., pooled) with the purified immuno-globulin from a second donor (and from a third donor, fourth donor, etc.). In some embodiments, the purified immuno-globulin can be further processed by being stored (e.g., at room temperature, at 4° C., or at −20° C.) prior to being used as a therapeutic.

As immunoglobulins, particularly IgG, are prevalent blood plasma proteins, in some embodiments, the invention is directed to isolating and purifying the immunoglobulin from blood (e.g., whole blood or a blood product such as plasma) collected from a donor. It should be noted that for therapy, IgG is preferred over a mixture of IgG with IgA and/or IgM. One non-limiting reason for this preference is that while IgG is a monomer (comprising four chains—two identical heavy chains and two identical light chains), IgA and IgM are not. Rather, IgA is a dimer, comprising four identical heavy chains and four identical light chains, and IgM is a pentamer, comprising ten identical heavy chains and ten identical light chains. As a result, IgA and IgM are more likely to clump, making them less desirable in a therapeutic composition.

By "purifying" is meant that the indicated protein (e.g., IgG) is at least 90%, or at least 92%, or at least 95% free, or at least 98% free of other molecules found in the biological fluid in which the protein naturally occurs. For example, if the protein is an immunoglobulin, a purified immunoglobulin is at least is at least 90%, or at least 92%, or at least 95% free, or at least 98% free of other blood proteins including, without limitation, cholesterol, albumin, complement proteins, and coagulation cascade proteins. If the protein is an IgG, a purified IgG is at least is at least 90%, or at least 92%, or at least 95% free, or at least 98% free of other blood proteins including, without limitation, IgA, IgM, cholesterol, albumin, complement proteins, and coagulation cascade proteins. Note that a purified protein (e.g., purified IgG) can be purified either by pulling or extracting the desired protein out of the biological fluid in which the desired protein naturally occurs, or by removing all the other, non-desired proteins and molecules out of the biological fluid in which the desired protein naturally occurs, thereby leaving only desired protein, thus purified by enrich-ment, in the biological fluid.

Note that all serum proteins are also plasma protein. Serum is the liquid that remains when whole blood coagu-lates. Thus, not all plasma proteins are serum proteins because they solidify during the coagulation process. How-ever, immunoglobulins do not solidify during coagulation and thus remain in the serum. It should be noted that although immunoglobulins do not solidify to form part of the clot during coagulation of blood, at least some of the immunoglobulins will get trapped in the blood clot as it forms. Thus, there are fewer immunoglobulins in serum than there are in plasma; nevertheless, the immunoglobulins in serum are still biologically functional (i.e., they are still able to bind to their specific antigen). In serum taken from a normal healthy human adult (e.g., an adult between the ages of about 18 years to about 50 years), approximately 1158+/− 305 mg of IgG is present in one deciliter of serum.

Thus, it is desirable to extract IgG from a biological fluid (e.g., from whole blood or a blood product such as plasma or serum) or enrich IgG in a biological fluid (e.g., plasma) in order to further process it for eventual use, for example, as a therapeutic. The Cohn method, being very successful for isolating albumin from the blood plasma, has been modified to purify immunoglobulin from blood. See Tanaka et al., Braz. J. Med. Biol. Res. (2000 January) 33(1):27-30; Bruck-schwaiger, L., U.S. Pat. No. 8,993,734; Bruckschwaiger, L., U.S. Patent Publication No. 2015-0133644). Other methods for isolating immunoglobulin (e.g., IgG) from blood (e.g., whole blood or blood plasma) have been developed. How-ever, none of the prior art methods has succeeded in extract-ing more than 50% of the IgG present in whole blood from the blood for blood product.

The present invention stems, in part, from the discovery of methods and devices for extracting more than 50% of immunoglobulin (e.g., IgG) present in a biological fluid from that biological fluid or enriching more than 50% of immunoglobulin (e.g., IgG) present in a biological fluid in that biological fluid. In some embodiments, more than 55% of immunoglobulin (e.g., IgG) present in a biological fluid is extracted from that biological fluid according to the methods described herein. In some embodiments, more than 55% of immunoglobulin (e.g., IgG) present in the biological fluid is enriched according to the methods described herein. The extracted or enriched immunoglobulin (e.g., IgG) can then be further purified and/or further processed.

In some embodiments, the invention provides methods and devices for extracting or enriching more than 55% of the IgG present in a biological fluid such as blood (e.g., whole blood or a blood product such as plasma or sera). In other words, when one deciliter whole blood from a normal adult human is processed using the methods described herein, at least about 0.35 grams to 0.8 grams of IgG is extracted or enriched from the whole blood. In some embodiments, the methods and devices extract or enrich more than 60% of the IgG present in a biological fluid. In some embodiments, the methods and devices extract or enrich more than 70% of the IgG present in a biological fluid. In some embodiments, the methods and devices extract or enrich more than 80% of the IgG present in a biological fluid. In some embodiments, the methods and devices extract or enrich more than 90% of the IgG present in a biological fluid. In some embodiments, the methods and devices extract or enrich more than 95% of the IgG present in a biological fluid. In some embodiments, the methods and devices extract or enrich more than 98% of the IgG present in a biological fluid. In some embodiments, the methods and devices extract or enrich more than 99% of the IgG present in a biological fluid.

Accordingly, in one aspect, the invention provides a method for enriching immunoglobulin such as IgG from an initial biological fluid, comprising obtaining an initial biological fluid suspected of containing immunoglobulin such as IgG and removing non-immunoglobulin (e.g., non-IgG) components naturally occurring in the initial biological fluid to obtain a non-immunoglobulin component-reduced biological fluid. In some embodiments, the method includes contacting the initial biological fluid with a solid support covalently bonded to a ligand that specifically binds to non-immunoglobulin components (or non-IgG components) under conditions sufficient for non-covalent binding of non-immunoglobulin component in the biological fluid to the ligand, and removing the bound non-immunoglobulin components to obtain a non-immunoglobulin component reduced biological fluid. In some embodiments, the non-immunoglobulin component-reduced biological fluid comprises at least 55% of immunoglobulin (e.g., IgG) present in the initial biological fluid.

In some embodiments, the non-IgG components comprise coagulation cascade proteins, lipids, carbohydrates, albumin, and complement proteins. In some embodiments, the immunoglobulin (e.g., IgG) in the non-immunoglobulin component-reduced biological fluid is purified.

In some embodiments, at least 60% of the immunoglobulin (such as IgG) present in the initial biological fluid is enriched from the initial biological fluid. In some embodiments, at least 70% of the immunoglobulin (such as IgG) present in the initial biological fluid is enriched. In some embodiments, at least 80% of the immunoglobulin (such as IgG) present in the initial biological fluid is enriched. In some embodiments, at least 85%, or at least 90%, or at least 95% of the immunoglobulin (such as IgG) present in the initial biological fluid is enriched from the initial biological fluid. In some embodiments, at least 98% of the immunoglobulin (such as IgG) present in the initial biological fluid is enriched from the initial biological fluid.

In some embodiments, the enriched from the initial biological fluid is selected from the group consisting of whole blood, platelet-rich plasma, plasma, and serum. In some embodiments, the enriched from the initial biological fluid is from a human.

In some embodiments, the amount (or concentration) of immunoglobulin (e.g., IgG) present in the biological fluid is measured prior to contacting the biological fluid with a solid support covalently bonded to a ligand that specifically binds to non-IgG blood components (or non-immunoglobulin blood components) under conditions sufficient for non-covalent binding of non-IgG blood component in the biological fluid to the ligand. In some embodiments, the amount (or concentration) of amount of immunoglobulin (e.g., IgG) present in the biological fluid is measured after the extraction of the non-IgG blood components.

The amount or concentration of immunoglobulin (e.g., IgG) present in the fluid (e.g., a biological fluid or an elution solution) can be determined by any standard method including ELISA, liquid or gas chromatography, mass spectrometry, nephelometry, etc. For example, the amount of immunoglobulin can be determined with a nephelometry assay using, for example, a BN-II device (Dade Behring, Marburg, Germany) according to manufacturer's instructions. The manufacturer indicates the following reference intervals for healthy human adults: IgA 70-400 mg/dl serum, IgG 700-1600 mg/dl serum and IgM 40230 mg/dl serum. Standard ELISA can also be used. See, e.g., Haroun and El-Sayed, J.

Clin. Biochem. Nutr. 40:56-61, 2007. Electrophoresis tests can also be used to determine the amount of immunoglobulin in a biological fluid.

In some embodiments, the remaining biological fluid after the non-immnoglobulin components have been extracted from it (which may be referred to as immunoglobulin-enriched biological fluid) is collected. The immunoglobulin-enriched biological fluid may be further processed (e.g., lyophilized, freezing, refrigerated, etc.).

In another aspect, the invention provides a method for extracting at least 55% of immunoglobulin (such as IgG) present in a biological fluid from the biological fluid comprising contacting a biological fluid suspected of containing immunoglobulin (such as IgG) with a solid support covalently bonded to a ligand that specifically binds to immunoglobulin (such as IgG) under conditions sufficient for non-covalent binding of IgG in the biological fluid to the ligand, and contacting the solid support with an elution solution under condition whereby the non-covalently bound immunoglobulin (such as IgG) is released from the ligand and into the elution solution, wherein at least 55% of the immunoglobulin (such as IgG) present in the biological fluid is extracted into the elution solution. In some embodiments, at least 60% of the immunoglobulin (such as IgG) present in the biological fluid is non-covalently bound to the ligand and thus extracted from the biological fluid. In some embodiments, at least 70% of the immunoglobulin (such as IgG) present in the biological fluid is non-covalently bound to the ligand and thus extracted from the biological fluid. In some embodiments, at least 80% of the immunoglobulin (such as IgG) present in the biological fluid is non-covalently bound to the ligand and thus extracted from the biological fluid. In some embodiments, at least 85%, or at least 90%, or at least 95% of the immunoglobulin (such as IgG) present in the biological fluid is non-covalently bound to the ligand and thus extracted from the biological fluid. In some embodiments, at least 98% of the immunoglobulin (such as IgG) present in the biological fluid is non-covalently bound to the ligand and thus extracted from the biological fluid.

In some embodiments, the amount (or concentration) of immunoglobulin (e.g., IgG) present in the biological fluid is measured prior to contacting the biological fluid with a solid support covalently bonded to either a ligand that specifically binds to IgG under conditions sufficient for non-covalent binding of IgG in the biological fluid to the ligand or a ligand that specifically binds to non-immunoglobulin components (e.g., albumin) under conditions sufficient for the non-covalent binding of the non-immunoglobulin component to the ligand. In some embodiments, the amount (or concentration) of immunoglobulin (e.g., IgG) present in the elution solution is measured after the elution of the ligand-bound IgG off the ligand and into the elution solution. In some embodiments, the amount (or concentration) of immunoglobulin (e.g., IgG) present in the biological fluid after removal of non-immunoglobulin components from the biological fluid.

The amount or concentration of immunoglobulin (e.g., IgG) present in the fluid (e.g., a biological fluid or an elution solution) can be determined by any standard method including ELISA, liquid or gas chromatography, mass spectrometry, nephelometry, etc. For example, the amount of immunoglobulin can be determined with a nephelometry assay using, for example, a BN™ II device (Dade Behring Holdings, Inc., Marburg, Germany) according to manufacturer's instructions. The manufacturer indicates the following reference intervals for healthy human adults: IgA 70-400 mg/dl serum, IgG 700-1600 mg/dl serum and IgM 40-230 mg/dl serum. Standard ELISA can also be used. See, e.g., Haroun and El-Sayed, J. Clin Biochem. Nutr. 40:56-61, 2007. Electrophoresis tests can also be used to determine the amount of immunoglobulin in a biological fluid.

In some embodiments, the remaining biological fluid after the immunoglobulin (e.g., the IgG isotype of immunoglobulin) has been extracted from it (which may be referred to as IgG-reduced or IgG-depleted biological fluid) is collected. In some embodiments, the IgG-depleted biological fluid is discarded. In some embodiments, the IgG-depleted biological fluid is not discarded and can be further processed to remove non-immunoglobulin components (e.g., albumin).

In some embodiments, the non-immunoglobin components removed from a biological fluid containing immunoglobulin (e.g., the IgG isotype of immunoglobulin) to enrich that immunoglobulin are discarded. In some embodiments, the non-immunoglobulin components removed from the biological fluid is not discarded. For example, albumin (a non-immunoglobulin component of blood) is itself valuable and may be saved for further processing for future use.

As used here, by "extracting" simply means that the extracted component (e.g., IgG or non-immunoglobulin component) is removed from the composition (e.g., biological fluid) containing the component. Using the methods described herein, the extraction may be by contacting a biological fluid with a solid support covalently bonded to a ligand that specifically binds the target component (e.g., IgG or albumin) under condition sufficient for the non-covalent binding of the target component to the ligand.

It should be noted that by "under conditions sufficient for non-covalent binding" simply means conditions under which the target component (e.g., an IgG molecule or a non-immunoglobulin component such as albumin) in the biological fluid being processed is able to non-covalently bind to a ligand that specifically binds that component. For example, in some embodiments where the ligand specifically binds to an IgG molecule, the ligand and the IgG molecule may be in a liquid (e.g., a biological fluid), and under conditions sufficient for non-covalent binding, the liquid is not moving (e.g., flowing) faster than the kon/koff value of the ligand and the IgG molecule, so that the IgG molecule can non-covalently bind to the ligand. In another example, the liquid may not be flowing at all, and the conditions sufficient for non-covalent binding are simply conditions that allow the ligand and the targeted component (e.g., an IgG molecule or albumin) to form a non-covalent bond with one another. Thus, conditions sufficient for non-covalent binding may include, without limitation, an appropriate flow speed of the liquid, an appropriate backpressure produced by the flow of the liquid through a container if the solid support to which the ligand is covalently attached is in the container, an appropriate temperature (e.g., between about 4° C. to 37° C., or between about 20° C. to about 25° C.), an appropriate pH (e.g., between about 6.5 and 8.5, or between about 7.0 and 8.0), and an appropriate osmolarity (e.g., isotonic or slightly hypotonic or hypertonic).

Likewise, by "under conditions whereby the non-covalently bound IgG is released from the ligand" simply means that the target component (e.g., an IgG molecule) non-covalently bound to the ligand can dissociate from the ligand and be released (i.e., eluted), for example, into an elution solution. For example, in some embodiments of conditions whereby the non-covalently bound IgG is released from the ligand, the elution solution is not moving (e.g., flowing) faster than the kon/koff value of the ligand and the IgG molecule, so that the IgG molecule can dissociate off the ligand and into the elution solution. In another example, the conditions whereby the non-covalently bound IgG is released from the ligand is simply an appropriate volume of the elution solution, an appropriate pH of the elution solution, and an appropriate concentration of osmolytes in the elution solution. For example, if the non-covalent bond between the IgG and the ligand is an ionic bond, the elution solution may have a high enough concentration of suitable ions (e.g., sodium ions and citrate ions) to compete with the ions in the ionic bond and thus break the bond. Thus, conditions whereby the non-covalently bound IgG is released from the ligand may include, without limitation, an appropriate flow speed of the elution solution, an appropriate backpressure produced by the flow of the elution solution through a container if the solid support to which the ligand is covalently attached is in the container, an appropriate temperature (e.g., between about 4° C. to 37° C., or between about 20° C. to about 25° C.) of the elution solution, an appropriate volume of the elution solution, an appropriate pH of the elution solution (e.g., between about 6.5 and 8.5, or between about 7.0 and 8.0), and an appropriate osmolarity of the elution solution.

As used herein, by the term "immunoglobulin" is meant a protein produced by B lymphocytes that is able to specifically bind to a target (called an antigen) via its antigen-binding domain. The term "immunoglobulin" is interchangeable with the term "antibody". An immunoglobulin has distinct regions, including the antigen-binding domain and a Fc domain that mediates interaction of the immunoglobulin with immune cells and other proteins in the immune system. For example, the Fc portion of IgE binds with high affinity to the Fc-epsilon receptor expressed on mast cells. There are five isotypes of immunoglobulins in human, namely IgA, IgD, IgE, IgG, and IgM. The most prevalent in type of immunoglobulin in blood plasma is IgG, which has four subclasses (i.e., IgG1, IgG2, IgG3, and IgG4). IgG (in its four subtypes) provides the majority of antibody-based immunity against invading pathogens, and is capable of crossing the placenta of a mother to give passive immunity to her fetus.

By the term "non-immunoglobulin" component or molecule is simply any substance in a biological fluid that is not an immunoglobulin. These non-immunoglobulins may be removed from the biological fluid, in some embodiments of the invention, to enrich for the immunoglobulin. Non-limiting non-immunoglobulin components include albumin, coagulation cascade proteins (e.g., Factor X, Factor VII), fibrinogen, hormones, insulin, lipids, vitamins, complement cascade proteins (e.g., complement component 3), and C-reactive protein.

As used herein, by "biological fluid" is meant any fluid that is derived from a vertebrate animal such as a human or a domesticated animal (e.g., cow, goat, sheep, and the like). Biological fluids include, without limitation, whole blood, components of whole blood (e.g., plasma and serum), saliva, milk, semen, tears, urine, and fluid from various organs such as bile fluid produced by the liver and lymph fluid (e.g., formed from interstitial fluid and collected in lymph capillaries). Since all of these biological fluids may contain IgG, these fluids may also be referred to as a biological fluid suspected of containing IgG.

"Whole blood" simply means blood as it is taken out of the patient or donor. Although compounds can be added to whole blood, no components that are in whole blood are removed from it. Components that can be added to whole blood include, without limitation, anticoagulants such as heparin or sodium citrate, and blood storage solutions and additive solutions described in, example, U.S. Pat. No.

8,709,707, and including CPD (citrate, phosphate and dextrose), ACD (acid citrate dextrose; commonly added during apheresis procedures), SOLX®. When a component (e.g., platelets or plasma) is removed from whole blood, that component may be referred to as a blood component, and the remaining blood components may be referred to as the "component-reduced" or "component-depleted" (e.g., platelet-reduced blood or Ig-reduced blood).

It should be noted that any of the above biological fluids that has been depleted of a component is considered a biological fluid as the term is used herein. Thus, one non-limiting example of a biological fluid is the fluid remaining in whole blood after platelets have been removed. This fluid (comprising red blood cells, non-platelet leukocytes, and plasma) is considered a biological fluid and may be referred to as "platelet-reduced blood" or "platelet-depleted blood". If a particular component is removed from whole blood, the remaining components are enriched. Thus, "platelet-rich plasma" is another biological fluid as the term is used herein. Another non-limiting biological fluid is red blood cell-depleted, leukocyte-depleted fluid that consists mainly of plasma, but still contains a few red blood cells and leukocytes. Another non-limiting biological fluid is serum (i.e., the liquid remaining after whole blood coagulates. Another non-limiting biological fluid is sperm-reduced semen (e.g., seminal fluid having a reduced number of sperm cells). Another non-limiting biological fluid is lipid-reduced milk (e.g., similar to skim milk).

In some embodiments, the biological fluid is whole blood or a component of whole blood such as plasma, platelet-rich plasma or serum. In some embodiments, the component of whole blood (e.g., plasma) is collected during apheresis from a donor.

Figure 2:
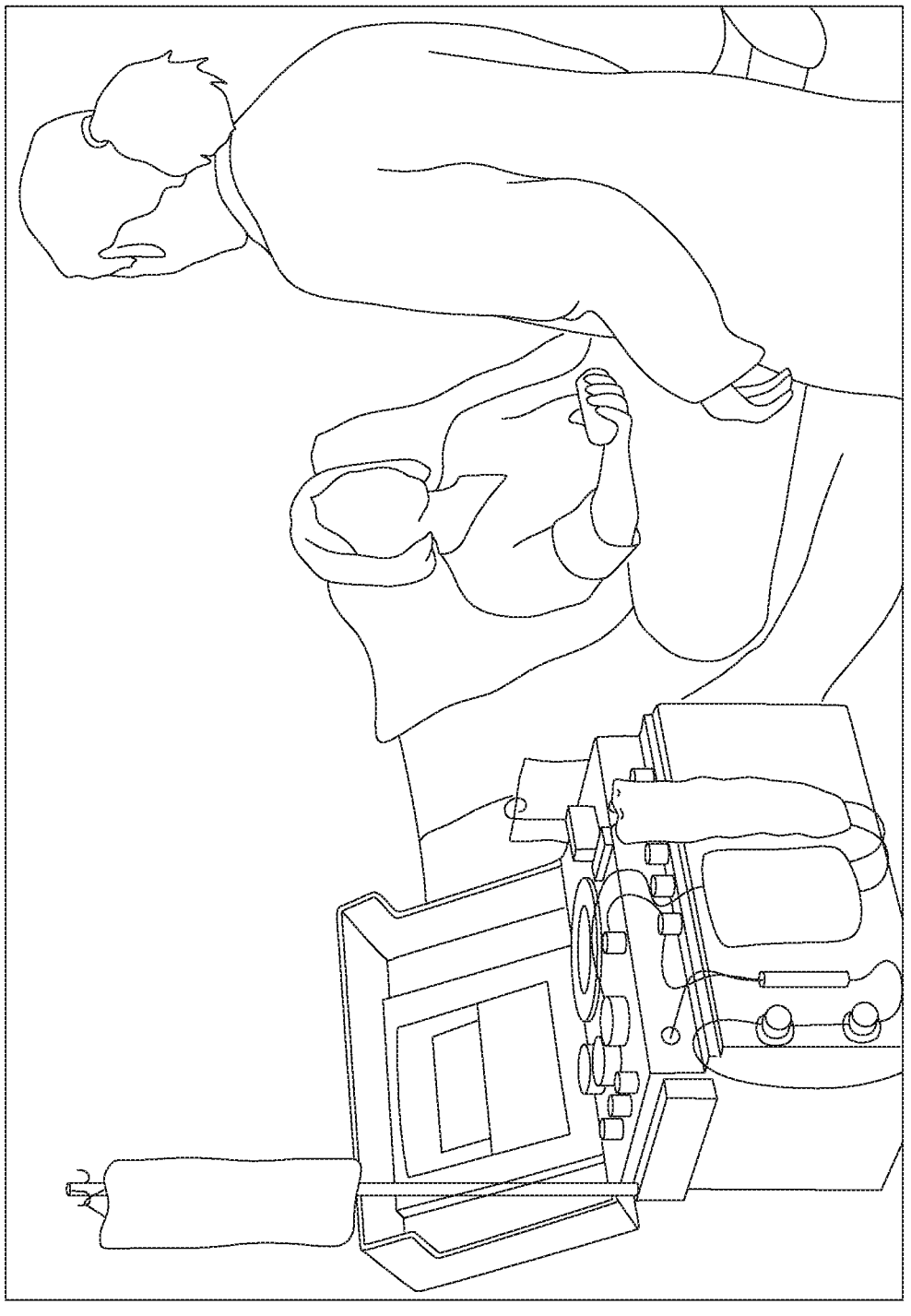
FIG. 2 is a photograph of a non-limiting representative apheresis machine, namely the MCS®+ 9000 mobile plate-let collection system machine sold by Haemonetics Corp. (Braintree, MA), in use. In this FIG. 2, the apheresis machine shown is being used to collect platelets.

For example, commercially available apheresis systems such as the MCS®+ 9000 mobile platelet collection system from Haemonetics Corp. (see FIG. 1) or the PCS®2 system from Haemonetics Corp. (see FIG. 2) are currently in used to isolate platelets and plasma, respectively. A blood component, such as plasma, can be collected during apheresis and immunoglobulin purified from the blood component accordingly.

By "ligand" is meant a molecule such as a protein (e.g., an antibody or bacterial protein), a carbohydrate, a sugar, or any organic or inorganic molecule that is covalently bonded to a solid support. In some embodiments, the covalent bond to the solid support is via a carboxyl group on the ligand. In some embodiments, the covalently attached ligand covers the surface of the solid support that comes into contact with the biological fluid suspected of containing immunoglobulin (i.e., the ligand coats the surface). In some embodiments, the covalently attached ligand covers only part of the surface of the solid support that comes into contact with the biological fluid suspected of containing immunoglobulin.

As used herein, by "solid support" means any type of solid, such as plastic, fibrous polymeric materials, polysaccharide, glass, or metal, in any shape including flat, round, spherical, concave, convex, etc. In some embodiments, the solid support can be rigid or can be flexible. In some embodiments, the solid support is flat or relatively flat. For example, the slid support may be a glass or plastic slide. Of course, where the solid support has two surfaces (e.g., a glass plate) and only one of the surfaces of the surface will be contacted with the biological fluid suspected of containing IgG, only the surface that will contact the biological fluid (or a part of that surface) is covalently attached to the ligand.

In some embodiments, the solid support is a fibrous polymeric material including without limitation, polyester fibers, polyurethane, a mixture of polypropylene oxide (PPO), polyethylene oxide (PEO), RCS media (a polymer blend of polyethylene oxide and polypropylene oxide), polyesters, and the like.

It should be noted that the type of covalent bond between the ligand and the solid support will depend upon the solid support being used, particularly the material at the surface of the solid support to which the ligand is covalently attached. For example, the solid support (or surface thereof) may be a LRFXL Layer #1, which is a material grafted (through radical polymerization technique) with high concentration of HEMA (Hydroxymethymethacrylate) and very low amount of MAA (Methacrylic Acid). The predominant functional groups in a solid support made of (or having a surface covered with) LRFXL Layer #1 are carboxyl groups with some smaller amounts of hydroxyl groups.

In another example, the solid support (or surface thereof) may be LRFXL Layer #9, which is a material grafted with high concentration of HEMA and lower amount of MAA. The predominant functional groups in a solid support made of (or having a surface covered with) LRFXL Layer #9 are carboxyl groups with some smaller amounts of hydroxyl groups.

In another example, the solid support (or surface thereof) may be WBF, which is a material that is gas-plasma treated with Argon and ammonia. The predominant functional groups in a solid support made of (or having a surface covered with) WBF are amines.

In yet another example, the solid support (or surface thereof) may be BPF4, which is a material grafted with high concentration of Methylmethacrylate (MMA) and low concentration of HEMA. The predominant functional groups in made of (or having a surface covered with) BPF4 are mostly hydroxyl groups with some smaller amounts of carboxyl groups.

U.S. Pat. No. 5,344,561 (herein incorporated by reference in its entirety) describes the chemistries in involved in LRXL Layer #1, LRFXL Layer #9, WBF, and BPF4. However, the routinely skilled person will readily understand that any solid support or surface can be used to covalently attach the ligand that is able to non-covalently specifically bind to an immunoglobulin. The above-listed examples of materials (e.g., LRXL Layer #1, LRFXL Layer #9, WBF, and BPF4) are non-limiting and any material (e.g., plastic, polymer, glass, metal, etc.) can be employed as a solid support in accordance with the present disclosure. See, for example, PCT Publication No. WO 2005/073711, PCT Publication No. Publication No. WO 2004/024318; U.S. Pat. Nos. 6,498,236, and 7,144,743, all of which are incorporated by reference herein in their entireties.

In some embodiments, the sold support may also be concave, such as the interior of the side or a column. In some embodiments, the solid support may be convex, such as the surface of a spherical bead (or a roughly spherical bead). Note that the solid support may be porous. For example, the solid support may be porous beads such that some of the solid support (e.g., on the surface of the bead) may be convex and some of the solid support (e.g., in a pore within the bead) may be concave.

In some embodiments, the solid support are beads. Non-limiting examples of beads are metal beads (e.g., magnetic beads), polymer beads (e.g., polystyrene beads or polypropylene beads), polysaccharide beads (e.g., cellulose beads or agarose beads), and other organic material beads (including starch beads, agar beads, dextran beads), and hydrophilic synthetic polymers, including substituted or unsubstituted polyacrylamides, polymethacrylamides, polyacrylates, polymethacrylates, polyvinyl hydrophilic polymers such as polyvinyl alcohol, polystyrene, polysulfone, and copolymers or styrene and divinylbenzene, and mixtures thereof. The beads themselves may also be porous. Other materials for solid supports such as beads are described in PCT Publication No, WO2012/118735, incorporated herein by reference in its entirety).

It will be understood the material of the beads (or of a non-bead solid support) may vary depending on how the biological fluid is processed to extract the immunoglobulin (such as IgG) or to extract the non-immunoglobulin component (e.g., albumin) from the biological fluid. For example, polystyrene beads (which are approximately 40 microns in diameter) are known to withstand a high flow rate which may be useful, for example, when the biological fluid is being pushed through the container (such as a bag or a column) containing the beads at a high flow rate. In some embodiments, the diameter of the beads is less than about 500 micrometers (um or "microns"). In some embodiments, the diameter of the beads ranges between about 30 microns to about 300 microns. In some embodiments, the diameter of the beads ranges between about 30 microns to about 150 microns. In some embodiments, the diameter of the beads ranges between about 35 microns to about 100 microns. In some embodiments, the diameter of the beads ranges between about 35 microns to about 75 microns. In some embodiments, the diameter of the beads ranges between about 40 microns to about 60 microns. Of course, where the solid support are beads, the diameter of the beads can be smaller than 35 microns and/or can be larger than 100 microns. The beads may be solid or may be porous. Regardless of whether the beads are solid or porous, the ligand may be covalently attached to part of the surface of the bead, or all of the surface of the bead. Likewise, for any solid support (e.g., glass plate), the ligand may be covalently attached to part of the surface of the solid support, or all of the surface of the solid support that will be in contact with a biological fluid suspected of containing immunoglobulin (e.g., IgG.)

In those embodiments wherein the beads, e.g., porous beads, may have a surface area of, for example, at least about 40 m 2/g to about 700 m 2/g, although in some embodiments, the surface area can be less than about 40 m 2/g or more than about 700 m 2/g. In some embodiments, the beads have a surface area of at least about 50 m 2/g.

In some embodiments, the solid support can be wetted before placing biological fluid in contact with the solid support, e.g., by wetting the solid support with a buffer (e.g., phosphate buffered saline (PBS), an antioxidant (e.g., to reduce oxidate damage to a desired component of the biological fluid, e.g., red blood cells, such as the N-Acetyl-Cysteine (NAC) antioxidant, for example, in the range of about 1 to about 50 nm), a red blood cell additive solution (e.g., one of the solutions described in U.S. Pat. No. 8,709, 707) and/or a platelet additive solution (see, e.g., U.S. Pat. Nos. 4,695,460; 4,447,415; Osselear et al., Transfusion 48: 1061-1071, 2008; Osselear et al., Vox Sang 94: 315-203, 2008).

It should be noted, where all or most (e.g., at least about 75% or more) of the surface of the solid support that will be in contact with a biological fluid suspected of containing immunoglobulin (e.g., IgG) is covalently bonded to ligand, the solid support may be referred to as being coated with the ligand. It will be understood that solid support (e.g., a bead) coated with a ligand means that the ligand is covalently bound (i.e., covalently attached) to the surface of the solid support that will be in contact with a biological fluid suspected of containing immunoglobulin such as IgG.

In some embodiments, the solid support covalently bonded to a ligand that specifically binds to immunoglobulin (e.g., IgG) or that specifically binds to a non-immunoglobulin component (e.g., albumin) may be in a container. Suitable containers include bags, columns, boxes, tubes, etc. The container may have an inlet opening for admitting a biological fluid suspected of containing immunoglobulin and an outlet opening for releasing immunoglobulin-depleted (or reduced) biological fluid after contact of the biological fluid with the solid support in the container. In some embodiments, the solid support is the internal surface of the container that is in contact with the biological fluid suspected of containing immunoglobulin. In some embodiments, the solid support is beads (e.g., magnetic beads or polymer beads) that are covalently attached to the ligands that specifically bind to immunoglobulin such as IgG.

Thus, in another aspect, the invention provides a container comprising a solid support covalently bonded to a ligand that specifically binds to IgG, wherein the container is configured for use in an apheresis system (or apheresis machine). In some embodiments, the container is a column. In some embodiments, the container is a bag.

In some embodiments, the solid support covalently bonded to a ligand that specifically binds to a non-IgG component (e.g., albumin or Factor IX) may be in a container. Suitable containers include bags, columns, boxes, tubes, etc. The container may have an inlet opening for admitting a biological fluid suspected of containing immunoglobulin and an outlet opening for releasing non-IgG-depleted (or reduced) biological fluid after contact of the biological fluid with the solid support in the container. In some embodiments, the solid support is the internal surface of the container that is in contact with the biological fluid suspected of containing immunoglobulin. In some embodiments, the solid support is beads (e.g., magnetic beads or polymer beads) that are covalently attached to the ligands that specifically bind to non-IgG components (e.g., the ligand may be an albumin-specific antibody).

Thus, in yet another aspect, the invention provides a container comprising a solid support covalently bonded to a ligand that specifically binds to non-IgG components. In some embodiments, the container is configured for use in an apheresis system (or apheresis machine). In some embodiments, the container is a column. In some embodiments, the container is a bag.

By "configured for use in an apheresis machine or system" simply means that the container has openings that are compatible with the tubing and adaptors in the system and thus can be used "in-line" in the system. In other words, "configured" simply means that the indicated object (e.g., a column or bag) is adapted or modified in some way to serve a purpose. For example, when a container is configured to work with a PCS®2 plasmapheresis machine, it simply means that the container is adapted to connect to the PCS®2 plasmapheresis machine, for example, by having an input port and an output port of the column modified with adaptors (e.g., leur lock adaptors) that are connectable to adaptors on the PCS®2 plasmapheresis machine. However, it should be understood that this container can work with any apheresis machine or system.

Figure 10A:
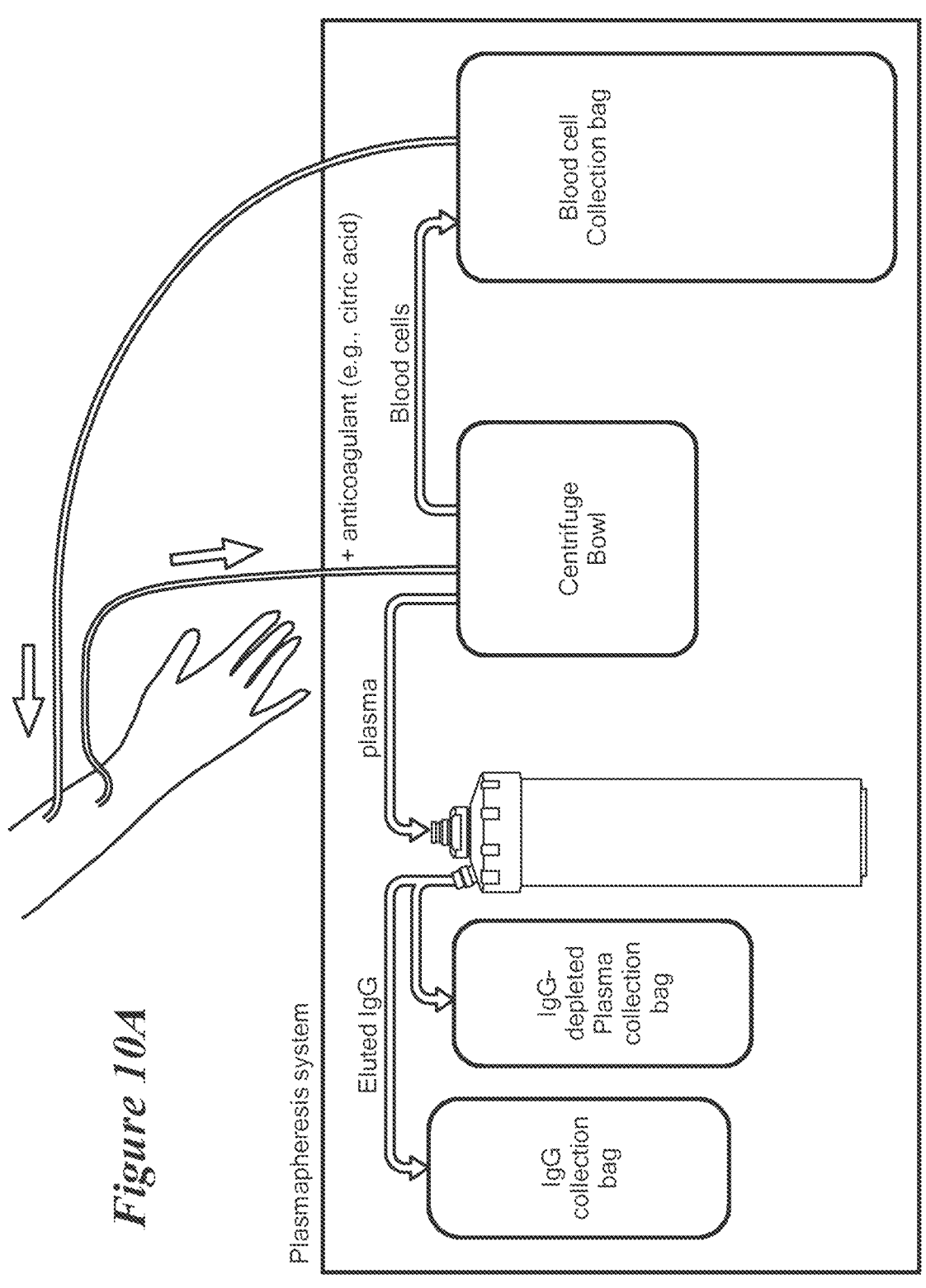
FIGS. 10A and 10B are schematic representations of modifications to a plasma pheresis system, such as the PCS®2 system (FIG. 10A) and to a platelet pheresis system, such as the MCS®+9000 system (FIG. 10B) to incorporate a radial column, a non-limiting example of a container comprising a solid support covalently linked to a ligand that specifically binds immunoglobulin.

For example, the inlet and outlet openings of the container may be adapted with leur lock adaptors to admit tubing used in the apheresis system. In one non-limiting example, in the PCS®2 plasmapheresis system sold by Haemonetics Corp. (Braintree, Massachusetts, USA), blood-compatible tubing connects the centrifuge bowl to the plasma collection bag. A container comprising a solid support covalently bound to a ligand that specifically binds to an immunoglobulin (such as IgG) or covalently bound to a ligand that specifically binds to a non-immunoglobulin component (such as albumin) may be connected to the tubing such that the tubing from the centrifuge bowl is attached to the inlet opening of the container and the tubing from the plasma collection bag is attached to the outlet opening of the container. One schematic showing such a connection is depicted in FIG. 10A. The container is thus "in-line" or "on-line" with the other components of the system, such that fluid exiting one component of the system (e.g., the centrifuge bowl) can enter the container without being exposed to conditions not within the closed system. This will prevent loss of sterility of the biological fluid and the other fluids in the system (e.g., anticoagulation fluid, elution solution, etc.).

It should be noted that the term "closed", in reference to a system, system that allows the collection and processing (and, if desired, the manipulation, e.g., separation of portions, separation into components, filtration, storage, and preservation) of a biological fluid (e.g., donor blood, blood samples, and/or blood components), without the need to compromise the sterile integrity of the system. A closed system can be as originally made, or result from the connection of system components using sterile docking devices (see, e.g., U.S. Pat. Nos. 4,507,119, 4,737,214, and 4,913,756, each of which is incorporated herein in its entirety).

Thus, in yet another aspect, the invention provides an apheresis system configured to extract at least 55% of immunoglobulin (e.g., IgG) present in a biological fluid, the system comprising a container comprising a solid support covalently bonded to a ligand that specifically binds to immunoglobulin (e.g., IgG), in a method (e.g., a partially automated for a fully automated method) comprising (a) contacting a biological fluid suspected of containing immunoglobulin (e.g., IgG), with the solid support in the container under conditions sufficient for non-covalent binding of immunoglobulin (e.g., IgG) to the ligand; and (b) contacting the solid support in the container with an elution solution under condition whereby the non-covalently bound immunoglobulin (e.g., IgG) is released from the ligand and into the elution solution to obtain elution solution comprising immunoglobulin (e.g., IgG).

In another aspect, the invention provides an apheresis system configured to enrich at least 55% of immunoglobulin (e.g., IgG) present in a biological fluid, the system comprising a container comprising a solid support covalently bonded to a ligand that specifically binds to a non-immunoglobulin component (such as albumin), in a method (e.g., a partially automated for a fully automated method) comprising (a) contacting a biological fluid suspected of containing immunoglobulin (e.g., IgG), with the solid support in the container under conditions sufficient for non-covalent binding of the non-immunoglobulin component to the ligand; and (b) collecting the non-immunogloblulin depleted biological fluid from the container, the non-immunoglobulin depleted biological fluid being enriched for immunoglobulin (e.g., IgG).

In some embodiments, the container is a column. In some embodiments, the container is a bag.

In various embodiments, one or both of the container and the apheresis system is configured to support a fluid passing through the container (e.g., a column or bag) at a flow rate of between about 50 ml/minute to about 150 ml/minute. For example, the flow rate of a fluid passing through the container may be between about 60 ml/minute to about 130 ml/minute In some embodiments, one or both of the container and the apheresis system is configured to support a biological fluid passing through the container (e.g., a column or bag) with a backpressure of between about 5 mm Hg to about 300 mmHg. For example, the backpressure may be between about 10 mm Hg to about 150 mm Hg, or between about 10 mm Hg to about 120 mmHg, or between about 10 mmHg to about 100 mmHg, or between about 30 mm Hg to about 120 mmHg, or between about 50 to about 100 mmHg.

In some embodiments, the apheresis systems are configured to extract or enrich at least 55% of immunoglobulin such as IgG present in a biological fluid. In some embodiments, the apheresis systems are configured to extract or enrich at least 60% of immunoglobulin such as IgG present in a biological fluid. In some embodiments, the apheresis systems are configured to extract or enrich at least 70% of immunoglobulin such as IgG present in a biological fluid. In some embodiments, the apheresis system is configured to extract or enrich at least 80% of immunoglobulin such as IgG present in a biological fluid. In some embodiments, the apheresis system is configured to extract or enrich at least 90% of immunoglobulin such as IgG present in a biological fluid. In some embodiments, the apheresis system is configured to extract or enrich at least 95% of immunoglobulin such as IgG present in a biological fluid. In some embodiments, the apheresis system is configured to extract or enrich at least 98% of immunoglobulin such as IgG present in a biological fluid.

In some embodiments, the inlet opening of the container is adapted (e.g., configured) to include a filter with a pore size small enough to block the entrance into the container of a nucleated blood cell (e.g., an immature red blood cell or a monocyte). In some embodiments, the outlet opening of the container is adapted (e.g., configured) to include a filter with a pore size small enough to block the release from the container of a nucleated blood cell (e.g., an immature red blood cell or a monocyte). In some embodiments, where the solid support are beads covalently attached to the ligands that specifically bind to immunoglobulin, one or both of the inlet or outlet openings of the container are configured to include a filter with a pore size small enough to block release of the beads.

Note that to block a cell (e.g., a nucleated white blood cell), the pore size of a filter may be smaller than the average diameter of a cell. The average diameter of a monocyte, the largest white blood cell circulating in whole blood, is 15 um to about 30 um. Therefore, to block passage of a monocyte into a container, a filter may have a pore size that is smaller than 15 um in diameter (e.g., a pore size of between about 10-12 um). Of course, if cells smaller than a monocyte (e.g., a platelet, which has an average diameter of 2-3 um) are desired to be blocked from entering or exiting the container, the inlet or outlet, respectively, of the container may be adapted to include a filter having a pore size of 1 um diameter or less (e.g., a pore size of between 0.1 um to 1.0 um).

By "specifically binds" is meant that the ligand non-covalently binds to a particular target (e.g., an immunoglobulin such as an IgG molecule or a non-immunoglobulin such as an albumin molecule) with equilibrium dissociation constant (kD) of less than about $5 \times 10\text{-}8$ (i.e., 50 nM), less than about $1 \times 10\text{-}8$ (i.e., 10 nM), or less than about $5 \times 10\text{-}9$ (i.e., 5 nM), or less than about $1 \times 10\text{-}9$ (i.e., 1 nM). The specific binding of the ligand to its target (e.g., an immunoglobulin) can be on any portion of the target molecule (e.g., the Fc domain of the immunoglobulin or the antigen-binding domain of the immunoglobulin). In some embodiments, the ligand non-covalently specifically binds to the constant domain of the heavy chain of an immunoglobulin.

In some embodiments, the ligand non-covalently specifically binds to the Fc domain of an immunoglobulin.

In some embodiments, the ligand is an antibody that specifically binds to an immunoglobulin, specifically binds to a particular isotype of immunoglobulin (e.g., specifically binds to human IgG or human IgM) or specifically binds to a particular non-IgG or non-immunoglobulin blood component such as albumin. Other blood components that are non-IgG or non-immunoglobulin components include, without limitation, C-reactive protein, transferrin, complement proteins (e.g., complement component 3), prothrombin, blood clotting factors (e.g., Factor VIII, fibronectin, von Willibrand factor) and non-proteins including lipids and cholesterol.

In some embodiments, the ligand is cibacron blue, or a derivative thereof that can specifically bind to albumin.

Beads covalently bonded to cibacron blue are commercially available.

Figure 5:
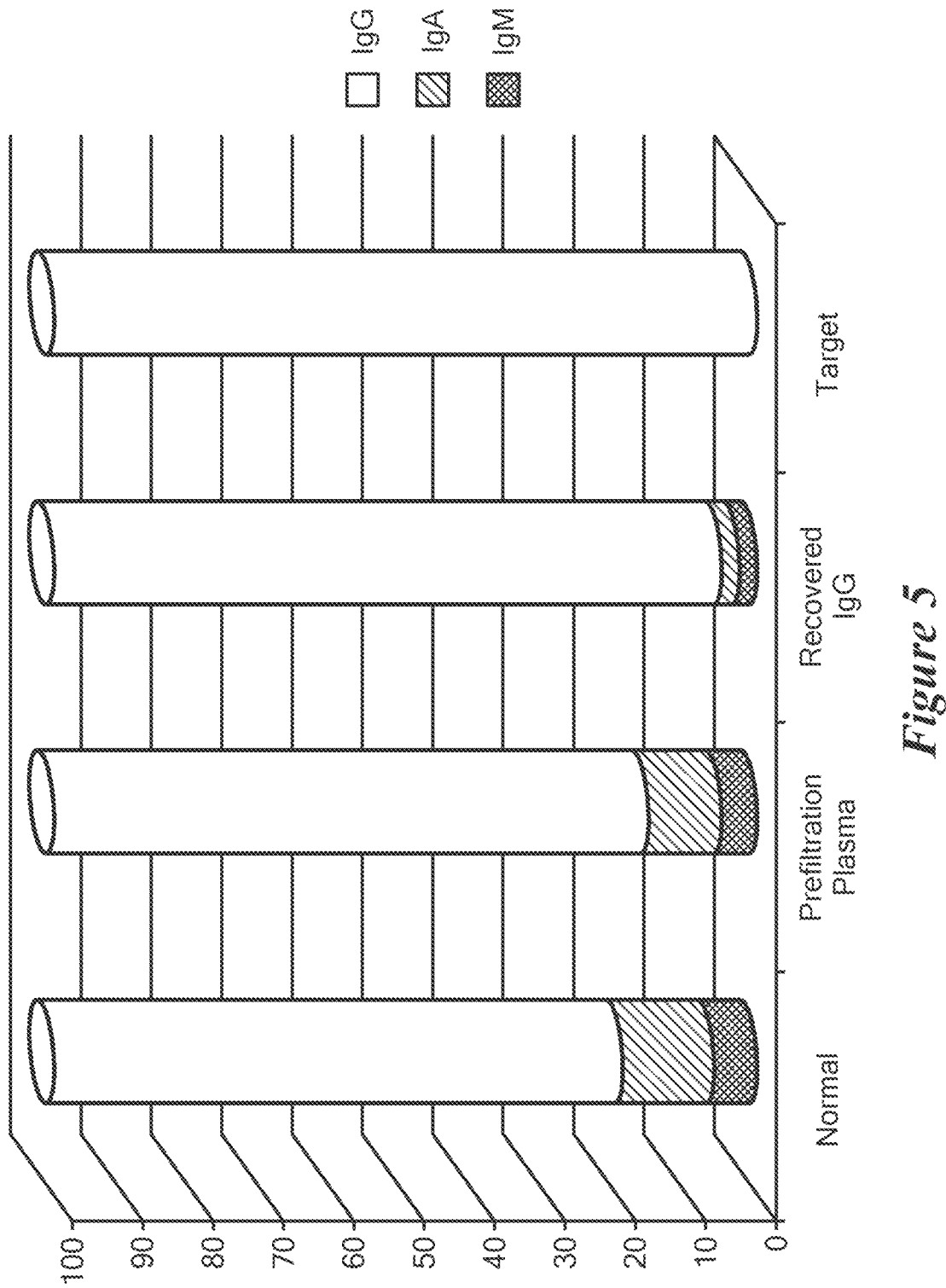
FIG. 5 is a bar/column graph showing the relative amounts of IgA, IgM, and IgG in normal human plasma (left column), the relative amounts of IgA, IgM, and IgG in human plasma collected in plasmapheresis (second from left column), the relative amounts of IgA (middle bar on "nor-mal" column), IgM (lowest bar on "normal" column, and IgG (highest bar on "normal" column) recovered from human plasma collected in accordance with a non-limiting embodiment of the invention as described below in Example 4 ("recovered IgG", third from left column), and the target goal of all IgG with no IgA or IgM (far right "target" column). Note that the target column has only IgG.

IgG is more prevalent in blood than other immunoglobulin isotypes including IgA and IgM. This enrichment is shown schematically in FIG. 5. The far left column (i.e., "normal") in FIG. 5 shows the typical percentages of IgG (green), IgA (red) and IgM (blue) in one liter of plasma as described in the scientific literature. Following plasma pheresis (e.g., using the PCS®2 machine sold by Haemonetics), the amount of IgA and IgM in the total immunoglobulin population is slightly decreases, likely because the IgA and IgM are clumping and thus are being separated out of the plasma and remain in the plasma-reduced blood that will be returned to the patient (see "prefiltration plasma" column in FIG. 5).

In some embodiments, the ligand is a protein from a bacterium, or is derived from such a protein. In some embodiments, where the target molecule is an immunoglobulin the ligand is a protein from a bacteria selected from the group consisting of *Staphylococcus* or *Streptococcus*, or a derivative thereof. In some embodiments, where the target molecule is a non-immunoglobulin molecule (e.g., albumin), the ligand may be cibacron blue.

In some embodiments, the ligand is protein A, or a derivative thereof that can specifically bind to IgG. Protein A is a five-domain protein of *Staphylococcus aureus* that is displayed on the surface of the bacterium, where each of the five domains can specifically bind to an immunoglobulin. Protein A preferentially specially binds to an IgG immunoglobulin in the Fc region, for example. Since protein A has five domains, each of which can specifically bind to an IgG molecule, a single domain (or a derivative or recombinant version thereof) can serve as a non-limiting ligand so long as it specifically binds to an immunoglobulin. Thus, the term "derivative of Protein A" includes derivatives of full length protein A, derivatives of one of the five domains of protein A, and derivatives of recombinant versions of full length protein A or a domain of protein A as long as the derivative of Protein A is able to specifically bind to IgG.

In some embodiments, the ligand is protein G, or a derivative thereof that can specifically bind to IgG. Protein G is expressed in group C and group G Streptococcal bacteria. In some embodiments, if protein G is used as the ligand, the native protein G is modified to remove the albumin-binding domain from protein G. Thus, the term "derivative of Protein G" includes derivatives of full length protein G and derivatives of recombinant or modified versions of protein G lacking the albumin-binding domain, as long as the derivative of Protein G is able to specifically bind to IgG.

Beads covalently bonded to protein A and/or protein G are commercially available. For example, Merck KGaA (Billerica, Massachusetts) sells a product, Eshmuno® A media, that is a resin of polyvinylether-based beads (of approximately 50 μm in diameter) covalently bonded to (i.e., covalently linked to) a pentameric form of recombinant domain C of *Staphylococcus aureus*. Likewise, ThermoFisher Scientific Inc. (Waltham, Massachusetts) sells a product, namely POROS™ MabCapture™ A media, that comprises beads of approximately 45 um diameter covalently bonded to recombinant Protein A.

Figure 4:
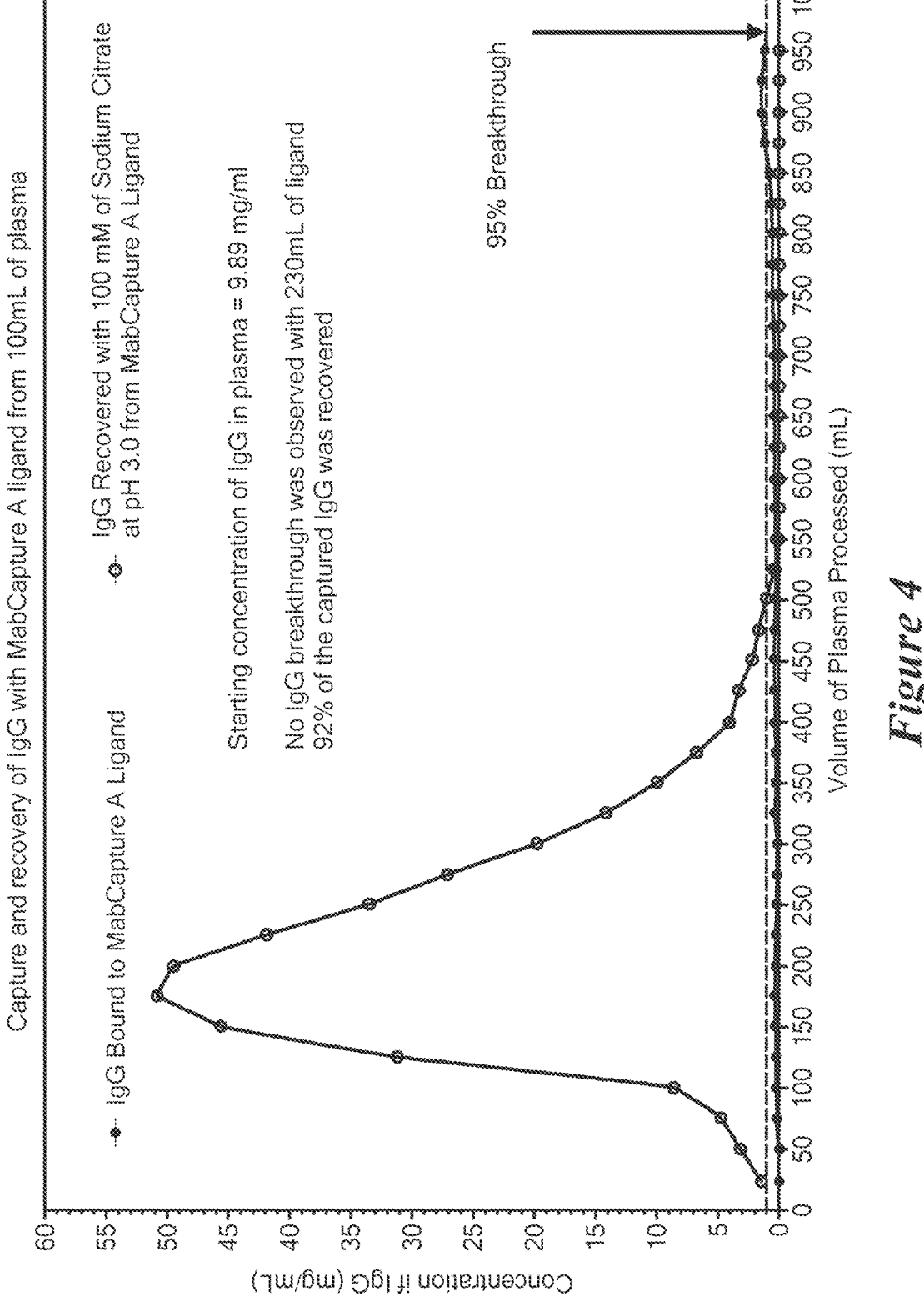
FIG. 4 is a line graph showing a representation of the amount of IgG that is recoverable from 1 liter (i.e., 1000 mL) of plasma using MabCapture™ A media beads, a non-limiting type of ligand covalently linked to a solid support.

For example, the MacCapture A ligand is highly efficient at capturing IgG from plasma, and such captured IgG is easily recovered. As shown in FIG. 4 and described in more detail in Example 1 below, 1000 ml of plasma (containing 9.89 mg/ml of IgG) was passed over a column containing 230 mL of MabCapture A media (i.e., comprising protein A-coated beads of approximately 45 um in diameter). As can be seen from the red line in FIG. 4, the IgG bound to the MabCapture A beads does not reach the binding capacity of the beads, and in fact does not reach the 95% capacity of the beads (see arrow for 95% breakthrough). Eluting the IgG off the beads using a 100 mM sodium citrate solution at a pH of 3.0 (a non-limiting elution solution of the invention) recovered 92% of the IgG captured by the MabCapture A beads (see green line in FIG. 4).

The use of protein A-coated beads has been found to significantly enrich IgG over IgA and IgM. This enrichment is shown schematically in FIG. 5. The far left column (i.e., "normal") in FIG. 5 shows the typical percentages of IgG (green), IgA (red) and IgM (blue) in one liter of plasma as described in the scientific literature. Following plasma pheresis (e.g., using the PCS®2 machine sold by Haemonetics), the amount of IgA and IgM in the total immunoglobulin population is slightly decreases, likely because the IgA and IgM are clumping and thus are being separated out of the plasma and remain in the plasma-reduced blood that will be returned to the patient (see "prefiltration plasma" column in FIG. 5). As described below in Example 4, plasma contacted with protein A coated beads (e.g., MabCapture A beads) and then eluted with 100 mM sodium citrate greatly reduces the amount of IgA and IgM in the eluted (i.e., recovered) Ig population (see "recovered IgG" column in FIG. 5). Ultimately, the target (depicted in the far right column in FIG. 5) has no IgA or IgM.

By "purified" as in "purified IgG", means that the IgG is at least 90% free (by weight) of non-IgG immunoglobulin (e.g., 90% free of IgA and IgM). In some embodiments, purified IgG means that the IgG is at least 92% free (by weight) of non-IgG immunoglobulin. In some embodiments, purified IgG means that the IgG is at least 95% free (by weight) of non-IgG immunoglobulin. In some embodiments, purified IgG means that the IgG is at least 97% free (by weight) of non-IgG immunoglobulin. In some embodiments, purified IgG means that the IgG is at least 99% free (by weight) of non-IgG immunoglobulin. Note that a non-IgG immunoglobulin is simply an immunoglobulin of a serotype other than IgG. Non-limiting non-IgG immunoglobulins are IgA, IgM, IgD, and IgE.

It should be understood that while protein A is exemplified in some embodiments herein, protein A is simply a non-limiting example of a ligand. Another non-limiting example of a ligand for use in the embodiments described herein is cibacron blue. Other ligands such as Melon™ gel (e.g., a proprietary chemical sold by Thermo Fisher Inc., Waltham, Massachusetts, USA), protein G, camelid antibodies, monoclonal and polyclonal antibodies (e.g., a mouse anti-human antibody), and mixed mode ligands such as mercaptoethyl-pyridine (MEP) are also contemplated.

It should be noted that the results of FIG. 4 and FIG. 5 were obtained from 1000 ml of plasma. Plasma can be obtained from standard apheresis systems.

Figure 6A:
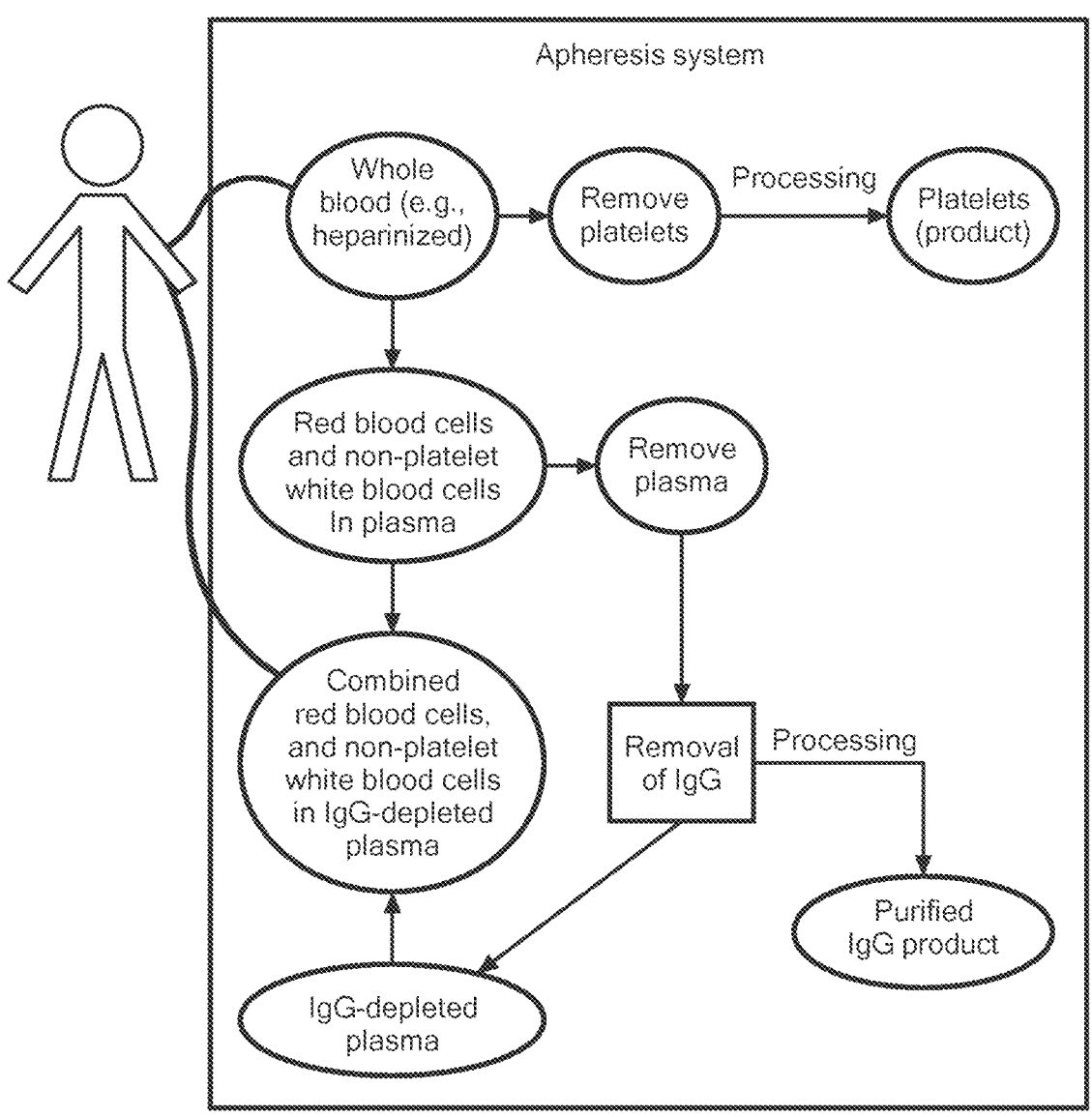
FIGS. 6A-6C is a schematic diagrams showing how apheresis systems can be modified to incorporate a step (e.g., a device) for removing IgG from a biological fluid taken from a patient (e.g., a healthy volunteer donor).

For example, in FIG. 6A, purified immunoglobulin can be obtained from a patient (or donor) undergoing plateletpheresis (e.g., using a MCS®+ 9000 machine). As shown in FIG. 6A, once the platelets are removed, the remaining blood components (e.g., red blood cells, non-platelet white blood cells, and plasma) can be further processed (e.g., by centrifugation or filtering) to remove the plasma. The IgG can be separated from the plasma and further processed (e.g., by freezing or lyophilizing) to result in a purified IgG product. The remaining Ig-depleted plasma (which, of course, may still have some Ig in it, and so could also be called "Ig-reduced plasma") can be saved, discarded, or, as is depicted in FIG. 6A, mixed with the red blood cells and non-platelet white blood cells and returned to the patient (or donor).

It should be noted that the solid surface covalently bonded to a ligand may be incorporated into the apheresis process itself. For example, in the method schematically depicted in FIG. 6A, the removal of IgG step (i.e., the extraction step) can be performed by a contacting the plasma with a container comprising a solid support covalently bonded to a ligand that specifically binds to IgG to remove the IgG from the plasma, where the container is itself part of the apheresis system. The elution of the IgG from the ligand can take place while the container is still attached to the apheresis system (e.g., via blood compatible tubing) and thus is still "on-line" or the container can be taken "off-line" and detached from the system prior to eluting the IgG from the ligand. The eluted IgG can then be further processed to result in a purified IgG product.

Figure 6B:
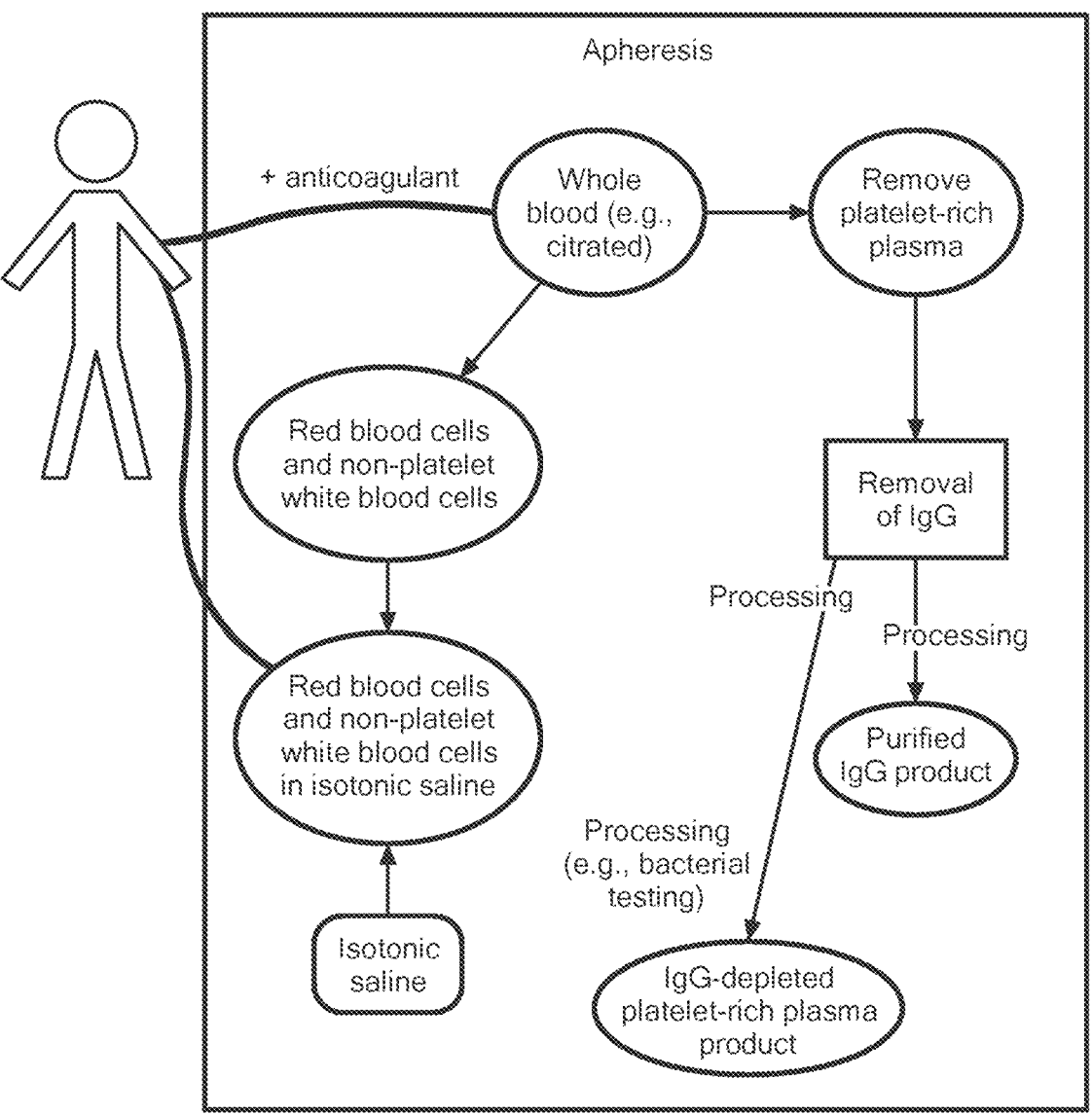

In another example, immunoglobulin can be purified and/or enriched from platelet-rich plasma. Although FIG. 6B depicts obtaining purified IgG from a patient (or donor) undergoing apheresis where platelet-rich plasma (PRP) is produced, it should be noted that the patient can simply donate whole blood, from which PRP is produced. In other words, no portion or component of the patient's whole blood following extraction of the PRP needs to be returned to the patient. Various instruments are capable of producing PRP including Biomet GPS GPS® II and III (Zimmer, Biomet, Warsaw, Indiana, USA) and Harvest SmartPrep® Multicellular Processing System (Lakewood, Colorado, USA). Of course, standard laboratory methods are also available to produce PRP. See, for example, Dhurat and Sukesh et al., J. Cutan. Aesthet. Surg. 7(4): 189-197, 2014. Apheresis systems such as the MCS®+ 9000 machine are also capable of producing platelet-rich plasma, and returning the non-platelet cells (such as red blood cells) to the patient donor. In the non-limiting chair-side method depicted in FIG. 6B, immunoglobulin such as IgG can be extracted from the platelet-rich plasma. After further processing (e.g., freezing), the purified IgG product results. The immunoglobulin-depleted platelet rich plasma can then be further processed (e.g., filtered, tested for bacteria, refrigerated, etc.) to product an Ig-depleted platelet-rich plasma product, and isotonic saline mixed with the non-platelet cells to return these cells to the patient (see FIG. 6B). In this scenario, where immunoglobulin is extracted from a biological fluid containing cells (i.e., the immunoglobulin is being extracted from PRP), the container comprising a solid support covalently bonded to a ligand that specifically binds to IgG that is used to extract the IgG may be structured so that the platelet cells in the PRP do not clog the container. For example, a bag, where the solid support covalently bonded to the ligand is the internal surface of the sides of the bag, may be employed. Another such container may be a column with beads having a diameter of at least 20 µm, where the beads are the solid support to which the ligand is covalently bonded. As platelets are only about 2-3 um in diameter, the platelets will be able to flow between the beads without clogging the column.

Figure 6C:
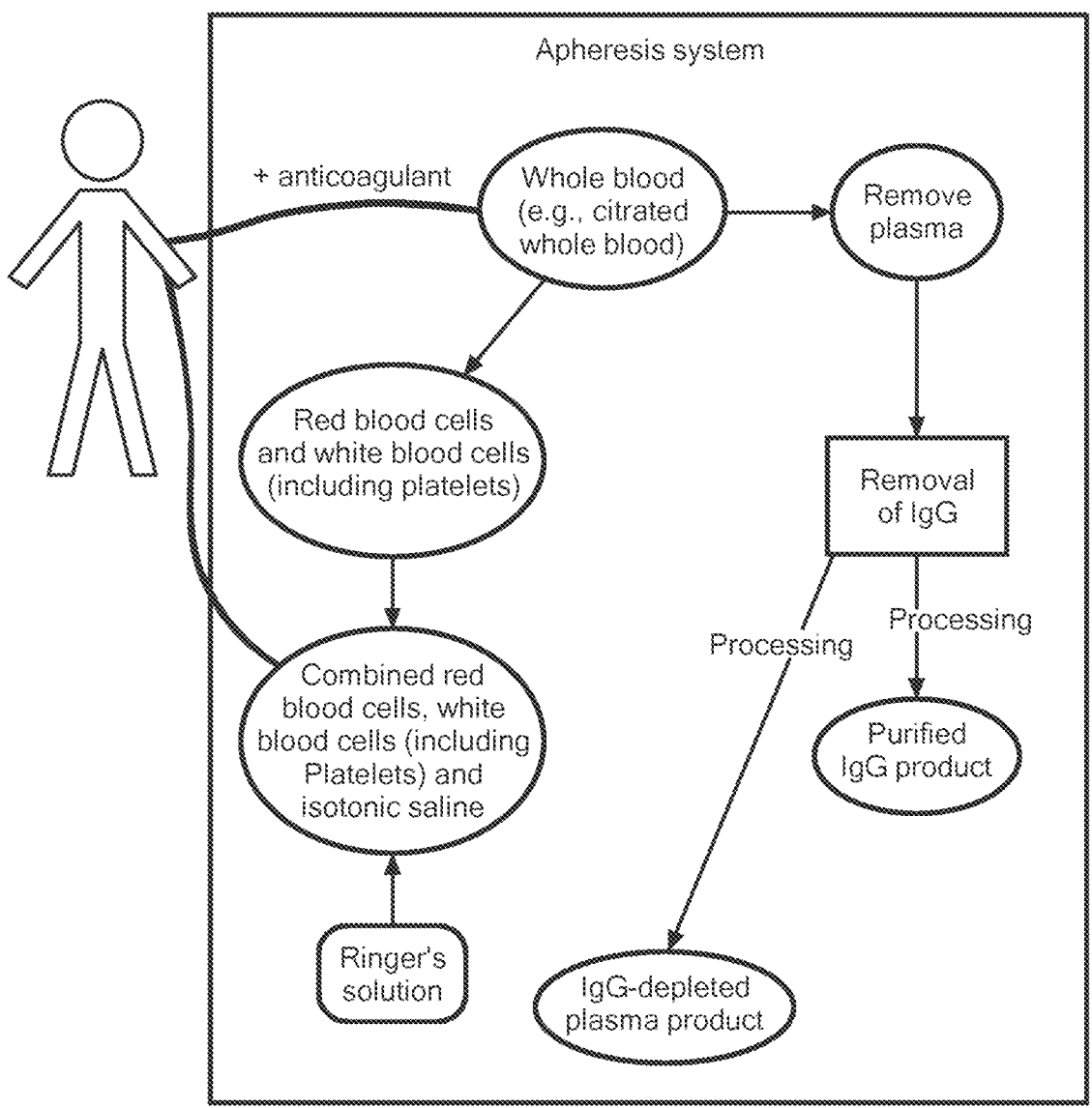

In yet another example, purified immunoglobulin can be obtained from a patient (or donor) undergoing plasmapheresis (e.g., using a PCS®2 machine). As shown in non-limiting example in FIG. 6C where IgG is extracted, once the plasma is removed from donor whole blood, the IgG can be separated from the plasma, and the Ig-reduced plasma can be discarded, mixed with the red blood cells and white blood cells (including platelets) and returned to the patient (or donor), or, as depicted in FIG. 6C, further processed (e.g., by filtering or testing for presence of bacteria) to produce an IgG-depleted plasma product. The IgG extracted from the plasma can be further processed (e.g., freezing) to result in a purified IgG product.

Figure 7:
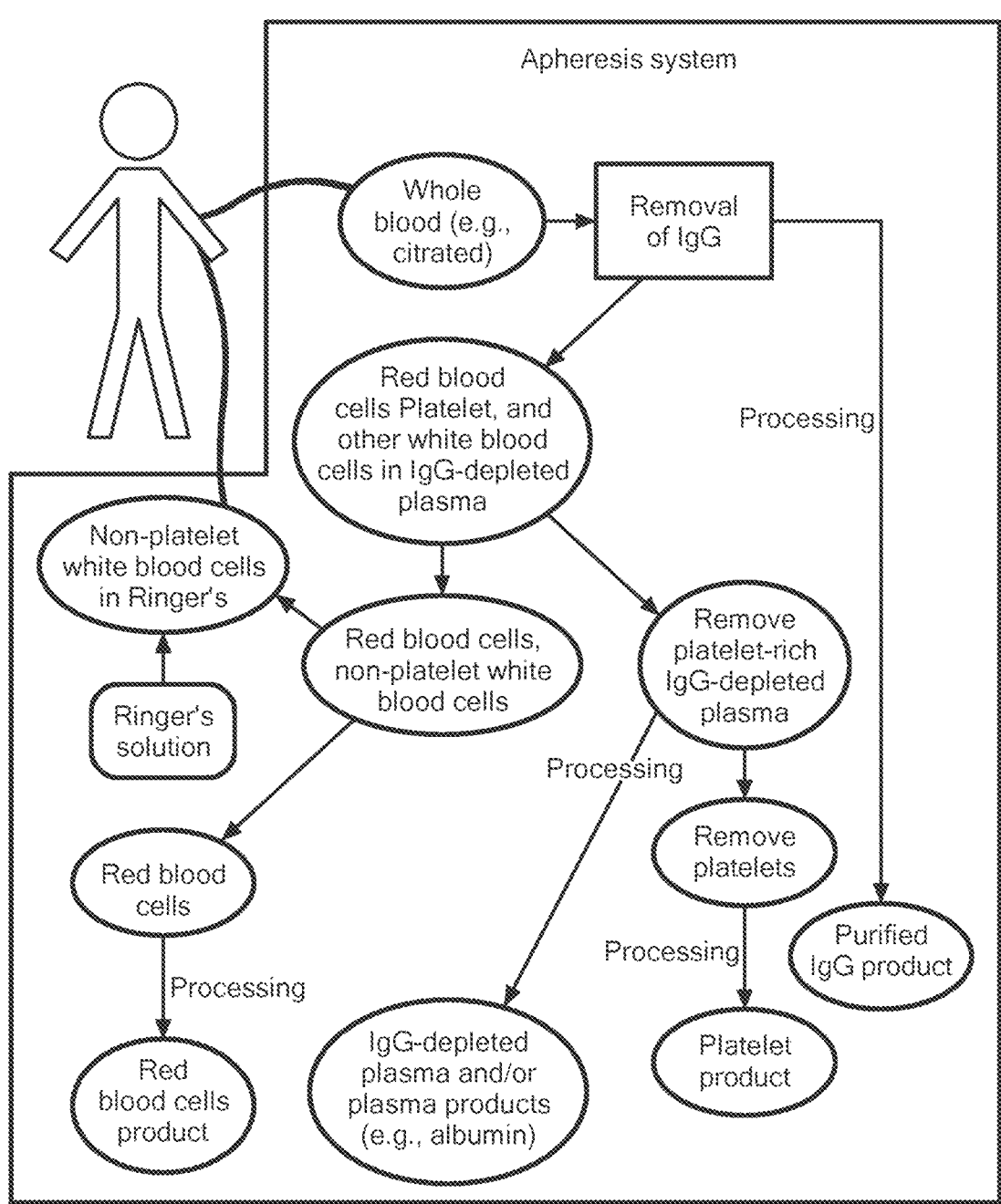
FIG. 7 is a schematic diagram of an apheresis system where purified IgG is one of many products removed from whole blood during apheresis.

Of course, it should be noted that any blood donation system or an apheresis system can be modified to produce purified immunoglobulin. As shown in FIG. 7, a chair-side apheresis system is depicted in which whole blood is donated by the patient, and IgG and first removed. The removed (or extracted) IgG can be further processed either within the apheresis system (as depicted in FIG. 7) or outside of the system (e.g., at a blood bank facility) to produce purified IgG product. Platelet-rich plasma is then removed from the remainder (i.e., removed from the combination of red blood cells and white blood cells in IgG-depleted plasma). Platelets are then removed from the platelet-rich plasma and the two products are further processed to produce a platelet product and an IgG-depleted plasma product. Of course, plasma products such as albumin or Factor VIII can be purified from the IgG-depleted plasma. In the system in FIG. 7, red blood cells are removed from the remaining mixture of red blood cells and non-platelet white blood cells to produce a red blood cell product (e.g., a packed red blood cell product). Only the non-platelet white blood cells remain. These white blood cells include T and B lymphocytes, which are key players in antigen-specific immunity and thus, desirable to be returned to the donor. In FIG. 7, the non-platelet white blood cells are mixed with Ringer's solution (which is isotonic) and administered back to the patient donor using the apheresis system.

Note that if the patient elects to not have his non-platelet white blood cells returned, all of the steps of FIG. 7 can be performed in a blood bank facility and not an apheresis system. Likewise, it should be noted that in all of the methods described herein for purifying IgG from a biological fluid can be performed either in an apheresis system or in a blood bank facility. For example, in FIG. 7, the patient can simply donate a pint of whole blood and walk away. The blood can then be transferred to a blood banking facility, and the desired components (e.g., IgG, platelets, plasma, etc.) can be extracted. The blood from the donor patient can also be pooled with whole blood donated by other donor patients, and the extractions performed from the pooled whole blood.

Note that if the plasma (e.g., IgG-depleted plasma) from FIGS. 6A-6C or 7 is saved and not returned to the patient, the plasma can also be further processed by fractionation in a plasma fractionator machine or system to separate the various components in the plasma including albumin, blood clotting factors such as Factor VIII and Factor IX, fibronectin, and the like. Of course, the processing of the plasma (e.g., immunoglobulin-depleted plasma) can include testing for bacteria, and/or filtering to remove any residual cells, clumps of molecules (e.g., proteins or lipids). The processing can also include freezing at −20° C. or storage at 4° C.

As described herein, any method using ligand (e.g., protein A or protein G, or cibracron blue) covalently bonded (also called "covalently attached") to a solid support can be used to purify or extract immunoglobulin (e.g., IgG) from a biological fluid, or enrich immunoglobulin from a biological fluid. While the results of FIGS. 4 and 5 (as described in more detail in Example 1 below) were obtained using protein A-coated beads in a column, the invention is not so limited. For example, if the biological fluid is passed through a column, the ligand can be covalently bonded to the internal surface of the column (i.e., the surface that will contact the biological fluid). In another example, if the biological fluid is passed through tubing, the ligand can be covalently attached to the internal surface of the tubing (i.e., the surface that will contact the biological fluid). In another example, if the biological fluid is passed through or stored in a bag, the ligand can be covalently bonded to the internal surface of the bag (i.e., the surface that will contact the biological fluid).

In a non-limiting embodiment, if the ligand covalently bonded to a solid support are beads, the beads, likewise, can be used in a variety of ways in accordance with the invention. For example, if the biological fluid is passed through a column, the beads can be contained within the column, where the column, for example, that has an input port and output port configured with filters having pore diameters smaller than the diameter of the beads. In another example, if the biological fluid is passed through or stored in a bag, the beads can be contained within the bag, for example, as a lining on the interior surface of the bag and held within the lining by a mesh having pores with pore diameters smaller than the diameter of the beads.

Where the solid support is either the internal surface of a bag or are beads contained within a bag, any bag configured to hold a sterile liquid such as isotonic saline or a biological fluid (e.g., whole blood or components thereof) can be so modified. In some embodiments, the bag may be configured for use in an apheresis system (e.g., the bag may be adapted with luer-lock adaptors in a system using leur-locks. The immunoglobulin can be collected in real-time or "chairside", while the donor is in the process of donating blood (or a blood product such as platelets or plasma). Standard biological fluid bags (often called blood bags) are commercially available (e.g., from Fenwal, Lake Zurich, Illinois, USA). The bags can be made of a variety of plastic and/or polymer materials such as polyvinyl chloride (PVC), ethylene butyl acrylate copolymer (EBAC) resin, ethylene methyl acrylate copolymer (EMAC) resin, plasticized ultra-high-molecular weight PVC resin, and ethylene vinyl acetate (EVA), and/or can be formed from, for example, polyolefin, polyurethane, polyester, and polycarbonate. Non-limiting examples of such bags are shown in FIGS. 8A and 8B. In FIG. 8A, an input port and an output port are each located at the top of the bag. In FIG. 8B, the input port is located at the top of the bag and the output port is located at the bottom of the bag.

Figure 3:
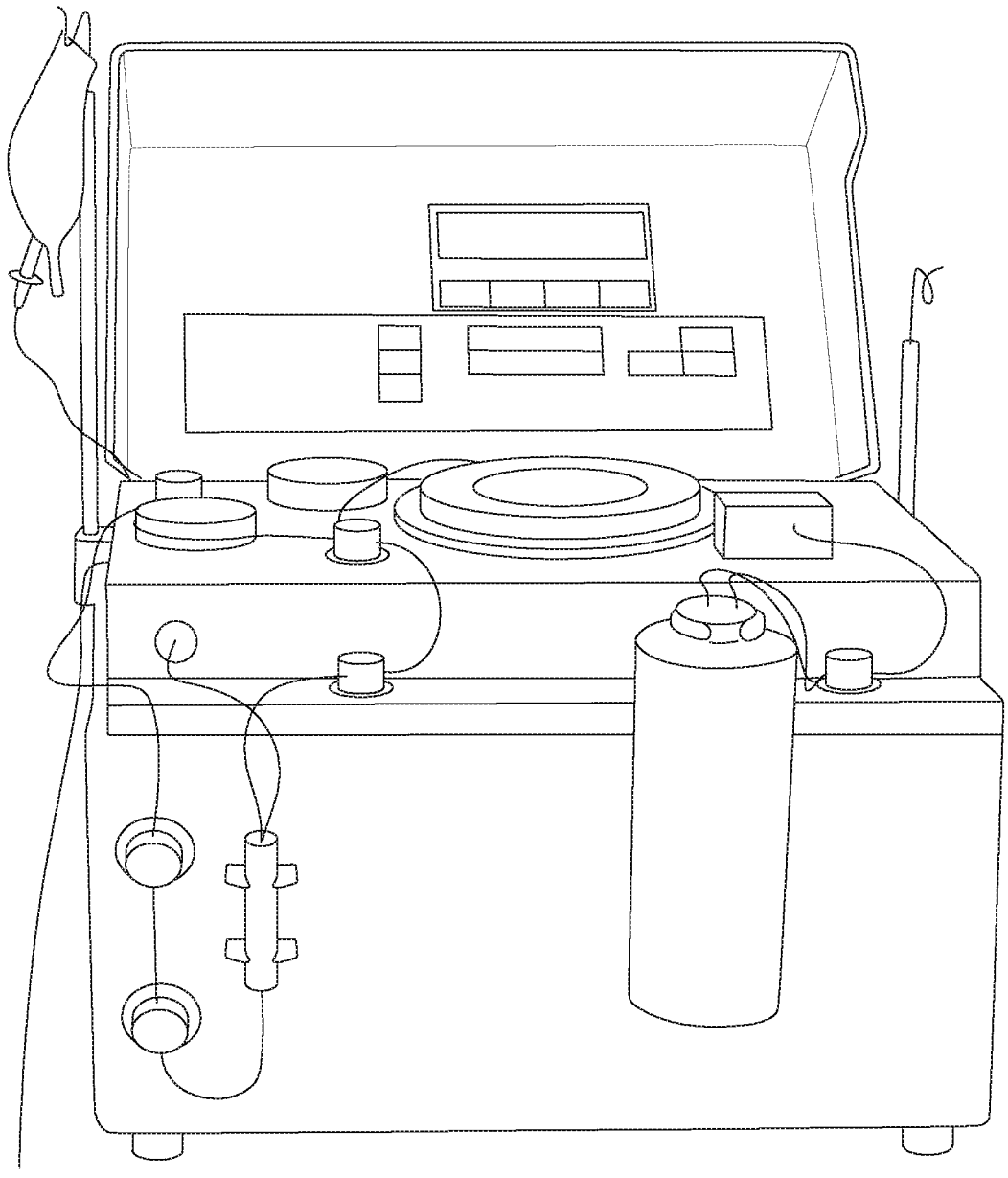
FIG. 3 is a photograph of a non-limiting representative apheresis machine, namely the PCS®2 machine sold by Haemonetics Corp. (Braintree, MA). In this FIG. 3, the apheresis machine shown can be used to collected plasma.

In some embodiments, particularly where the ligand is covalently bonded to beads that are placed into the bag, one or both of the internal surfaces of the bag may be configured to have a porous lining (or mesh) that holds the beads against the surface of the bag (and thus away from the cavity of the bag). In some embodiments, the diameter of the pores in the mesh lining is smaller than the diameter of the ligand-coated beads. Similarly, in some embodiments, the input and/or output port of the bag is adapted to be covered with a filter (also called a frith) having a pore diameter size smaller than the diameter of the beads. In some embodiments, the diameter of the pores in the mesh lining and/or the diameter of the pores in the frith is smaller than the diameter of a nucleated white blood cell (e.g., a monocyte), the pore size of a filter may be smaller than the average diameter of a cell. The average diameter of a monocyte, the largest white blood cell circulating in whole blood, is 15 um to about 30 um. Therefore, the frith and/or the mesh may have a pore size that is smaller than 15 um in diameter (e.g., a pore size of between about 10-12 um).

Where the solid support is either the internal surface of a container (such as a bag) or are beads contained within the container such as a bag, any container configured to hold a sterile liquid such as isotonic saline or a biological fluid (e.g., whole blood or components thereof) can be so modified. In some embodiments, the container can be used in an apheresis system (e.g., in the PCS®2 system shown in FIG. 3). In some embodiments, particularly when the container contains ligand-coated beads, the input and output port are adapted to be covered with a filter (also called a frith) having a pore diameter size smaller than the diameter of the beads. The immunoglobulin can be collected in real-time or "chairside", while the donor is in the process of donating blood (or a blood product such as platelets or plasma).

The container (e.g., bag) can be constructed of any material including, without limitation, plastic, polycarbonate, glass (or reinforced glass), stainless steel, and the like.

Where the solid support is either the internal surface or a column or are beads contained within the column, any column configured to hold a sterile liquid such as isotonic saline or a biological fluid (e.g., whole blood or components thereof) can be so modified. In some embodiments, the column can be used in an apheresis system (e.g., in the PCS®2 system shown in FIG. 3). In some embodiments, particularly when the column contains ligand-coated beads, the input and output port are adapted to be covered with a filter (also called a frith) having a pore diameter size smaller than the diameter of the beads. The immunoglobulin can be collected in real-time or "chair-side", while the donor is in the process of donating blood (or a blood product such as platelets or plasma).

The column can be constructed of any material including, without limitation, plastic, polycarbonate, glass (or reinforced glass), stainless steel, and the like.

In some embodiments, the column is an axial column (e.g., where the biological fluid flows through the column along the length of the column), or a radial flow column, where the biological fluid flows through the column in a circular pattern. Particularly where the column is configured for use in an apheresis system, the back pressure generated by the biological fluid flowing through the column may affect binding efficiency (via non-covalent bonding) of the IgG to the ligand. For example, if the solid support is ligand-coated beads, and the beads are placed into an axial column, the back flow can be high. For example, if the flow rate is 50 ml/minute to 120 ml/minute through the axial column containing ligand-coated beads of approximately 40-80 microns in diameter, the back pressure may be approximately 1,000 mm of mercury.

It should be noted that the height and/or diameter of an axial flow column are unimportant, because one of the determinant factors in the axial flow is the size of resin in the column. For example when 250 mL of resin (e.g., comprising ligand-coated beads) is packed into a GE50/20 column (commercially available from GE Healthcare Life Sciences, Pittsburgh, Pennsylvania, USA), the back pressure at the start of the process with 1000 mL of plasma is in excess of 1000 mmHg. Therefore, for the axial flow, the column can have a diameter from about 10 to 300 mm and a height (or length) from 10 mm to 300 mm. The back pressure in the axial column may potentially be reduced by using a column with an internal diameter larger than 50 mm to 200 mm. However, a column with a diameter this large may be impractical for use with a plasma pheresis machine such as the PCS®2 machine (Haemonetics Corp., Braintree, Massachusetts, USA). In some embodiments, where the column is an axial column, the column has an internal diameter of 50 mm and a length (or height) of 200 mm. In some embodiments, where the column is an axial column, the column has an internal diameter of 10 mm and a length of 20 mm.

Figure 9C:
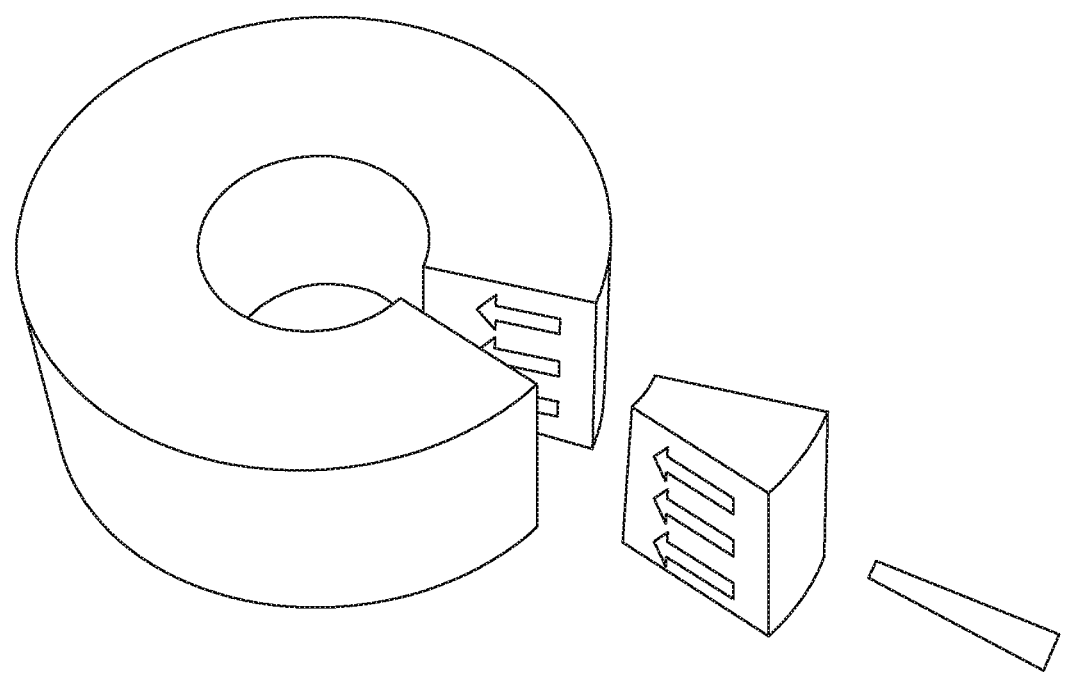

In some embodiments, the column is a radial flow column. With a radial column, the backpressure is significantly reduced and thus allows very good binding efficiency (via a non-covalent bond) of the IgG to the ligand. For example, if the flow rate is 50 ml/minute to 120 ml/minute through the radial column containing ligand-coated beads of approximately 40-80 microns in diameter, the back pressure may be approximately 50 mm of mercury, or between 50-150 mm of mercury. FIGS. 9A-9C shows schematics of a non-limiting column filled with ligand-coated beads that can be used in the various embodiments of the invention. The column depicted in FIGS. 9A-9C is designed to work in conjunction an apheresis machine, such as a plasma apheresis machine or a plateletpheresis machine. In some embodiments, the column is configured to work in conjunction with a PCS®2 plasma pheresis machine (from Haemonetics Corp.). As the maximum back pressure in the PCS®2 plasma pheresis machine is around 100 mm of mercury, in some embodiments, the column used with the PCS®2 machine is a radial flow column. In some embodiments, the column is configured to work in conjunction with a MCS®+ 9000 plateletpheresis machine (from Haemonetics Corp). By "configured" simply means that the indicated object (e.g., a column or bag) is adapted or modified in some way to serve a purpose. For example, when a container is configured to work with a PCS®2 plasma pheresis machine, it simply means that the container is adapted to connect to the PCS®2 plasma pheresis machine, for example, by having an input port and output port of the container modified with adaptors (e.g., luer lock adaptors) that are connectable to adaptors on the PCS®2 plasma pheresis machine. However, it should be understood that this container can work with any apheresis machine or system.

Turning to FIGS. 9A-9C, the non-limiting radial flow column shown is fitted with two ports, an input port and an output port, for inputting plasma and releasing the immunoglobulin-depleted plasma, respectively (see FIGS. 9A-9B). The column depicted in FIGS. 9A and 9B is approximately 12 cm in height with a diameter of 5 cm. Both the input and output ports are adapted with a filter (or frith) having an average pore diameter of approximately 20-30 microns. While luer-lock adaptors are shown in the schematic in FIGS. 9A-9B, the ports can have any adaptor so long as the adaptors are compatible with the adaptors on the tubing system of the apheresis machine (or system) that the column is used with. In embodiments where the immunoglobulin-depleted plasma is returned to the patient (e.g., when the apheresis is plateletpheresis or plasma pheresis), the immunoglobulin-depleted plasma may be mixed with the red blood cells and other donor cells (e.g., non-platelet white blood cells) prior to returning these cells to the donor. These embodiments are depicted in a flow chart in FIGS. 6 and 7.

FIG. 9A shows a section removed length-wise from the column of FIG. 9B, and the packed bed of beads can be seen in FIG. 9A. The height of the bed of the beads is approximately 1 cm in the schematic shown in FIG. 9A, which represents a volume of 240 ml of MabCaptureA beads (with an average bead diameter of approximately 45 microns). Note that ligand-coated agarose beads (having an average bead diameter of 90 microns) can also be used. In some embodiments, a bead diameter of approximately 50 microns or smaller is used. In some embodiments, a bead diameter of approximately 50 microns or smaller allows a higher efficiency of IgG extraction and recovery than a bead diameter of greater than about 60 microns.

The radial nature of the column of FIGS. 9A and 9B can been seen in the slice of FIG. 9A shown in FIG. 9C. As can be seen, the 1 cm bed height in the column is within a tube-like structure in the column that spirals around the center of the column through the height of the column. In this manner, 240 ml of the MabCaptureA beads can be packed into the 12 cm tall column having a diameter of 5 cm.

It should be noted that in all of the embodiments of the invention, any amount of solid support covalently bonded to ligand may be used. In some embodiments, the majority of the IgG (or other immunoglobulin serotype) in the biological fluid being processed (e.g., plasma) will be extracted from or enriched in the biological fluid. Thus, in various embodiments, the methods and apparatuses described herein will extract or enrich at least 50% of the IgG in the biological fluid, or will extract or enrich at least 66% of the IgG in the biological fluid, or will extract or enrich at least 75% of the IgG in the biological fluid, or will extract or enrich at least 90% of the IgG in the biological fluid, or will extract or enrich at least 95% of the IgG in the biological fluid. Once extracted, majority of the IgG is recovered in accordance with the present invention. Thus, in various embodiments, the methods and apparatuses described herein will recover at least 50% of the extracted or enriched IgG, or will recover at least 66% of the extracted or enriched IgG, or will recover at least 75% of the extracted or enriched IgG, or will recover at least 90% of the extracted or enriched IgG, or will recover at least 95% of the extracted or enriched IgG.

For example, where the solid support covalently bonded to ligand are protein A-coated beads, and where the beads are contained within a bag or column, the amount of beads utilized can be modified to extract the most immunoglobulin (e.g., IgG) while using the least amount of ligand. This is useful because a reduction in the amount of ligand reduces any potential amount of ligand that might detach from the solid support and be released into the biological fluid.

In the embodiments described herein where the immunoglobulin (e.g., IgG) is extracted from the biological fluid, to elute the immunoglobulin off the ligand covalently bonded to the solid support (e.g., to elute the immunoglobulin off the ligand-coated beads), a solution having a pH between 2.0 and 3.0 is used as an elution solution. For example, the elution solution may be 100 mM sodium citrate having a pH of 3.0. Once the IgG is eluted off the ligand covalently bonded to the solid support and into the elution solution, the pH of the elution solution is normalized by adding a neutralizing buffer. By "neutralizing buffer" is meant a solution with a pH high enough to obtain a neutral pH (i.e., a pH between 6.0 and 7.0) in the solution to which the neutralizing buffer is added. In some embodiments, the volume of the neutralizing buffer is less than the volume of the elution solution containing the eluted immunoglobulin. For example, if the eluted IgG is in 100 ml of 100 mM sodium citrate, pH 3.0, a 10% volume of a neutralizing buffer can be added, such as 10 ml of 1 M Tris, pH 8.8, resulting in a solution of recovered IgG having a final volume of 110 ml with a pH between 6 to 7. The elution of the non-covalently bound IgG off the ligand and into the elution solution occurs through electrostatic repulsion of the immunoglobulin from the ligand to thereby break the non-covalent bond between the immunoglobulin and the ligand and release the immunoglobulin into the elution solution leaving the ligand still covalently bonded to the solid support.

In some embodiments, where the container (e.g., bag or column) is part of an apheresis system, the elution of the non-covalently bound immunoglobulin off the ligand and into the elution solution occurs "on-line" (i.e., where the container is still attached to the system when the elution solution is passed through the container. In some embodiments, where the immunoglobulin is extracted from a biological fluid, the container may be taken "off-line" and so is no longer attached to the apheresis system when the elution solution is pass through the container to elute the non-covalently bound immunoglobulin off the ligand.

In some embodiments, the elution solution is passed through the container using a pump (e.g., a peristaltic pump). In some embodiments, the pump that pumps the elution solution through the container is part of the apheresis system and the reservoir holding the elution solution prior to pumping it through the container is attached to and thus part of the apheresis system. In some embodiments, the pump that pumps the elution solution through the container is not part of the apheresis system and the reservoir holding the elution solution prior to pumping it through the container not part of the apheresis system.

In some embodiments, the elution solution is passed through the container using the force of gravity. It should be noted that to use the force of gravity to push the elution solution through the container (e.g., in sterile conditions such as under a Laminar flow hood), the back pressure in the container is lower than 50 mmHg (e.g., is as low as 0.1 mmHg).

In some embodiments, the elution occurs after the entire volume of the biological fluid being processed is contacted to the solid support covalently bonded to the ligand. In a non-limiting example, if the column depicted in FIGS. 9A-9C and containing ligand-coated beads is used, the capacity of the column is sufficient to bind to (via a non-covalent bond) all of the IgG in 1 liter of plasma (the volume typically obtained in plasma pheresis). Thus, the entire volume of the 1 liter of plasma can be run through the column, and then the bound IgG can be eluted from the column using an elution solution (e.g., 100 mM sodium citrate at pH 3.0).

In some embodiments, the elution step (i.e., contacting the immunoglobulin non-covalently bonded to the solid support covalently bonded to ligand with elution solution) takes places following contact of a portion of the entire volume of the biological fluid suspected of containing the immunoglobulin (e.g., IgG). After the elution step, the solid surface covalently bonded to the ligand is neutralized, for example, by contacting the surface with a solution having a neutral pH (e.g., a solution with a pH between 7.0 and 8.0) such as 100 mM Tris at pH 7.0 or phosphate buffered saline (PBS) at pH 7.4. After the neutralization step, a second portion of the biological fluid suspected of containing the immunoglobulin is put into contact with the solid surface under conditions where the immunoglobulin in the fluid can non-covalently bind to the ligand. After this second contact step (which may be called a second loading step), a second elution step occurs. This is followed by a second neutralization step. The loading step, elution step, and neutralization step can be performed repeatedly, thereby reusing or recycling the solid support covalently attached to the ligand. Of course, the number of times the steps can be repeated will depend on the stability of the solid support covalently bonded to the ligand. For example, since protein A-coated polystyrene beads are known to be able to withstand a high flow rate, if the solid support covalently bonded to a ligand is protein A-coated polystyrene beads, the beads may be used repeatedly for at least three cycles of steps (i.e., loading, eluting, and neutralizing), or at least five cycles of steps, or at least ten cycles of steps, or at least fifteen cycles of steps, or at least twenty-five cycles of steps, or at least fifty cycles of steps. When the solid support is used in conjunction with plasma pheresis, in some embodiments, a single solid support is used for a single donor.

For example, in some embodiments, where the invention contemplates a column loaded with ligand-coated beads (such as protein A-coated beads), the column may be smaller and loaded with fewer beads, because the bead-loaded column will be reused. In one non-limiting example, since the average amount of plasma obtained during plasma pheresis (e.g., using a PCS®2 machine) is 800 to 1000 mL, a column 12 centimeters in height and 5 centimeters in diameter with 230 ml of MacCapture A beads (average diameter 45 microns) has the capacity to bind to all of the circulating immunoglobulin in that volume of plasma. If the column is reused, the column can be smaller and the amount of beads used can be reduced. For example, the column may be 3 centimeters in height with a 5 centimeter diameter.

By reusing the solid support covalently bonded to the ligand, a significant reduction in materials can be achieved, resulting in lower costs and less biological waste.

Any existing apheresis systems can be modified to incorporate the methods and/or devices described herein. Two non-limiting examples of such apheresis systems are the PCS®2 system sold by Haemonetics Corp. (Braintree, MA) and the MCS®+ 9000 mobile platelet collection system sold by Haemonetics Corp. (Braintree, MA).

For example, to isolate immunoglobulins or immunoglobulins of a particular isotype (e.g., IgG), the PCS®2 system can be modified. U.S. Pat. Nos. 4,086,924; 4,983,158; and U.S. Pat. No. 6,629,919 (incorporated herein by reference) describe some aspects of a plasmapheresis system such as the PCS®2 system. The system described U.S. Pat. No. 6,629,919 uses a disposable set that includes a centrifuge bowl and containers connected to each other with tubing, whereas the blood processing machine, into which the disposable set is loaded, includes a chuck for holding the centrifuge bowl and pumps for moving liquid among the components of the disposable set. Basically, the PCS®2 system operates by withdrawing whole blood from the patient donor via a phlebotomy needle (e.g., having a gauge of 16-17), mixing it with an anticoagulant (e.g., sodium citrate), and pumping it (using peristaltic pumps) via blood compatible tubing into a centrifuge bowl. The whole blood separates into components (e.g., cells and plasma), and the plasma is pushed out of the bowl and into a plasma collection bag as more whole blood from the patient is added to the bowl. In a modification of the PCS®2 system, or a similar plasmapheresis system, instead of being transferred to the plasma collection bag, plasma exiting the centrifuge bowl can instead be first routed through a container, such as a column or bag, comprising a solid support covalently bonded to a ligand that specifically binds to immunoglobulin (such as IgG) to extract IgG from the plasma. The plasma exiting the container (i.e., IgG-depleted plasma) can then be transferred to the plasma collection bag to be collected. The IgG eluted from the container can also be transferred to an IgG collection page. Such a modified PCS®2 system is schematically depicted in FIG. 10A with a column and in FIG. 10C with a bag. The immunoglobulin (e.g., IgG) that is non-covalently bound to the ligand can be eluted and collected, either following the flow-through of all the plasma or on an on-going basis (e.g., multiple elution steps).

Figure 11:
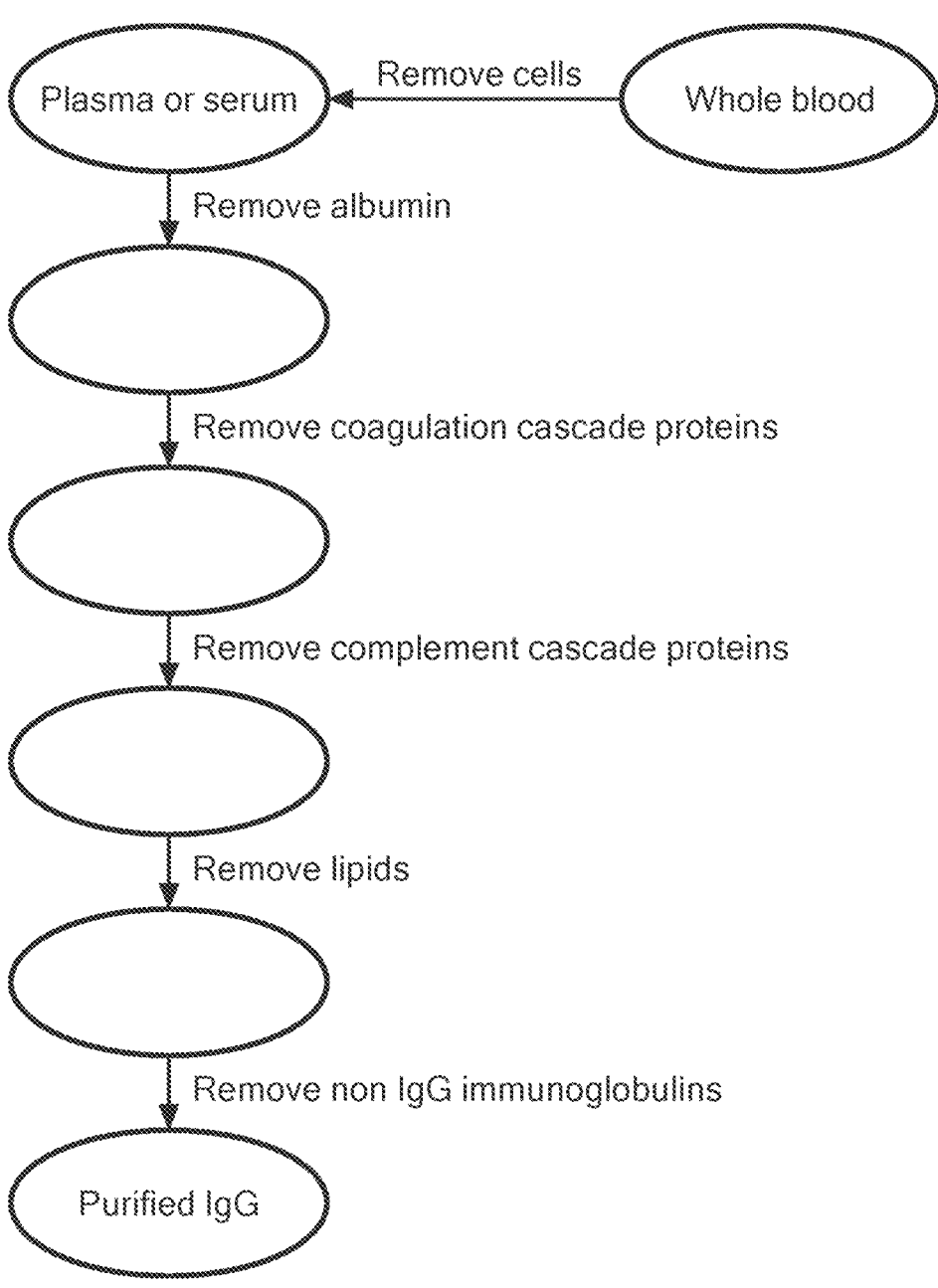
FIG. 11 is a flow chart showing a non-limiting embodiment of purification of IgG by negative selection. It should be noted that the order of the removal steps can be varies. For example, complement cascade proteins can be removed before albumin is removed.

In another aspect, the invention contemplates enriching immunoglobulin such as IgG from whole blood (e.g., from a human) using negative selection. For example, whole blood can be collected from a healthy volunteer donor, and the cells removed. The cells can be removed by any standard method including centrifugation or filtration (e.g., using a filter with pores having diameter of 2 microns, since platelets are approximately 2 microns in diameter) to produce plasma. Another method can be to simply allow the whole blood to coagulate and collect the serum. The plasma or serum can then be further processed to remove non-immunoglobulin components. This negative selection is schematically depicted in FIG. 11. It should be noted that the steps depicted in FIG. 11 are not all required (i.e., steps can be removed) and the order of the steps is not important. The steps in FIG. 11 can be combined, and additional steps can be added. However, FIG. 11 is simply representative of the negative selection process.

For example, since albumin is a common blood protein, albumin can be removed, for example, by passing the plasma or serum (or whole blood) over a solid support covalently bonded to antibody that specifically binds to albumin. Albumin can also be removed by contacting the whole blood (or serum or plasma) with cibacron blue. For example, Bio-Rad Laboratories, Inc. (Hercules, California, USA) sells a chromatography gel that comprises agarose beads covalently bonded to cibacron blue. These beads can be loaded into a column and the blood (or serum or plasma) passed through the column to remove albumin. Coagulation cascade proteins (e.g., fibrinogen, Factor VIII, Factor VI, prothrombin, etc.) and complement proteins (e.g., C3 convertase, mannan-binding lectin, C1q, etc.), can also be removed. Immunoglobulins that are not IgG can also be removed, as can carbohydrates and lipids. The resulting (or remaining) biological fluid is what is left of the whole blood (or plasma or serum) after the non-IgG components are removed. The IgG left in the biological fluid have thus not been contacted with a ligand that specifically binds to the IgG. Moreover, any potential damage to the IgG at a low pH (e.g., a pH of 2.0 to 3.0) can be avoided because the IgG does not have to be eluted from a ligand that non-covalently binds to it.

Figure 10B:
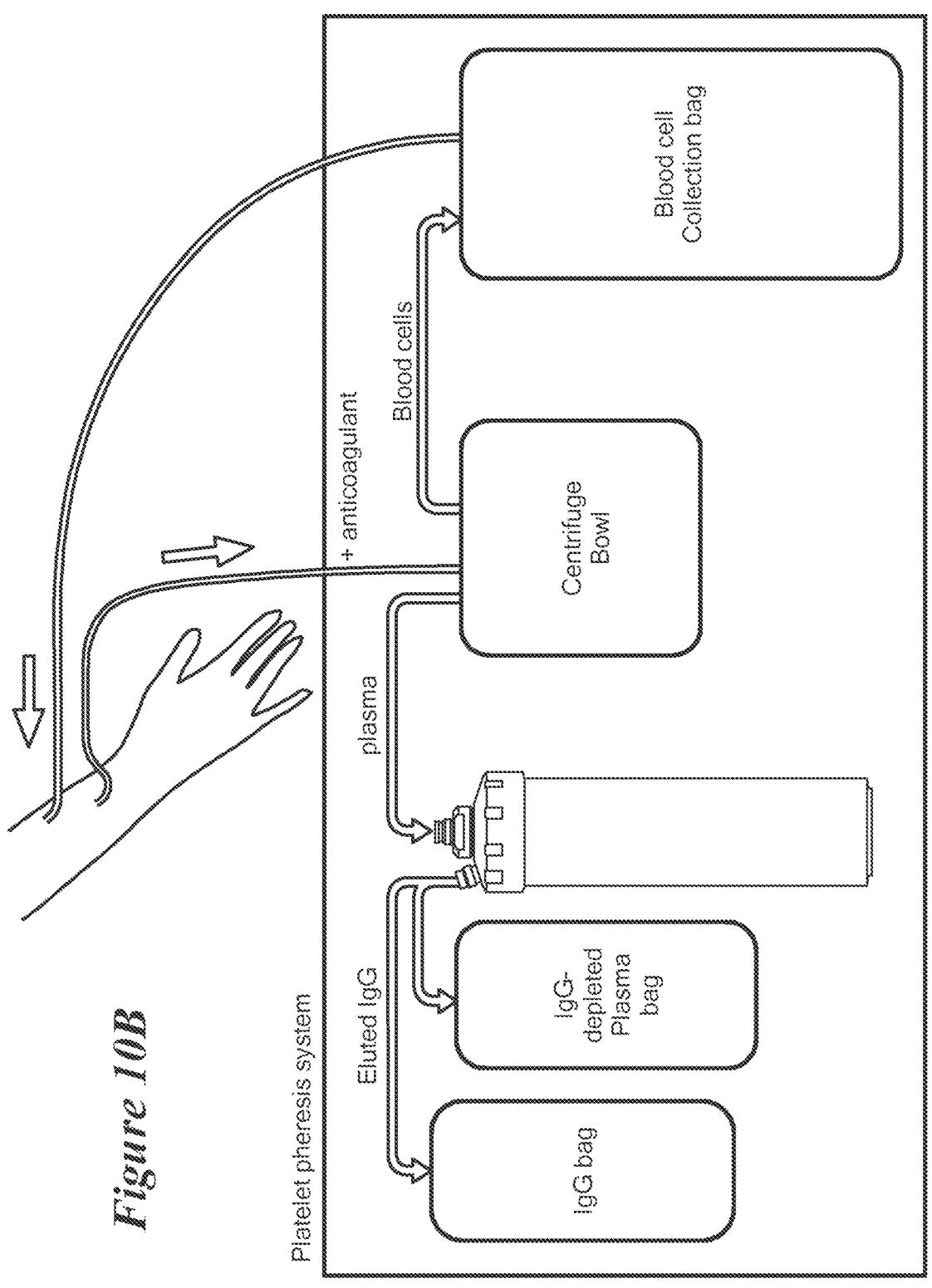
Figure 10C:
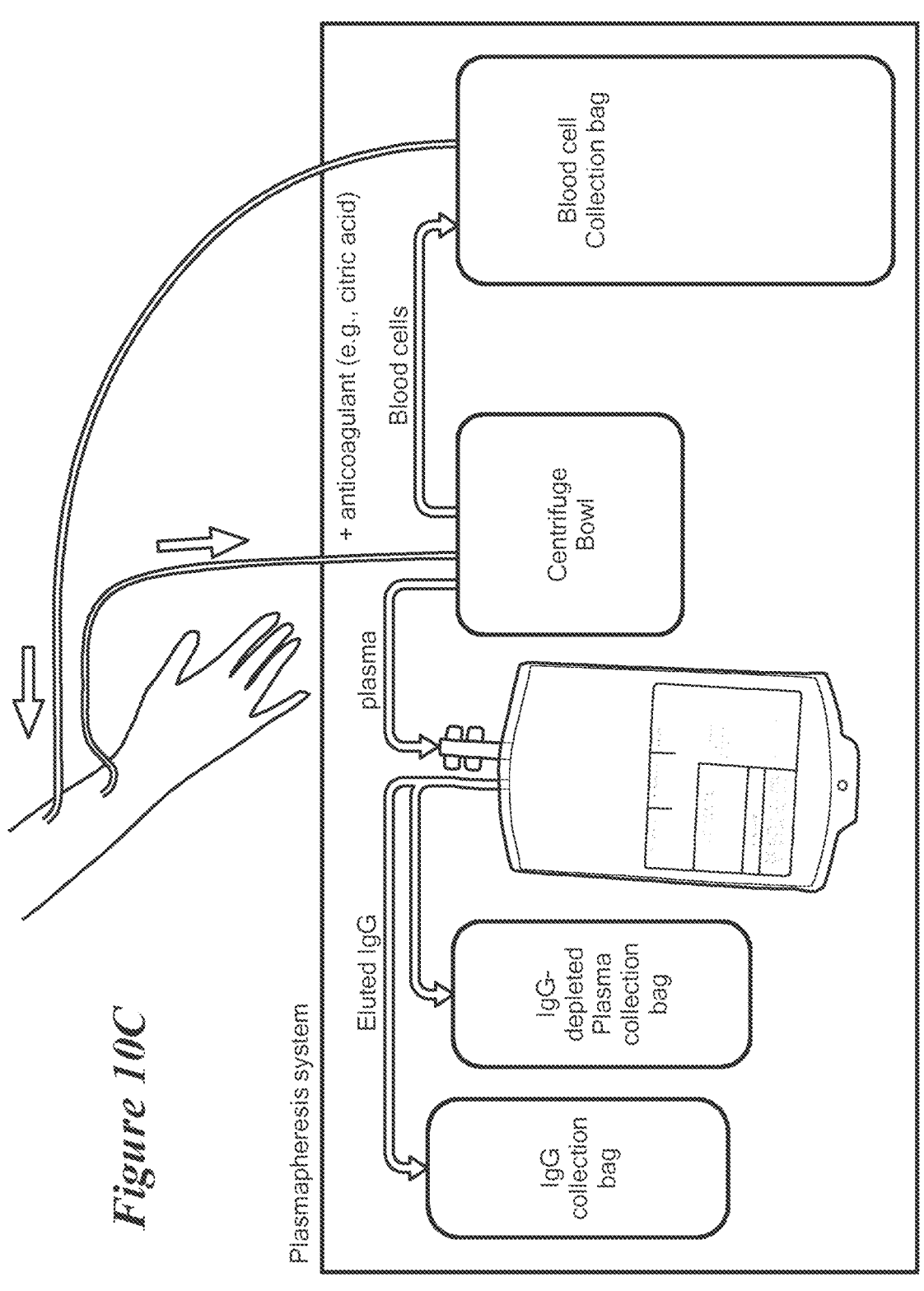
FIGS. 10C and 10D are schematic representations of modifications to a plasma pheresis system, such as the PCS®2 system (FIG. 10C) and to a platelet pheresis system, such as the MCS®+9000 system (FIG. 10D) to incorporate a bag, a non-limiting example of a container comprising a solid support covalently linked to a ligand that specifically binds immunoglobulin.
Figure 10D:
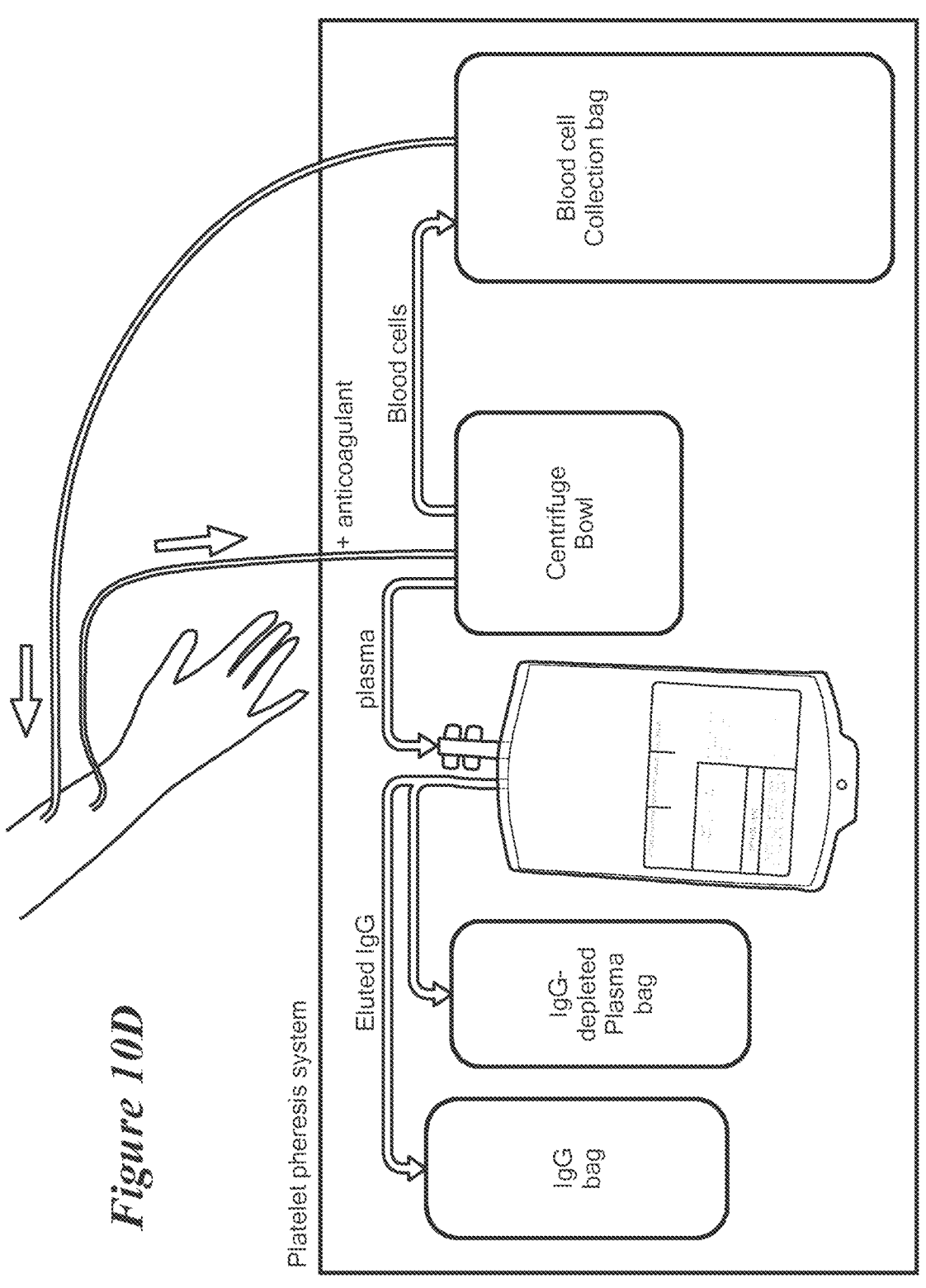
Figure 10E:
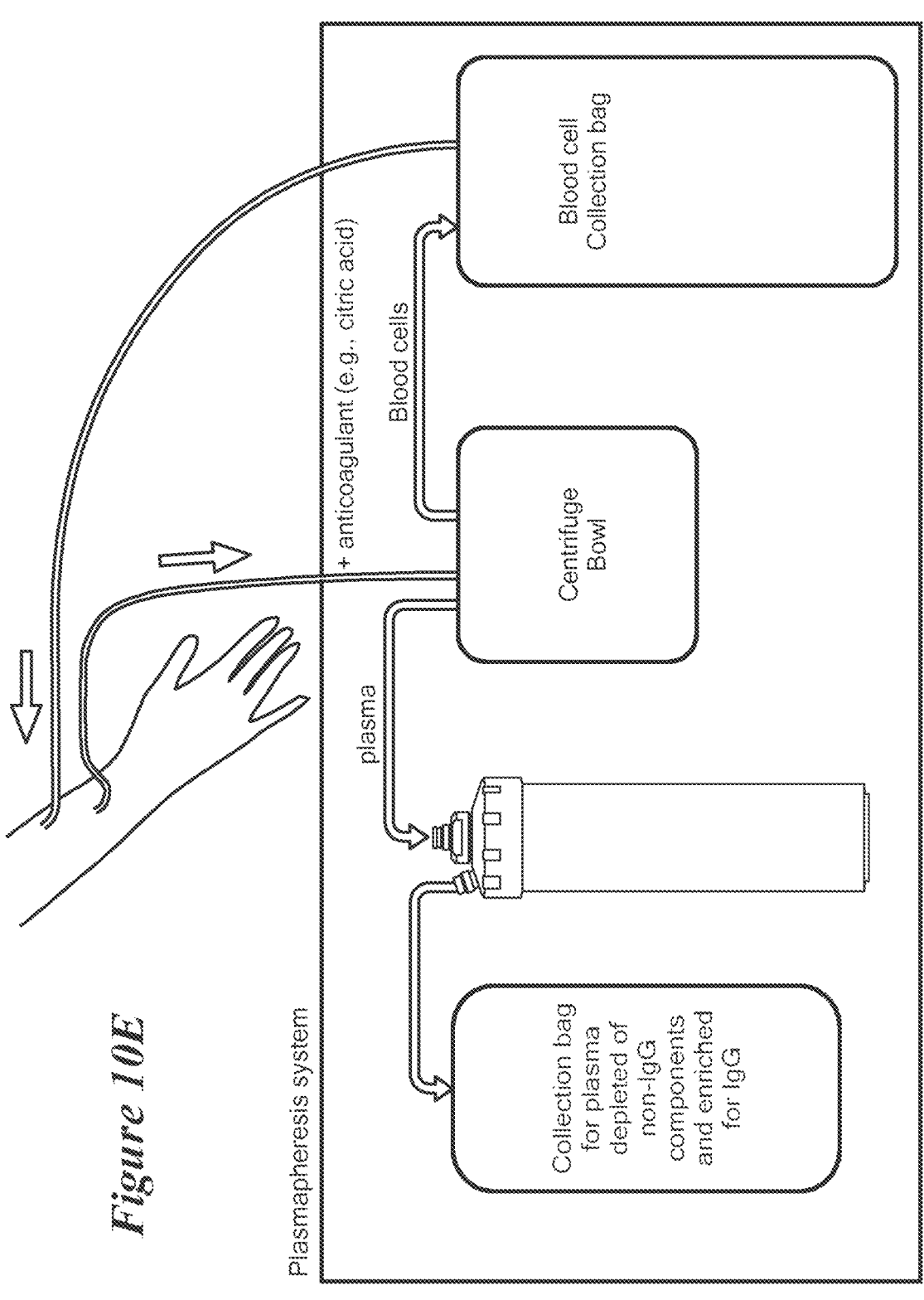
FIGS. 10E and 10F are schematic representations of modifications to a plasma pheresis system, such as the PCS®2 system (FIG. 10E) and to a platelet pheresis system, such as the MCS®+9000 system (FIG. 10F) to incorporate a column, a non-limiting example of a container comprising a solid support covalently linked to a ligand that specifically binds a non-IgG blood component.

In another example, the PCS®2 system can be modified to enrich immunoglobulins. U.S. Pat. Nos. 4,086,924; 4,983, 158; and 6,629,919 (incorporated herein by reference) describe some aspects of a plasmapheresis system such as the PCS®2 system. Basically, the PCS®2 system operates by withdrawing whole blood from the patient donor via a phlebotomy needle (e.g., having a gauge of 16-17), mixing it with an anticoagulant (e.g., sodium citrate), and pumping it (using peristaltic pumps) via blood compatible tubing into a centrifuge bowl. The whole blood separates into components (e.g., cells and plasma), and the plasma is pushed out of the bowl and into a plasma collection bag as more whole blood from the patient is added to the bowl. In a modification of the PCS®2 system, or a similar plasmapheresis system, instead of being transferred to the plasma collection bag, plasma exiting the centrifuge bowl can instead be first routed through a container, such as a column, comprising a solid support covalently bonded to a ligand that specifically binds to a non-immunoglobulin blood component (such as albumin) to extract albumin from the plasma. The plasma exiting the container (e.g., albumin-depleted plasma) which is enriched for immunoglobulin can then be transferred to the plasma collection bag to be collected. Such a modified PCS®2 system is schematically depicted in FIG. 10E.

In another example, the MCS®9000 system can be modified to isolate immunoglobulins or immunoglobulins of a particular isotype (e.g., IgG). U.S. Pat. Nos. 4,983,158 and 5,387,187 (incorporated herein by reference) describe some aspects of an apheresis system such as the MCS®9000 system. Although the MCS®9000 is often used for plateletpheresis, the MCS®9000 can separate a variety of whole blood cell components including platelets, red blood cells, plasma, and combination of these components. Basically, the MCS®9000 system operates using a number of peristaltic pumps together with valves to control the direction and flow of blood (or blood components) from a phlebotomy needle (e.g., having a gauge of 16-17) from a patient donor (e.g., a healthy volunteer). After treatment with an anticoagulant (e.g., sodium citrate), the donor blood is pumped through blood compatible tubing to various containers such a bowls (e.g., centrifuge bowls), bags, and columns, and returns some of the donor blood components (e.g., red blood cells) to the donor via the same phlebotomy needle or a different phlebotomy needle.

In a modification of the MCS®9000 system, or a similar apheresis system, prior to plasma being pumped from the centrifuge bowl into a plasma collection bag, the plasma can be pumped through a container, such as a column or bag, comprising a solid support covalently bonded to a ligand that specifically binds to immunoglobulin, such as IgG, to extract the immunoglobulin from the plasma. A schematic of such a modification is shown in FIG. 10B with a column and in FIG. 10D with a bag. The plasma exiting the container (i.e., immunoglobulin-depleted plasma) can then be collected in a plasma collection bag (see FIGS. 10B and 10D) or returned to the donor. The immunoglobulin non-covalently bound to the ligand can also be eluted and collected into an IgG collection bag as depicted in FIGS. 10B and 10D.

Figure 10F:
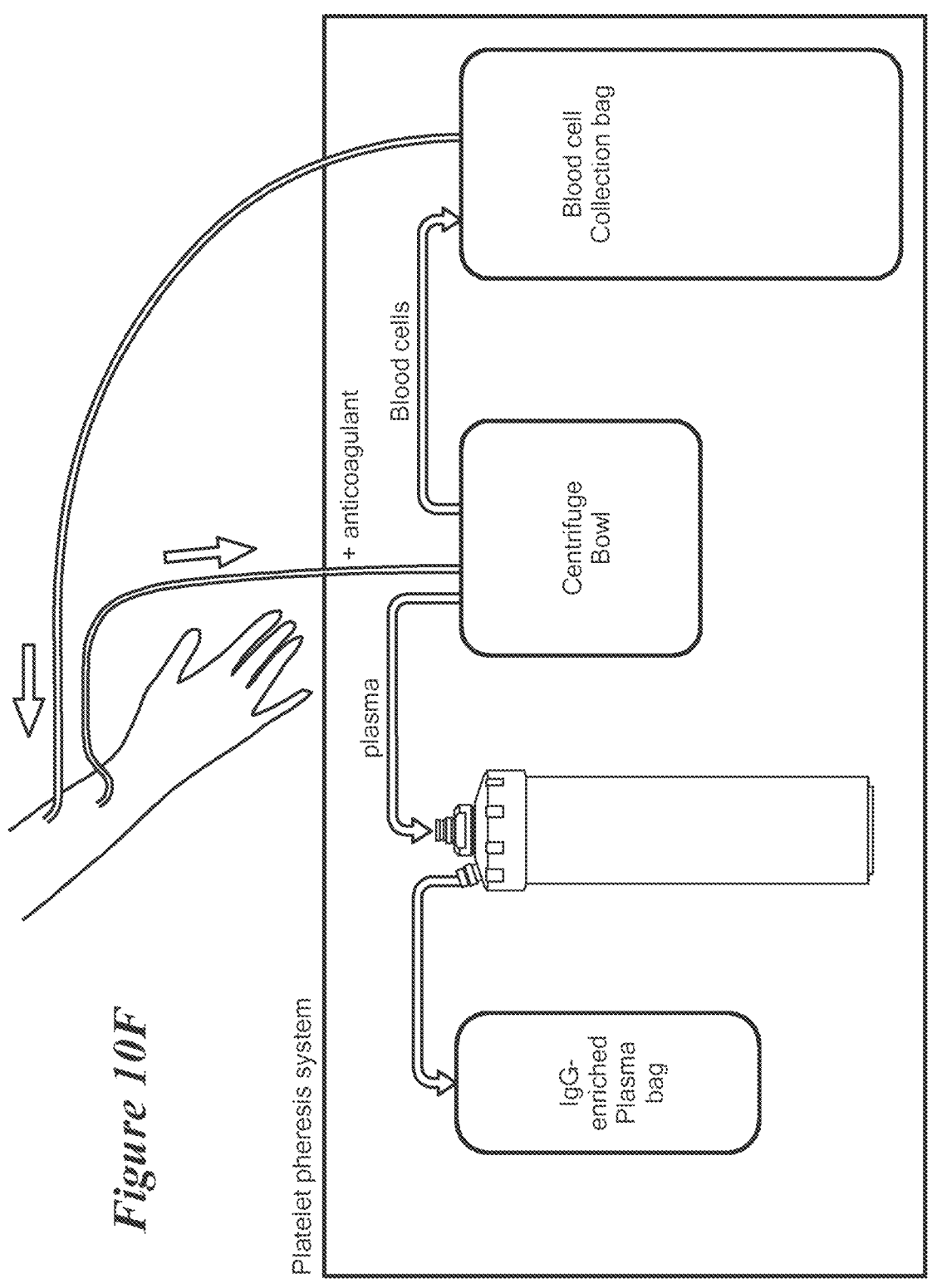

In another modification of the MCS®9000 system, or a similar apheresis system, prior to plasma being pumped from the centrifuge bowl into a plasma collection bag, the plasma can be pumped through a container, such as a column or bag, comprising a solid support covalently bonded to a ligand that specifically binds to a non-immunoglobulin, such as albumin, to extract the albumin from the plasma, thereby enriching the immunoglobulin in the remaining albumin-depleted plasma. A schematic of such a modification is shown in FIG. 10F. The plasma exiting the container (i.e., the albumin-depleted immunoglobulin-enriched plasma) can then be collected in a plasma collection bag (see FIG. 10F).

Following purification or enrichment of the immunoglobulin (e.g., IgG) from a biological fluid (e.g., whole blood, plasma, or serum), the immunoglobulin can be further processed, used immediately, or stored. For example, the immunoglobulin can be frozen at −20° C. or −70° C. When a frozen immunoglobulin is thawed prior to use therapeutically, the frozen immunoglobulin can be quickly thawed (e.g., in a 25° C. or a 37° C. or a 45° C., or a 60° C.

water bath) or can be slowly thawed (e.g., on ice, with intermittent shaking). The IgG can also be lyophilized and stored in a lyophilized form.

The following examples in no way limit the present invention.

Example I 230-250 ml of MabCapture A beads in a resin (i.e., the Protein A affinity ligand, MabCapture A media obtained from Life Technologies (Carlsbad, California, USA) is resuspended in sterile phosphate buffered saline (PBS), pH 7.4 and rinsed. The beads suspended in PBS are then loaded into a column such as that depicted in FIGS. 9A-9C under sterile conditions. The excess PBS is allowed to drain from the column, leaving a resin that is wet through the residual PBS remaining due to surface tension of the beads and the column. The column is 12 centimeters tall with a diameter of 5 cm, and the volume of the resin within the column is 11.7 cm, with a bed in each radial curve in the column of 1 cm. The input and output ports of the column are fitted with a frith (or filter) having a pore diameter of 20-30 microns.

The column is attached to a PCS®2 machine, and a volunteer donor is hooked up to the machine to begin donating his plasma. The plasma obtained from the donor is pumped into the MabCapture A bead-loaded column through the mechanism of the PCS®2 machine at a flow rate of between about 20 ml/minute to about 120 ml/minute, such as a flow rate of about 50 ml/minute. Approximately 800-900 ml of plasma are passed through the MabCapture A bead-loaded column. In some embodiments, as the plasma depleted of IgG (or having a reduced quantity of IgG) is routed back to the bowl containing the donor's cells. The cells and the IgG-reduced (sometimes called IgG-depleted) plasma are mixed and returned to the volunteer donor by the PCS®2 machine.

Following the plasmapheresis procedure, the MabCapture A bead-loaded column loaded with IgG is unhooked from the PCS®2 machine under sterile conditions.

An elution solution of 100 mM sodium citrate at pH 3.0 is used. 250-500 ml of elution solution is passed through the MabCapture A bead-loaded column loaded with IgG. In some embodiments, the passage of elution solution through the column flows at a flow rate set by gravity. In some embodiments, the passage of elution solution through the column flows at a flow rate set by a machine such as a PCS®2 machine modified for this purpose. Thus, in some embodiments, the loading (i.e., adding the plasma to the column) and the elution (i.e., adding the elution solution to the column) is fully automated. In some embodiments, the flow rate of the elution solution is 50 ml/minute to 150 ml/minute through the column.

Following completion of elution, 10% of a neutralizing buffer is added to the elution solution containing the IgG. For example, if 500 of elution solution containing IgG is obtained from the column, 50 ml of a neutralizing buffer (e.g., 1 M Tris, pH 8.8) is added to the elution solution to result in an IgG-containing solution of 550 ml volume at a pH of 6.0 to 7.0.

In some embodiments, the neutralization step is also fully automated (e.g., by modifications to an apheresis machine such as a PCS®2 machine).

The IgG-containing solution can then be used immediately (e.g., administered therapeutically to a patient in need thereof) or further processed and/or stored (e.g., frozen).

Results from this Example 1 have shown that 90-95% of the IgG in 1000 mL plasma from a PCS®2 plasmapheresis machine can be captured in the column containing 230-250 mL of protein A-coated beads (namely the MabCapture A resin on 50 micron polystyrene beads) used chair-side by the donor patient. 90-90% of the captured immunoglobulin was able to be recovered into the elution solution (which was then neutralized). The recovered (i.e., eluted) immunoglobulin was at least 90% IgG.

Example 2

To reduce costs and to enhance efficiency and safety, a smaller version of the column depicted in FIG. 9A-9C is loaded with MabCapture A resin. The column is 3 cm tall with a diameter of 5 cm, and the amount of resin used is 50 ml. The beads in the resin are washed and resuspended in PBS, pH 7.4 as described in Example 1, and then are loaded into the column.

In some embodiments, the column is attached to a PCS®2 machine, and volunteer donor is hooked up to the PCS®2 machine to start plasma pheresis. 100 ml of plasma is flowed (e.g., pumped using, for example, a standard peristaltic pump or a pump incorporated in the PCS®2 machine) through the column. When the 100 ml of plasma is flowed through the column, the tubing from the donor plasma to the input and output ports of the column are closed off, and the plasma from the donor is collected into the plasma collection bowl in the PCS®2 machine. The "detached" column is not actually physically removed from the PCS®2 machine; rather, the column is attached (e.g., via a clamp switching device) to a second reservoir of fluid (e.g. of elution solution) to pump 25 ml of elution solution though the column. 2.5 ml of neutralizing buffer is added to the elution solution exiting the column. The tubings to the elution solution-containing reservoir and the neutralizing buffer-containing reservoir are closed off, and the tubing to the plasma bowl from the donor is opened. Another 100 ml of plasma is pumped through the column.

The cycle is repeated 8-10 times, to accommodate the 800-1000 ml of plasma obtained from the donor.

Example 3

Initial studies found that that about 90-95% of human immunoglobulin G (IgG) could be efficiently captured from 1000 mL of plasma with 90-95% efficiency of release of the captured IgG G with greater than 90% purity. These initial chairside IgG removal studies were conducted with about 230-250 mL of Protein A affinity ligand (MabCapture A resin on 50 micron polystyrene beads) in axial columns. However, the use of the axial column resulted in significant increase in backpressure well above 1000 mmHg. This high backpressure with the axial column is above the maximum acceptable limit of 100 mmHg in the PCS®2 plasmapheresis system (sold by Haemonetics Corp., Braintree, Massachusetts, USA). Therefore, an alternative column that would allow maintenance of the backpressure well below 100 mmHg during IgG removal from plasma during plasmapheresis was evaluation. In this Example 3, the performance of a radial flow column was evaluated.

For these studies, an initial evaluation with water and high viscosity glycerol solutions was performed. Briefly, water and glycerol solutions at different viscosities (2, 3 and 4 centipoise (cP)) were passed through either an axial column or a radial flow column at a flow rate of 150 mL/minute. Each column contained 200 mL of packed 50 micron protein A affinity resins (MabCapture A media, Life Technologies, Carlsbad, California, USA). The bed height of the resins in the axial column was 10.5 cm as compared to 3.0 cm for the radial column.

Note that the bed heights of both the axial column and radial column refer only to bed heights of the resin in each column and not the total height of the column. For example, the total physical height of the axial column could be 12 cm or 20 cm depending on the various adaptors (luer locks for tubing connection, inlet and out ports etc.), whereas the space occupied by the resins is 5 cm (width)×10.5 (height of resin bed). The only relevant dimensions are the bed height and the width or diameter of the column which is then used to calculate the volume occupied by the resins. Therefore, the volume occupied by the resin=$\Pi r^2 h$ where r is the radius and h is the height. Similarly for the radial column, the height of the resin is 3 cm in a column with a width of 12.2 cm. The total physical height of the radial column could be as high as 12 cm depending on the various adapters that are attached to the column.

The inlet pressures in both columns were measured with a mercury manometer.

In a second experiment, the design of the radial flow column was modified and the radial column was packed with 245 mL of resin instead of 200 mL with a bed height of 1 cm instead of 3 cm.

Figure 12:
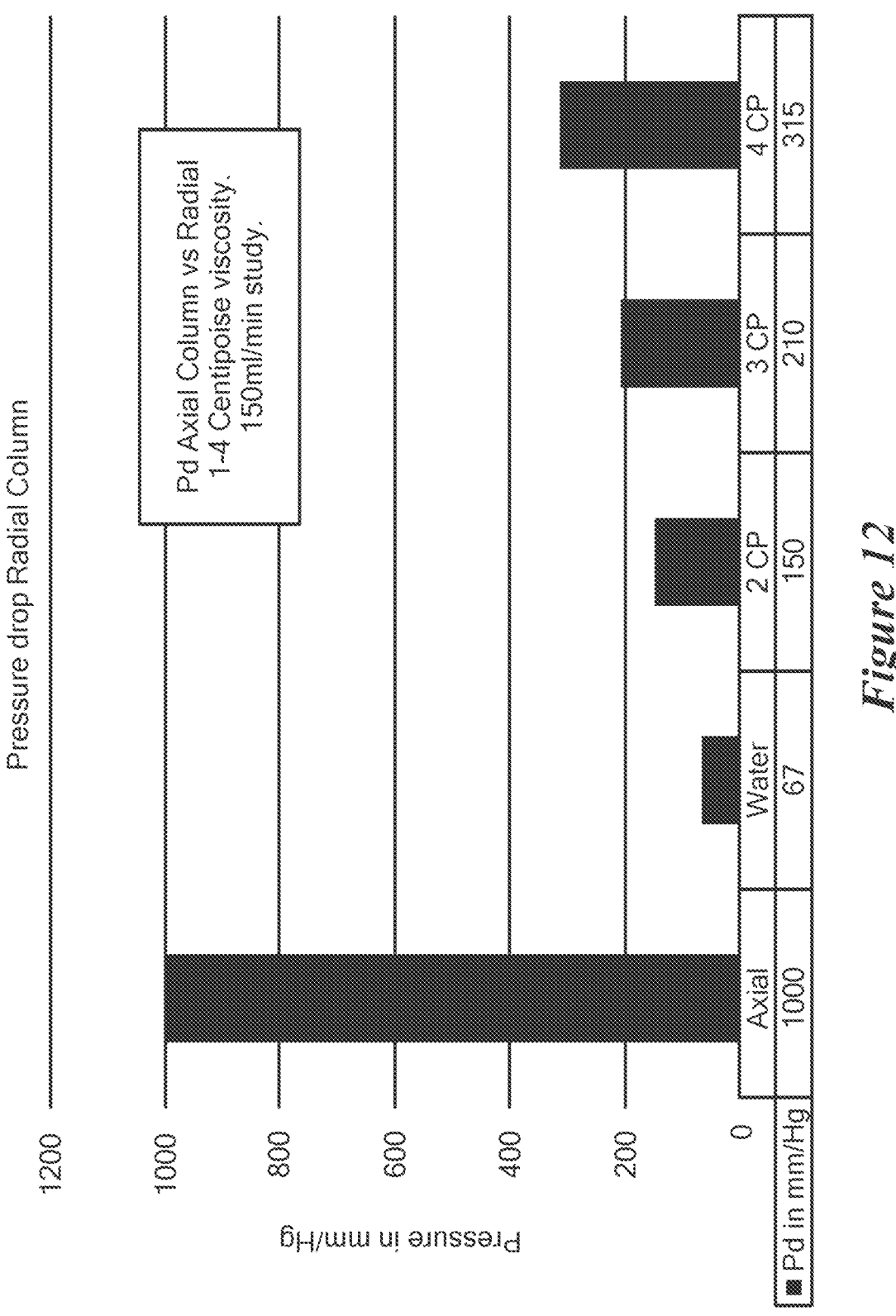
FIG. 12 is a bar graph showing the back pressure in an axial column with water (first bar on the left) as compared to a radial column with a bed height of 3 cm with water (second bar), or water/glycerol mixtures of the indicated viscosities (third, fourth, and fifth bars).

The results show differences in back pressure between radial and axial flow columns. FIG. 12 shows the comparison of back pressures between an axial flow column and 3 cm bed radial flow column. The data presented in FIG. 12 show significant differences in backpressures between axial and radial flow columns. Using water and a radial flow column with 3 cm bed height, the back pressure (indicated as "pd" for "pressure drop" in FIG. 12) was reduced from 1000 mmHg for the axial flow to about 67 mmHgh in the radial flow column for water. The pressures for the water/glycerol mixtures at the indicated viscosities in the radial column are also shown, with the pressure increasing with increasing viscosity (see FIG. 12). Note that even with a viscosity of 4 cP, the pressure in the radial column is still only 325 mmgHg.

Figure 13:
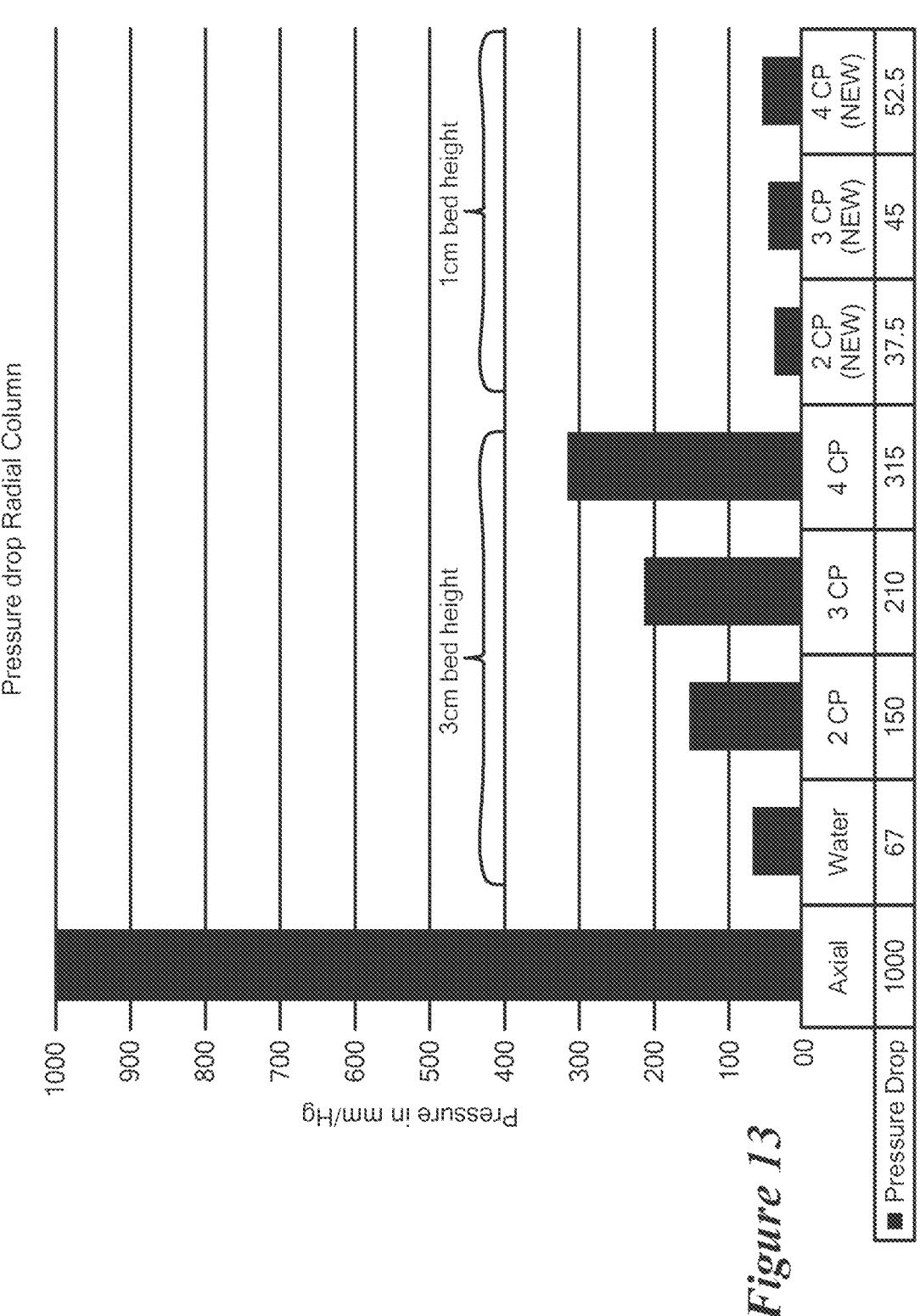
FIG. 13 is a bar graph comparing the back pressures in an axial column with water (first bar on the left), a radial flow column with a bed height of 3 cm with water (second bar) or water/glycerol mixtures at the indicated viscosities (third, fourth, and fifth bars), and a radial flow column with a bed height of 1 cm with water/glycerol mixtures at the indicated viscosities (sixth, seventh, and eighth bars).

FIG. 13 shows the comparison of back pressures generated in an axial flow column (left column), a radial flow column with a 3 cm bed diameter (next four columns) and a radial flow column with a 1 cm bed diameter (three right-most columns). As FIG. 13 shows, reducing the bed height to 1 cm in the radial flow column substantially reduced the back pressure further to less than 40 mmH with the water/glycerol solution at 2 cP.

The results in FIG. 13 show that the radial flow column with 200 mL of resin at a bed height of 3 cm was very effective in allowing the capture and recovery of IgG with greater than 95% efficiency which was maintained throughout five cycles of 1000 ml plasma per cycle. The same column was used (following cleaning in between cycles) for all five cycles; thus, five donor samples were processed using the same column. At each cycle, 1000 mL of plasma was processed, resulting in a total of 5000 mL of plasma processed.

For the evaluation of the radial flow column with human plasma, plasma samples were obtained from healthy blood donor volunteers into citrate phosphate dextrose (CPD) or citrate phosphate double dextrose (CP2D) anticoagulant. A total of 1000 mL was collected for each test. On the day of the test, the plasma was transferred into a 1000 mL blood transfer bag. The inlet tubing on the plasma bag was connected to a pump on a test bed that simulated the operations of the PCS2 plasmapheresis device. A radial column containing 200 mL of MabCapture protein A affinity resin with a bed height of 3 cm was connected to the inlet port on the plasma bag through the infusion pump on the test bed. The plasma was passed through the radial column at a flow rate of 120 mL/minute. Twenty five (25 mL) fractions were collected until the whole 1000 mL plasma was passed through the column. After the initial filtration step, the column was rinsed with 200 mL of phosphate buffered saline, pH 7.4 (PBS) and the effluent was discarded. In order to recover the captured IgG, the radial column was perfused with 1000 mL of 100 mM sodium citrate, pH 2.9-3.0 solution at a flow rate of 120 mL/minute. Similarly, 25 mL fractions were collected until the whole 1000 mL of the elution solution was passed through the column. The experiment was repeated again for 5 times using the same radial flow column.

Figure 14:
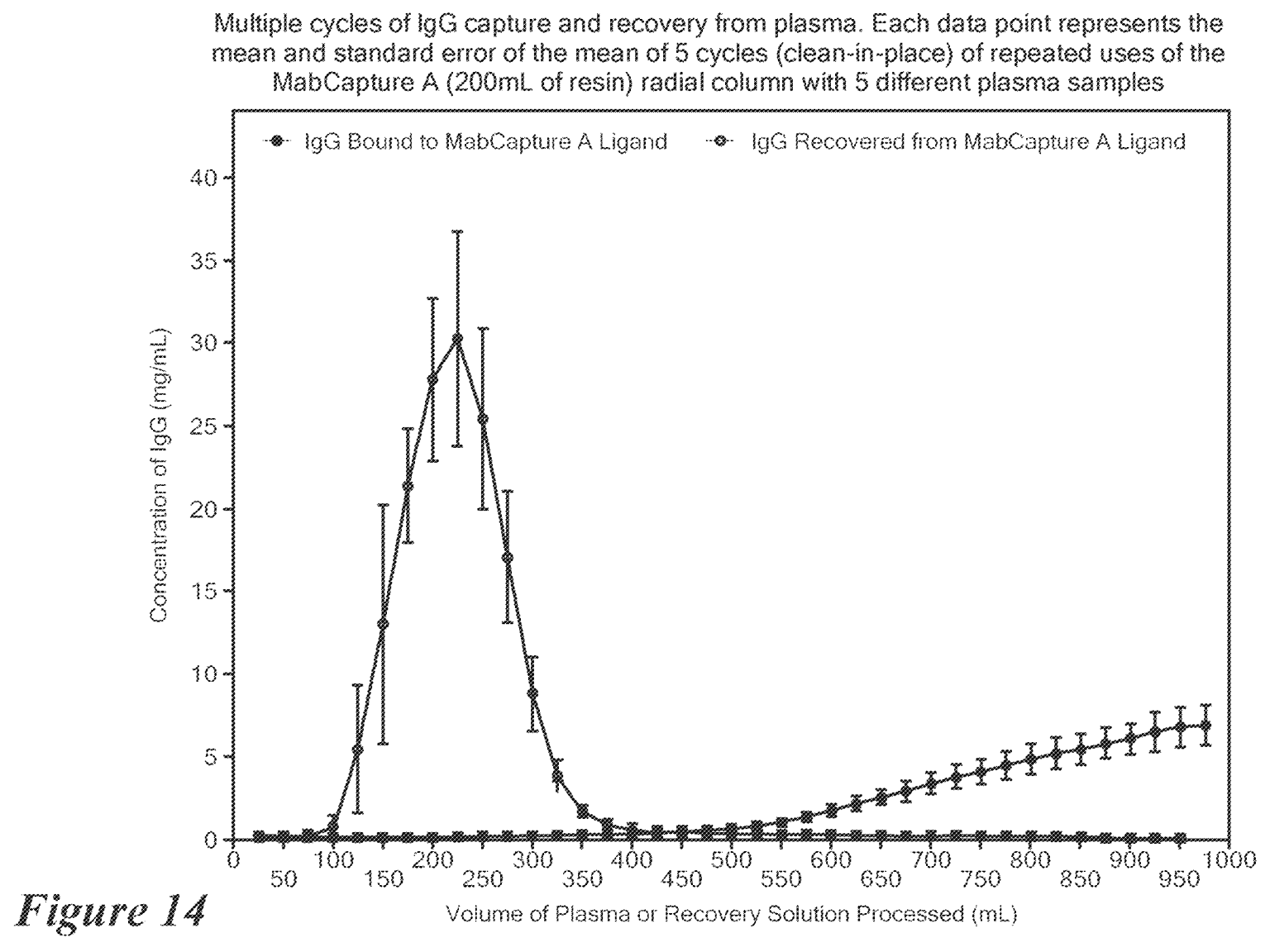

As shown in FIG. 14, the radial flow column with 200 mL of resin at a bed height of 3 cm was very effective in allowing the capture and recovery of IgG with greater than 95% efficiency which was maintained throughout the 5 cycles. The amount of IgG present in each of the test samples prior to loading onto the column is provided in Table 1.

TABLE 1

| Test No. | Starting Concentration of IgG in plasma (mg/mL) |
|---|---|
| 1 | 9.43 |
| 2 | 9.66 |
| 3 | 7.67 |
| 4 | 9.05 |
| 5 | 7.69 |
| Mean | 8.7 |
| Standard deviation | 0.96 |

As shown by the red circles in FIG. 14, all of the IgG present in the plasma loaded onto the column was specifically bound (non-covalently) to the MabCapture A ligand in the column. As the green circles in FIG. 14 show, all of the IgG bound to the column was subsequently recovered by eluting the IgG off the column with 1000 mL of the 100 mM sodium citrate elution solution. Note that in each test cycle in FIG. 14 and Table 1, 1000 mL of plasma was processed, resulting in a total of 5000 mL of plasma processed.

This Example 3 shows that the backpressure that was generated during processing in an axial column is in excess of 1000 mmHg. This backpressure was substantially reduced to less that 100 mmHg in a radial flow column (see FIGS. 12-13). The radial flow column had a greater than 95% efficiency in capture and recovery of captured IgG (see FIG. 14 and Table 1).

Note that this Example 3, all of the steps for purifying IgG (i.e., contacting the biological fluid to the solid support covalently bonded to a ligand that specifically binds to IgG, eluting the bound IgG off the ligand, and neutralizing the elution solution containing the recovered IgG to obtain a solution containing purified IgG) can be performed in an automated manner (i.e., performed by machine). The recovered IgG can then be used immediately (e.g., administered therapeutically to a patient in need thereof) or further processed and/or stored (e.g., frozen).

Example 4

This Example 4 describes a study performed to determine the efficiency of the smaller column. Note that the column used in this Example 4 is radial flow column.

Figure 15:
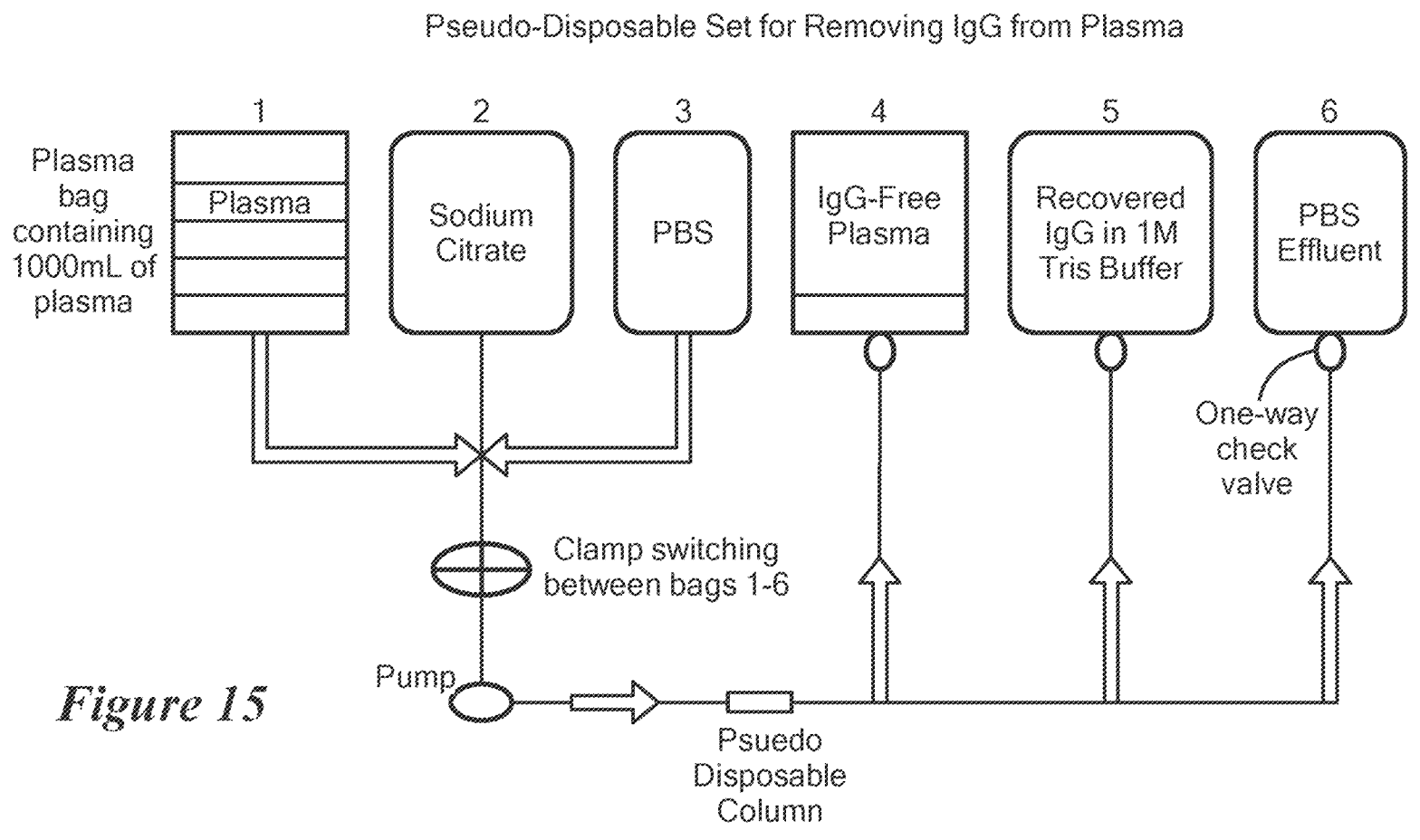

Specifically, Protein A affinity ligand, in particular a MabCapture A ligand, was obtained from Life Technologies Corp. (Carlsbad, CA, USA). A column was prepared by transferring 50 mL of the MabCapture A resin into a GE50/20 column (purchased commercially from GE Health-care Life Sciences, Pittsburgh, Pennsylvania, USA) with a bed height of 2.5 cm and an internal diameter of 5 cm. Plasma samples were obtained from healthy blood donor volunteers into standard amount of citrate phosphate dex-trose (CPD) anticoagulant. A total of 1000 mL of plasma was transferred into a 1000 mL blood transfer bag and connected to a pump via blood-compatible tubing as shown in the set up depicted schematically in FIG. 15. As shown, FIG. 15 schematically depicts six bags or bowls, a column (labeled as the "pseudo-disposable column") and a volume of 200 ml per cycle. In FIG. 15, the steps are as follows:

Briefly, in step 1, the clamp switching device was opened so that the plasma was passed through the "Pseudo Dispos-able Column" at a flow rate of 120 mL/min for about 1 minute and 40 seconds to allow 200 mL of plasma to pass through the column into the IgG-free plasma collection bag (bag 4), after which the clam switching device was closed. Note that this flow rate can be between 50 ml/minute to about 200 ml/minute. During step 1, the valves for the PBS and sodium citrate remain closed. In step 2, the clamp switching device was switched to open position to allow 100 mL of phosphate buffered saline, pH 7.4 (PBS) to flow through the column at a flow rate of 120 mL/minute from bag #3 into bag #6 (the "PBS eluent" bag) (total time is 50 seconds). After 50 seconds, in step 3, the clamp switching device was set to the open position to allow 100 mL of 100 mM sodium citrate (pH 2.8) to flow through the column at a flow rate of 120 mL/minute to release the captured IgG into bag 5 (the "recovered IgG in 1 M Tris Buffer" bag"). Note that in some embodiments, the bag 5 already contains the 1M Tris, pH 8.8, into which the captured IgG in the elution solution is added. After 50 seconds, the switching clamp was set back to the open position to allow plasma to flow through and steps 1-3 were repeated again for four times for a total of five cycles to allow a total of 1000 mL of plasma to be processed.

It should be noted that the initial emptying of the recov-ered IgG into bag 5 of FIG. 15 will result in a solution having a pH higher than 8.0. However, after the fifth cycle, the pH of the final solution will be between about 7.0 and 8.0. However, as each of the cycles takes only a few minutes, the higher pH in the initial cycles do not adversely affect the recovered IgG. In some embodiments, 50 mL of 1M Tris, pH 8.8 is added after all of the captured IgG is collected into bag 5 after all five cycles are completed.

The results obtained using the set-up depicted in FIG. 15 are summarized in FIG. 16. As shown in FIG. 16, the plasma had an initial concentration of 7.7 mg/mL IgG, and therefore the total amount of IgG in the 200 mL was 1.54 g (($200\times 7.7/1000$). The residual amount in the IgG free plasma was below the limit of detection of the assay, therefore the amount of IgG captured during the first cycle was actually between 96-100% dependent on the limit of the detection of the assay. Therefore, for 100% removal, since the residual amount of IgG in the plasma was below the limit of detection of the assay at less than 0.171 mg/mL, it was assumed that the residual amount of IgG in the plasma after the first cycle was 0 since the actual concentration of IgG was below the limit of detection of the assay.

Thus, although 95-100% of the IgG in plasma was cap-tured by the column, only 73.7% was recovered. The cal-culations are shown below.

Starting amount of IgG in 200 mL of plasma=1.54 g

Concentration of IgG in 100 mL of recovery solution=1.1

Percent of IgG recovered=(1.135/1.54)×100)

Percent of IgG recovered=73.7%.

Similar IgG capture efficiency was obtained in the sub-sequent 200 mL of plasma aliquot processed (data not shown). Treatment of the column with 100 mL of the 100 mM of sodium citrate elution solution at pH 2.8 resulted in about 76.6% recovery of the captured IgG. The immuno-globulin isotypes showed significant enrichment of IgG in the recovered solution with greater than 91% IgG when compared to the starting value of about 73.7% in human plasma (see FIG. 5).

After repeating the steps 5 times, the "Pseudo-Dispos-able" column was then discarded. Thus, a single "Pseudo-Disposable" column was used per single donor.

As noted above, the time for each cycle takes only a few minutes. Thus, when the set-up schematically depicted in FIG. 15 is incorporated into a plasmapheresis machine, the time for the plasmapheresis procedure is not lengthened significantly. It should be further noted that in this Example 4, all of the steps for purifying IgG (i.e., contacting the biological fluid to the solid support covalently bonded to a ligand that specifically binds to IgG, eluting the bound IgG off the ligand, and neutralizing the elution solution contain-ing the recovered IgG to obtain a solution containing puri-fied IgG) are performed in an automated manner (i.e., performed by machine). The recovered IgG can then be used immediately (e.g., administered therapeutically to a patient in need thereof) or further processed and/or stored (e.g., frozen).

Example 5

A 25 year old healthy male human volunteer (who may be referred to as a patient) weighing 150 pounds agrees to donate some of his blood. The typical amount of blood donated is 1 pint. The healthy donor agrees to donate his whole blood using a plasma apheresis machine, with the modifications described herein. This process typically takes 1 to 2 hours.

The vein on the left arm of the volunteer patient is punctured with a 16 gauge needle. The volunteer's blood is initially mixed with an appropriate amount of an anticoagu-lant solution in the tubing attached to the needle. Note that the blood at this stage is still whole blood, because although it has been mixed with an anticoagulant, no components have been removed from the blood. The anticoagulated whole blood is then drawn into a collection bowl and is separated by centrifugal force into its various components. When the collection bowl reaches its collection capacity, the plasma component will exit the collection bowl and be placed into a plasma collection container. It is from this plasma in the plasma collection container that the immuno-globulin will be extracted.

In this example, the non-collected components of the donor volunteer's blood (e.g., red blood cells and white blood cells including platelets) are mixed with isotonic saline (e.g., 0.9% w/v NaCl solution) and returned to the donor volunteer.

In this Example 5, the plasma collection container is a bag. To prepare the bag (prior to attachment of the bag to the plasmapheresis machine), the bag is fitted at the input port with a frith (or filter) having a 20-30 micron pore size). The inner surface of the bag is covered with a mesh membrane having a pore size of 20-30 microns. 230-250 ml MabCapture A beads are added to the bag. The bag is then rinsed at least once with sterile PBS, pH 7.4.

The bag containing the beads is attached to the plasmapheresis machine, and the plasma from the donor added to the bag.

In some embodiments, the bag filled with plasma is detached from the plasmapheresis machine and placed onto a mixer at room temperature to mix the contents of the bag (e.g., by rotating or shaking the bag). After a sufficient amount of time (e.g., fifteen minutes) to allow any IgG in the bag to non-covalently bind to the MabCapture beads, the IgG depleted (or reduced) plasma is poured out of the bag and either saved for further processing or discarded. The IgG depleted plasma can also be returned to the donor. 250 ml elution solution (e.g., 100 mM sodium citrate, pH 3.0) is added to the bag, and the bag replaced onto the mixer. After about 15 minutes, 25 ml of 1 M Tris, pH 8.8 is added to the bag, and the entire contents of the bag are collected for future use (e.g., further processing, storage, or immediate use therapeutically to a patient in need).

In some embodiments, the bag filled with plasma is rotated or shaken while the bag is still attached to the plasmapheresis machine. In some embodiments, the bag is mixed after it is filled to capacity with plasma. For example, the mixing can start after closing off the tubing into the bag (e.g., using a clam switching device to the closed position). In some embodiments, the bag is rotated or shaken while the plasma is added to the bag. In some embodiments, the bag is continuously filled and emptied with a portion of the plasma being processed while the bag is being rotated or shaken.

Eventually, after all of the plasma (e.g., 1000 ml) is passed through the bag such that it contacts the solid support covalently bonded to the ligand in the bag, the bag is emptied of IgG-reduced plasma while it is still attached to the apheresis machine (i.e., "on-line") or after the bag is detached from the machine (i.e., off-line). Of course, the solid support (e.g., the beads) will still remain wet due to surface tension. The elution solution is then added to the bag. The elution solution (now containing the detached IgG) can be collected on-line or off-line, and neutralization buffer added. Where the bag is on-line, the contact, elution, and/or neutralization steps can all be performed automatically (e.g., by the apheresis machine).

Example 6

After a blood drive that results in donations of whole blood (from straight blood draws), platelet-rich plasma (from plateletpheresis procedures) and plasma (from plasmapheresis procedures), the various components of blood are delivered, at 4° C., to a processing facility. Note that all of these products may be in containers (e.g., bags). Note that all of these products may contain an anticoagulant such as sodium citrate.

Figure 17:
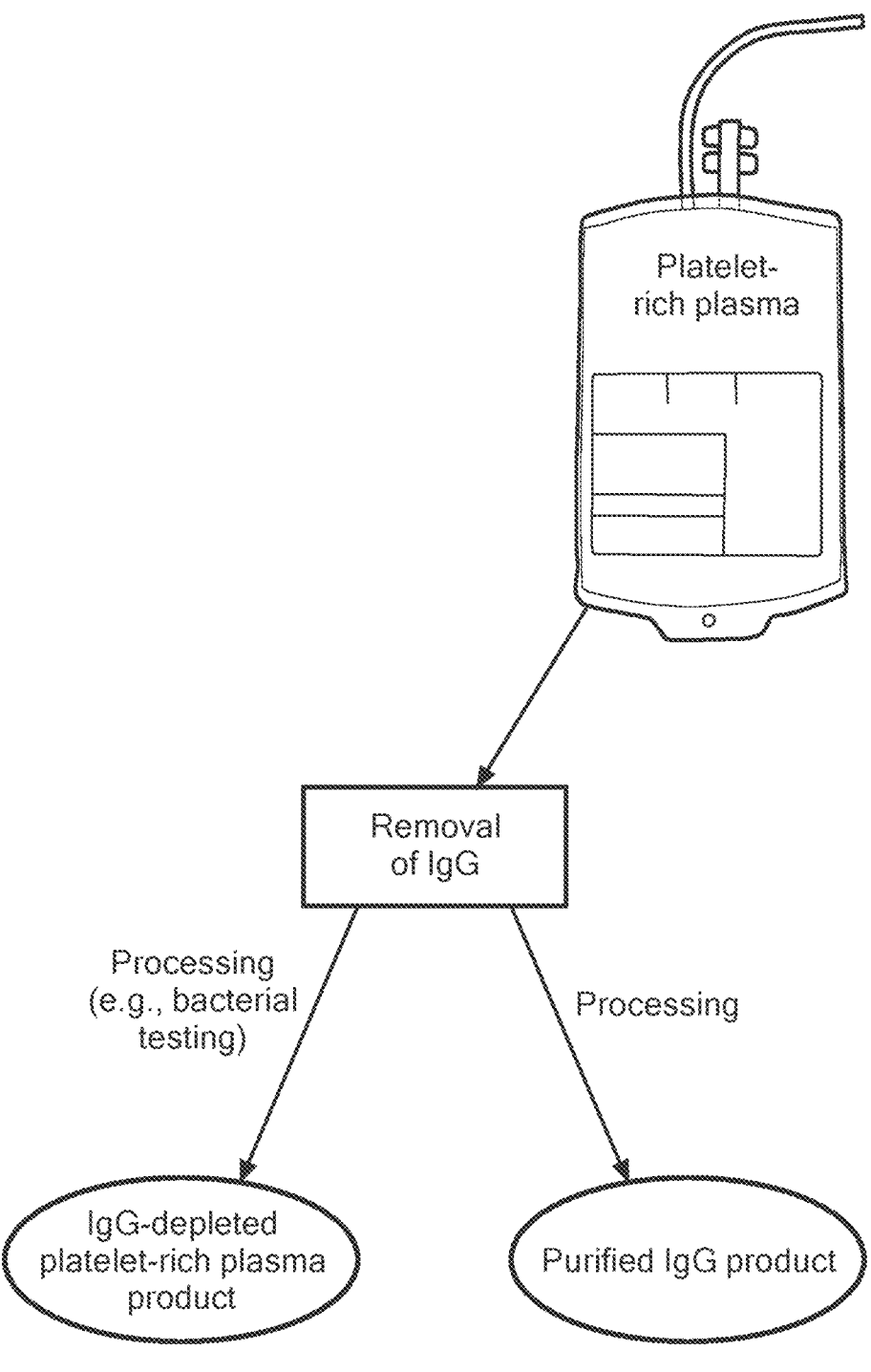
FIG. 17 is a schematic diagram showing removal of IgG from a non-limiting biological fluid, namely platelet-rich plasma collected from a donor via an apheresis procedure. As shown, following the extraction of the IgG from the platelet-rich plasma, and following further processing, two products are obtained—Ig-depleted platelet-rich plasma and purified IgG product.

In the blood processing facility, the blood products are processed. There are approximately 150,000 to 450,000 platelets per microliter of whole blood. The platelet-rich plasma may contain between 3 to 5 times as many platelets as whole blood. Using the methods and devices described herein, immunoglobulin, such as IgG, can be removed from the platelet-rich plasma. In some embodiments, IgG is extracted from the platelet-rich plasma from a single donor. It should be noted that platelet-rich plasma from multiple donors can be pooled prior to removing IgG from the pooled platelet-rich plasma. As shown in FIG. 17, following removal of IgG, and following further processing, two products are obtained, namely a purified IgG product and an IgG-depleted platelet-rich plasma product. The IgG-depleted platelet-rich plasma product may be used similarly as regular (i.e., IgG-containing) platelet-rich plasma product including, for example, treatment of osteoarthritis, treatment of chronic plantar fasciitis, treatment of tendinitis, and plastic surgery.

Figure 18:
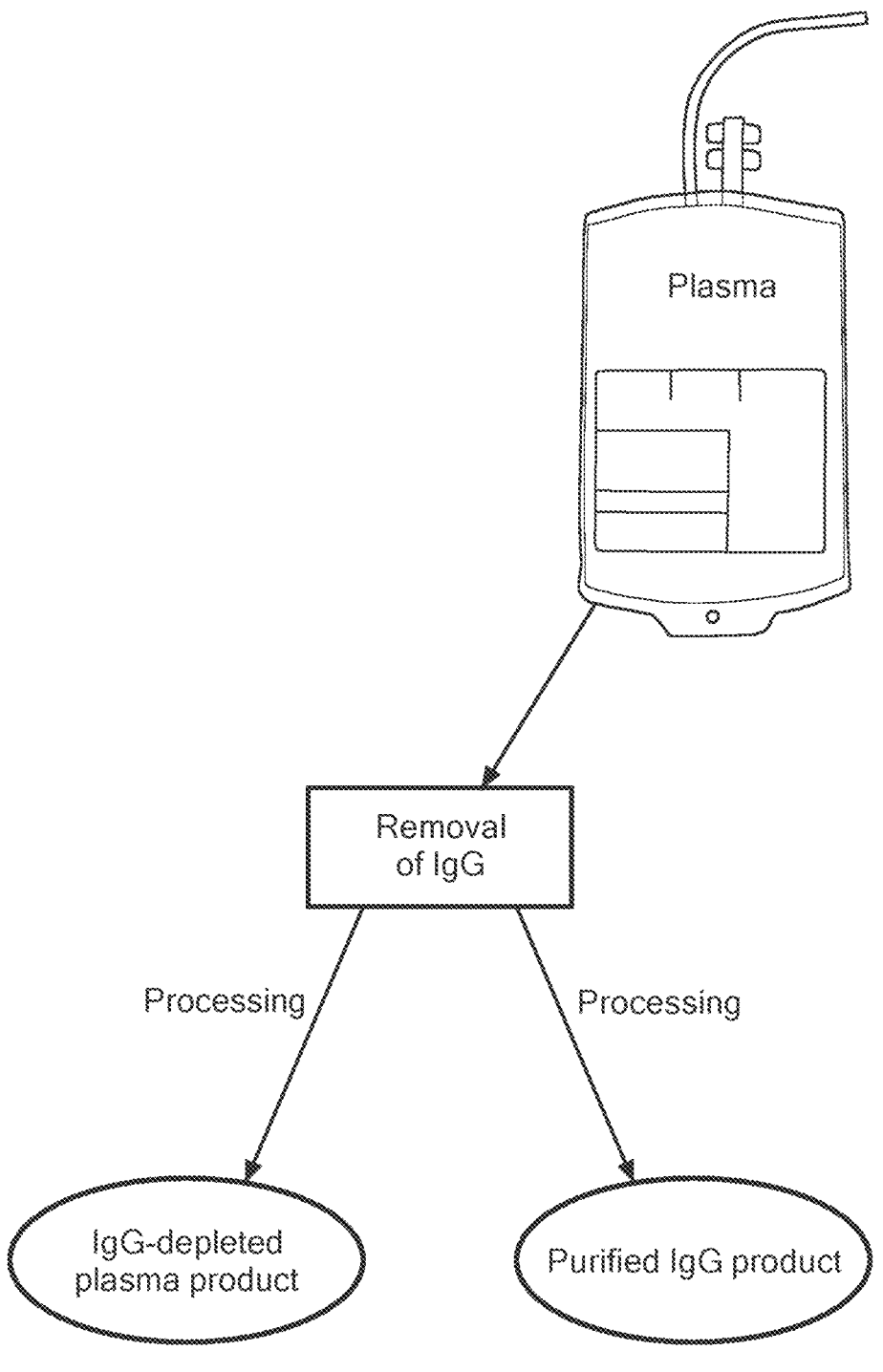
FIG. 18 is a schematic diagram showing removal of IgG from a non-limiting biological fluid, namely plasma collected from a donor via an apheresis procedure (e.g., plasmapheresis using a PCS®2 machine). As shown, following the extraction of the IgG from the plasma, and following further processing, two products are obtained—Ig-depleted plasma and purified IgG product.

Also in the blood processing facility, plasma obtained either from plasmapheresis or from processing of whole blood to separate plasma from the blood can be further processed to extract immunoglobulin such as IgG. IgG can be extracted from plasma from a single donor, or pooled plasma from multiple donors. As shown in FIG. 18, following removal of IgG, and following further processing, two products are obtained, namely a purified IgG product and an IgG-depleted plasma product. The IgG-depleted plasma product may be used similarly as regular (i.e., IgG-containing) plasma product including, without limitation, a source for plasma proteins such as albumin and coagulation factors (e.g., Factor IX).

Figure 19:
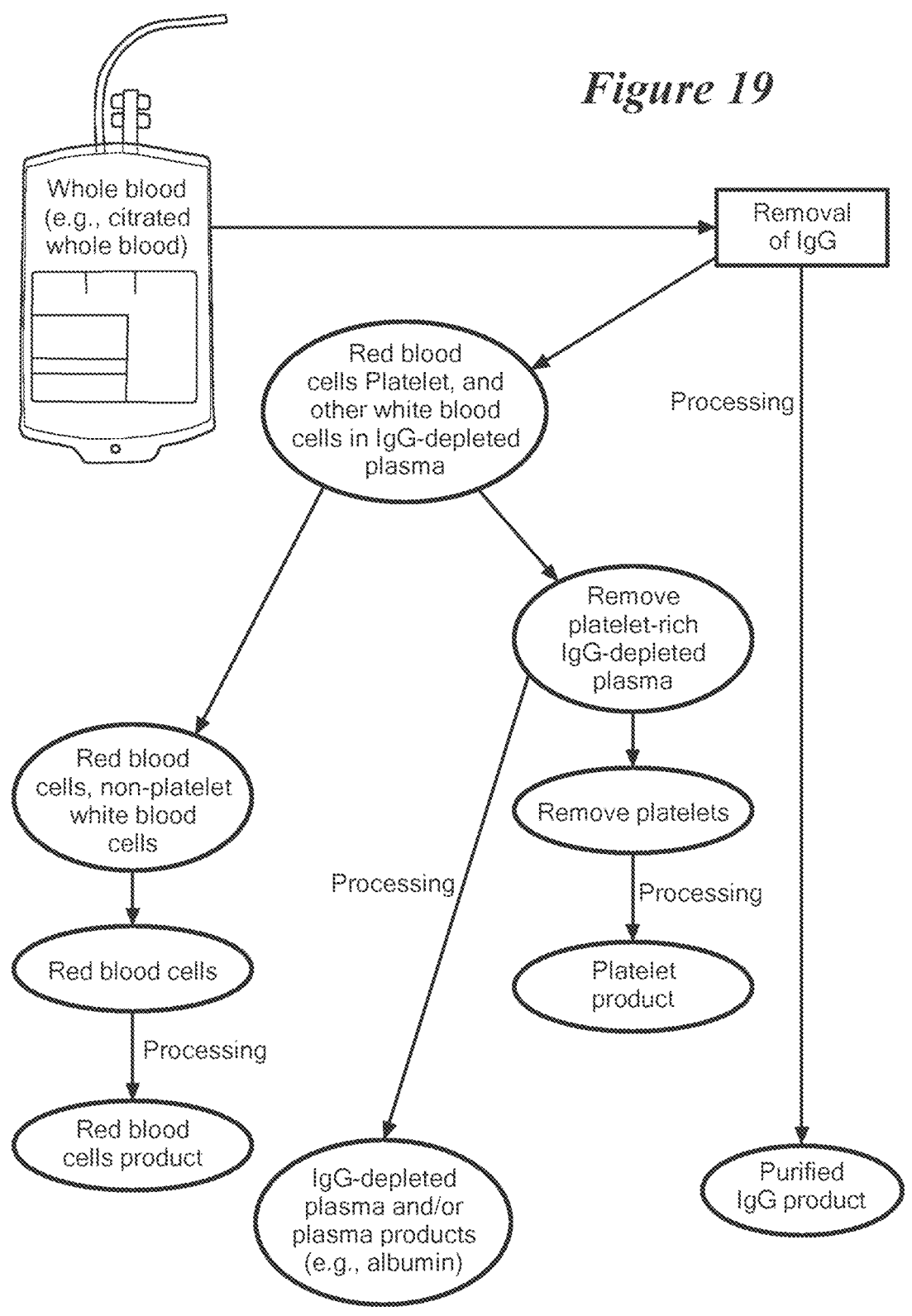
FIG. 19 is a schematic diagram showing removal of IgG from a non-limiting biological fluid, namely whole blood (which may contain an anticoagulant such as citric acid). As shown, IgG is removed from the whole blood using the methods and devices described herein. Following the extraction of the IgG from the plasma, and following further processing, a purified IgG product is obtained. The remaining blood (i.e., the IgG-depleted whole blood) can be further processed to finally obtain blood products including red blood cells (e.g., packed red blood cells), IgG-depleted plasma (or a plasma product), and a platelet product.

Also in the blood processing facility, whole blood (e.g., citrated whole blood) can be processed. The whole blood from a single donor can be processed, or the whole blood from multiple donors (e.g., matched for ABO antigen and Rh factor) can be pooled prior to processing. The processing is depicted in FIG. 19. As shown in FIG. 19, whole blood is separated into four final products—red blood cells, IgG-depleted plasma (or plasma products such as albumin or fibrinogen), platelets, and IgG. In the process schematically depicted in FIG. 19, the nucleated white blood cells are simply discarded. Note that in FIG. 19, if platelet-rich IgG-depleted plasma is the desired product, the platelet-removal step can be skipped, and the platelet-rich IgG-depleted plasma can be further processed (e.g., filtered or tested for presence of bacteria) to product a platelet-rich IgG-depleted plasma product.

For all of FIG. 17-19, it will be understood that the methods and devices (e.g., containers) used to remove immunoglobulin (such as IgG) from the biological fluid may vary depending upon whether or not that biological fluid contains cells. These same considerations apply to all the processes described herein including, without limitation, the schematic processes depicted in FIGS. 6A, 6B, 6C, 7, and 11.

For example, in the schematic depicted in FIG. 17 (and in FIG. 6B), the biological fluid from which the IgG is extracted contains platelets. As platelets are only about 2 um to about 3 um in diameter, a container that contains a solid support covalently bonded to a ligand that specifically binds to IgG that will be used to remove IgG from the biological fluid would, in some embodiments, be configured so that the platelets can easily flow through the container while the IgG is extracted (e.g., by non-covalently specifically binding to the ligand). For example, if the container is a bag or a column, the inlet and outlet of the container may be fitted with a filter having a pore size that is greater than 3 um (e.g., a pore size of at least 3.5 um, such as a pore size 5 um or a pore size of 10 um). Likewise, if the solid support is beads in a bag or a column, the beads may have a diameter large enough (e.g., such as 5 um or 10 um, or 25 um, or 50 um, or 100 um), so that the gaps between the beads is large enough that a 3 um diameter platelet can freely flow through the gaps.

When the biological fluid from which the IgG is to be extracted contains red blood cells and nucleated white blood cells (such as lymphocytes or monocytes), the methods and devices used to extract immunoglobulin (e.g., IgG) from the biological fluid will similarly be configured to accommodate flow-through of these cells. Monocytes are the largest blood cell, and can vary from about 15 um to about 30 um in diameter. Thus, in the methods described herein that remove immunoglobulin directly from whole blood (e.g., FIGS. 7 and 19), a container that contains a solid support covalently bonded to a ligand that specifically binds to IgG that will be used to remove IgG from the biological fluid would, in some embodiments, be configured so that that monocytes (and thus all blood cells) can easily flow through the container while the IgG is extracted (e.g., by non-covalently specifically binding to the ligand). For example, if the container is a bag or a column, the inlet and outlet of the container may be fitted with a filter having a pore size that is greater than 30 um (e.g., a pore size of at least 35 um, such as a pore size 50 um or a pore size of 100 um). Likewise, if the solid support is beads in a bag or a column, the beads may have a diameter large enough (e.g., such as 50 um or 100 um, or 250 um), so that the gaps between the beads is large enough that a 30 um diameter monocyte can freely flow through the gaps.

It should be noted that container and methods can be modified depending upon the types of cells are in the biological fluid from which the IgG is being extracted. Lymphocytes can vary in diameter from about 7 um to about 20 um. Eosinophils and basophils range from about 10 um to about 12 um in diameter and about 12 um to about 15 um in diameter, respectively. The diameter of red blood cell will vary depending upon the maturity level of the red blood cell. A mature red blood cell, which lacks a nucleus, is typically about 6 um to about 8 um in diameter, while an immature nucleated red blood cell may have a diameter between about 10 um to about 15 um. Thus, the container and the solid support covalently bonded to the ligand can be modified appropriately.

For example, the present disclosure contemplates processes in which all nucleated blood cells (e.g., non-platelet white blood cells and immature red blood cells) are removed from a biological fluid This could be easily performed by centrifugation, or simply by gravity, because the nucleated cells have a higher mass than the non-nucleated cells. Thus, only the a-nucleated platelets and mature blood cells are in the biological fluid, with mature blood cells being the largest. The methods and devices described herein may serve a dual role—by extracting immunoglobulin from the biological fluid (which immunoglobulin can be later eluted from the ligand) and by extracting mature red blood cells from the biological fluid. For example, since mature red blood cells are between about 6-8 um in diameter while platelets are between about 2-3 um in diameter, a container that contains a solid support covalently bonded to a ligand that specifically binds to IgG that will be used to remove IgG from the biological fluid would, in some embodiments, be configured so that that platelets can easily flow through the container while the IgG is extracted (e.g., by non-covalently specifically binding to the ligand) but mature red blood cells (or any other nucleated red blood cell or white blood cell) cannot flow through. For example, if the container is a bag or a column, the inlet and outlet of the container may be fitted with a filter having a pore size that is greater than 3 um but smaller than 6 um (e.g., a pore size of between about 3.5 um to about 5.5 um). Likewise, if the solid support is beads in a bag or a column, the beads may have a diameter large enough (e.g., such as 5 um, so that the gaps between the beads is large enough that a 3 um diameter platelet can freely flow through the gaps but a cell with a diameter larger than 3 um will be trapped. Of course, the trapped cell would clog the column so in some embodiments, beads would have a larger diameter (e.g., 50 um), and the trapping of cells with diameters larger than 3.0 um can take place at the inlet of the container (e.g., through a filter with a pore size of between about 3 um to about 6 um).

In the various embodiments of the different processes described herein, the starting concentration of the immunoglobulin of choice (e.g., of the IgG isotype) can be determined in the biological fluid from which the Ig is directly extracted (e.g., plasma in the embodiment shown in FIG. 18 or whole blood in the embodiment shown in FIG. 19). In some embodiments, the starting concentration of the immunoglobulin of choice (e.g., of the IgG isotype) can be determined in the biological fluid from which the Ig is indirectly extracted (e.g., from whole blood in the embodiment shown in FIGS. 6A-6C).

The embodiments of the invention described above are intended to be merely exemplary; numerous variations and modifications will be apparent to those skilled in the art. All such variations and modifications are intended to be within the scope of the present invention as defined in any appended claims.

The invention claimed is:

1. A method for collecting immunoglobulin from whole blood from a donor, the method comprising:

providing a set including a separation container having an inlet and an outlet, and comprising a solid support covalently bonded to a ligand that specifically binds to immunoglobulin, wherein the separation container is configured to support the plasma product passing through the separation container at a flow rate of between about 20 ml/minute to about 120 ml/minute, and to support the plasma product passing through the separation container with a backpressure of between about 10 mm Hg to about 100 mmHg;

a blood cell collection bag having an inlet and an outlet;

a centrifuge bowl coupled to:

(a) the inlet of the separation container, the centrifuge bowl being configured to separate a plasma product from the whole blood and direct the plasma product to the inlet of the separation container, and (b) the inlet of the blood cell collection bag; and a collection container coupled to the outlet of the separation container, and adapted for collecting purified immunoglobulin product, wherein the separation container is in-line with the centrifuge bowl and the collection container so as to form a closed system to prevent the loss of sterility within the set, the separation container, the blood cell collection bag, the centrifuge bowl, and the collection container remain coupled as parts of the set while the plasma product is being separated from the whole blood and while the immunoglobulin is binding to the ligand in the separation container;

withdrawing the whole blood from a donor;

supplementing the whole blood with an anticoagulant;

introducing the withdrawn whole blood into the centrifuge bowl, spinning the centrifuge bowl to separate the plasma product from other blood components of the whole blood, directing the plasma product to the separation container, and directing the other blood components to the blood cell collection bag;

after the plasma product has been directed to the separation container, contacting the plasma product with the solid support covalently bonded to the ligand that specifically binds to immunoglobulin in the separation container under conditions sufficient for non-covalent binding of the immunoglobulin to the ligand;

after the non-covalent binding of the immunoglobulin to the ligand, contacting the solid support in the container with an elution solution under conditions whereby the non-covalently bound immunoglobulin is released from the ligand and into the elution solution to obtain elution solution comprising the immunoglobulin;

collecting the eluted immunoglobulin in the collection container; and returning one or more of the other blood components from the blood cell collection bag to the donor while continuing to withdraw additional whole blood from the donor, such that the method can be performed chairside by the donor.

2. A method for collecting an immunoglobulin-enriched plasma product from whole blood from a donor, the method comprising:

providing a set including a separation container having an inlet and an outlet, and comprising a solid support covalently bonded to a ligand that specifically binds to a non-immunoglobulin component in the whole blood, wherein the separation container is configured to support the plasma product passing through the separation container at a flow rate of between about 20 ml/minute to about 120 ml/minute, and to support the plasma product passing through the separation container with a backpressure of between about 10 mm Hg to about 100 mmHg;

a blood cell collection bag having an inlet and an outlet;

a centrifuge bowl coupled to:

(a) the inlet of the separation container, the centrifuge bowl being configured to separate a plasma product from the whole blood and direct the plasma product to the inlet of the separation container, and (b) the inlet of the blood cell collection bag; and a collection container coupled to the outlet of the separation container, and adapted for collecting immunoglobulin-enriched plasma product, wherein the separation container is in-line with the centrifuge bowl and the collection container so as to form a closed system to prevent the loss of sterility within the set, the separation container, the blood cell collection bag, the centrifuge bowl, and the collection container remain coupled as parts of the set while the plasma product is being separated from the whole blood and while the non-immunoglobulin component is binding to the ligand in the separation container;

withdrawing the whole blood from a donor;

supplementing the whole blood with an anticoagulant;

introducing the whole blood into the centrifuge bowl, spinning the centrifuge bowl to separate the plasma product from other blood components of the whole blood, directing the plasma product to the separation container, and directing the other blood components to the blood cell collection bag;

after the plasma product has been directed to the separation container, contacting the plasma product with the solid support in the separation container under conditions sufficient for non-covalent binding of the non-immunoglobulin component to the ligand;

after the non-covalent binding of the non-immunoglobulin component to the ligand, collecting the immunoglobulin-enriched plasma product in the collection container, depleted of the non-immunoglobulin component from the separation container; and returning one or more of the other blood components from the blood cell collection bag to the donor while continuing to withdraw additional whole blood from the donor, such that the method can be performed chairside by the donor.

3. The method of claim 1, wherein the method is a partially or fully automated method.

4. The method of claim 1, wherein the solid support are beads.

5. The method of claim 1, wherein the ligand is a protein from a bacteria family selected from the group consisting of *Staphylococcus* or *Streptococcus*, or a derivative thereof.

6. The method of claim 1, wherein the plasma product is platelet-enriched plasma or plasma.

7. The method of claim 1, wherein the separation container is a column or bag.

8. The method of claim 1, wherein the executed method further comprises adding a neutralizing buffer to the elution solution comprising immunoglobulin to result in a final solution comprising immunoglobulin having a pH of between about 7.0 and about 8.0.

9. The method of claim 2, wherein the solid support are beads.

10. The method of claim 2, wherein the plasma product is platelet-enriched plasma or plasma.

11. The method of claim 2, wherein the separation container is a column or bag.

* * * * *